(12) United States Patent
Baura et al.

(10) Patent No.: US 7,149,576 B1
(45) Date of Patent: Dec. 12, 2006

(54) APPARATUS AND METHOD FOR DEFIBRILLATION OF A LIVING SUBJECT

(75) Inventors: Gail D. Baura, San Diego, CA (US); Jeremy R. Malecha, San Diego, CA (US); Patrick W. Bradley, San Diego, CA (US)

(73) Assignee: Cardiodynamics International Corporation, San Diego, CA (US)

( * ) Notice: Subject to any disclaimer, the term of this patent is extended or adjusted under 35 U.S.C. 154(b) by 448 days.

(21) Appl. No.: 10/393,544

(22) Filed: Mar. 19, 2003

Related U.S. Application Data

(63) Continuation-in-part of application No. 09/903,473, filed on Jul. 10, 2001, now Pat. No. 6,602,201, which is a continuation-in-part of application No. 09/613,183, filed on Jul. 10, 2000, now Pat. No. 6,636,754.

(51) Int. Cl.
*A61N 1/39* (2006.01)
(52) U.S. Cl. .......................................... 607/6
(58) Field of Classification Search ................ 607/5–8
See application file for complete search history.

(56) References Cited

U.S. PATENT DOCUMENTS

| RE30,101 E | 9/1979 | Kubicek et al. |
|---|---|---|
| 5,178,151 A | 1/1993 | Sackner |
| 5,184,620 A | 2/1993 | Cudahy et al. |
| 5,287,520 A | 2/1994 | Kaiser |
| 5,505,209 A | 4/1996 | Reining |
| 5,511,553 A | 4/1996 | Segalowitz |
| 5,590,648 A | 1/1997 | Mitchell et al. |
| 5,876,351 A | 3/1999 | Rohde |
| 5,895,298 A | 4/1999 | Faupel et al. |
| 6,016,445 A | 1/2000 | Baura |
| 6,141,575 A | 10/2000 | Price |
| 6,186,955 B1 | 2/2001 | Baura |
| 6,480,734 B1 | 11/2002 | Zhang et al. |
| 6,490,478 B1 | 12/2002 | Zhang et al. |
| 2002/0138014 A1 | 9/2002 | Baura et al. |
| 2003/0195576 A1 | 10/2003 | Warren |

OTHER PUBLICATIONS

Solar®8000M Patient Monitor *GE Medical Systems* web pages (6 pages).
Non-Invasive Hemodynamic Monitoring with BioZ® Impedance Cardiography information pages (2 pages).
W. G. Kubicek, Ph.D., et al., "Development and Evaluation of an Impedance Cardiac Output System", Acrospace Medicine, pp. 1208-1212, (Dec. 1966).
Jan Nyboer, Sc.D., M.D., et al., "Electrical Impedance Plethysmography", Circulation, vol. II, pp. 811-821, Dec. 1950.

(Continued)

*Primary Examiner*—Scott M. Getzow
(74) *Attorney, Agent, or Firm*—Gazdzinski & Associates

(57) ABSTRACT

An improved apparatus and method for evaluating the need for, and performing as applicable, defibrillation. In one aspect, an improved defibrillation apparatus utilizing cardiographic impedance waveforms for determining cardiac output and accurately correlating this output to shockable or non-shockable cardiac conditions is disclosed. One exemplary embodiment uses electrodes having optimal spacing to enhance the accuracy of the impedance measurement. Another exemplary embodiment uses time-scale processing of the waveforms to identify fiducial points therein. Yet another embodiment uses advanced decision logic (such as fuzzy logic) to perform the aforementioned evaluation. The use of pacing spike detection and beat parsing based thereon is also disclosed.

41 Claims, 43 Drawing Sheets

OTHER PUBLICATIONS

ConMed Corporation POSITRACE ECG Electrode (Exhibit "A" consisting of five pages), Jun. 1998.

G. W. N. Dalzell, et al., "Initial Experience with a Microprocessor Controlled Current Based Defibrillator," University of Ulster, Jordanstown, and Regional Medical Cardiology Centre, Royal Victoria Hospital, Belfast, Ireland, pp. 502-505, Feb. 2, 1989.

B. Bo Sramek, MSEE, "Hemodynamic and Pump-Performance Monitoring by Electrical Bioimpedance," Problems in Respiratory Care, vol. 2, No. 2, pp. 274-290, Apr./Jun. 1989.

G. D. Baura, Ph.D., et al., "Intra-Sensor Spacing and Sensor Placement Variability on Impedance Cardiography (ICG) Parameters," CDIC Technical Report #TR-048, consisting of 2 pages, Jul. 26, 2000.

GE Medical Systems Information Technologies, "Non-Invasive Hemodynamic Monitoring With BioZ Impedance Cardiography," consisting of 2 pages, 2001.

Wantagh, Incorporated, "Noninvasive Continuous Hemodynamic Patient Monitoring System—Operator's Manual", Title page & pp. 1-42 (date unk.).

Wantagh, Incorporated, "Noninvasive Continuous Hemodynamic Monitoring," pp. 1-4 (date unknown).

Lead-Lok, Inc., (Aug. 8, 1998), Final Production Specifications consisting of two (2) pages.

Sorba Medical Systems—product literature entitled "Transthoracic Electrical Bioimpedance R-wave Triggered Ensemble" Averaging consisting of 4 pages.

Sorba Medical Systems—product literature regarding the CIC-1000™-consisting of two (2) pages.

Sorba Medical Systems—product literature regarding the Steorra™ impedance cardiograph—consisting of three (3) pages.

American Heart Association, Inc. Scientific Statement entitled: Automatic External Defibrillators for Public Access Defibrillation: Recommendations for Specifying and Reporting Arrhythmia Analysis Algorithm Performance, Incorporated New Waveforms, and Enhancing Safety at Richard E. Kerber, MD, et al., pp. 1677-1681 (1997).

Philips Medical Systems—Heartstream AED Technical Reference Manual—Edition 2, pp. 4-1 thru 4-8 (2002).

IEEE Transactions on Biomedical Engineering, vol. BME-26, No. 4, article entitled: The Impedance Plethysmographic Sampling Field in the Human Calf by Bill C. Penney, et al., pp. 193-198 (Apr. 1979).

Medical & Biological Engineering & Computing article entitled: "Impedance Plethysmography: the Origin of Electrical Impedance Changes Measured in the Human Calf" by F.A. Anderson, Jr., et al., pp. 234-240, (Mar. 1980).

European Heart Journal article entitled "The transthoracic impedance cardiogram is a potential haemodynamic sensor for an automated external defibrillator" by P.W. Johnston, et al., pp. 1879-1888, Article No. hj981199, (1998).

EMS article entitled "Performance and Error Analysis of Automated External Defibrillator use in the Out-of-Hospital Setting" by Russell D. MacDonald, MD. MPH, et al., pp. 262-267, (Sep. 2001).

Department of Physiology, Institute of Basic Medical Sciences, Univ. of Oslo, article entitled "Respiration-Synchronous Fluctuations in Stroke Volume, Heart Rate and Arterial Pressure in Humans" by Karin Toska and Morten Eriksen, pp. 501-505.

Product data sheets for Lifeguard ICG Hemodynamic Status Monitor by Analogic Corporation, no date, 2 pages, www.analogic.com/lifegard.

BioZ ICG Monitor Specifications and Parameters product data sheets by CardioDynamics, no date, 2 pages, www.cardiodynamics.com.

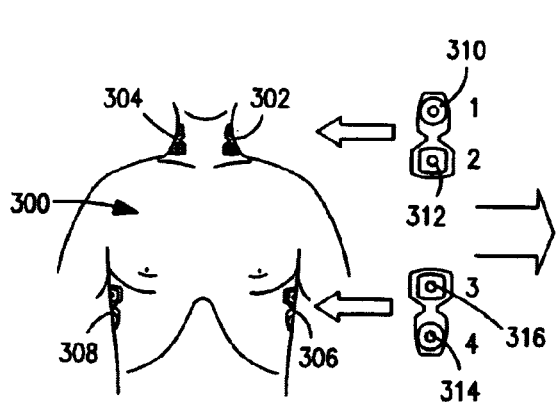 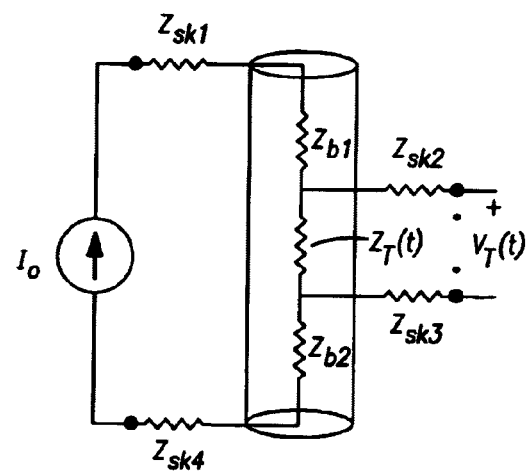
FIG. 3a  FIG. 3b

(PART 1 OF 2)

(PART 2 OF 2)

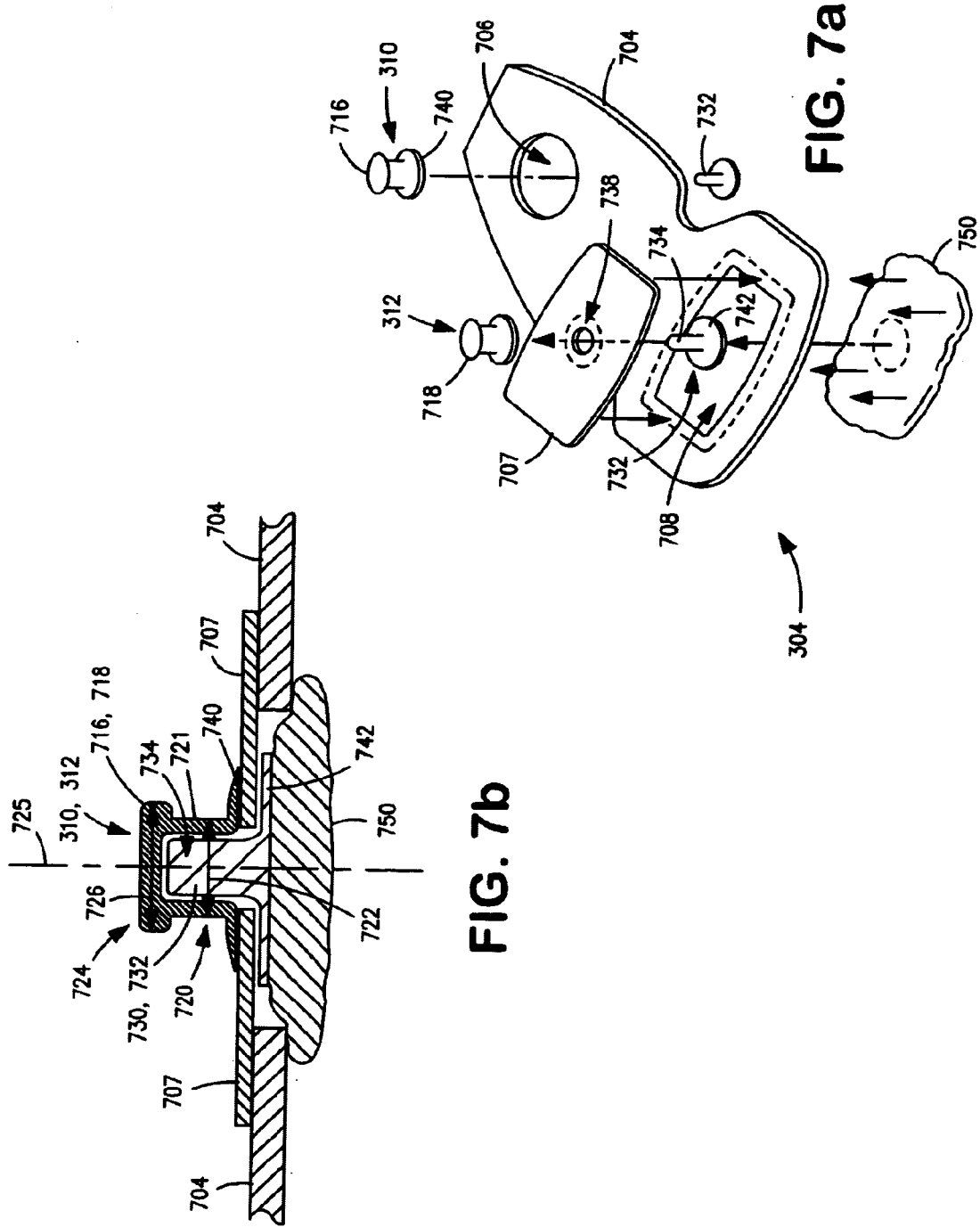

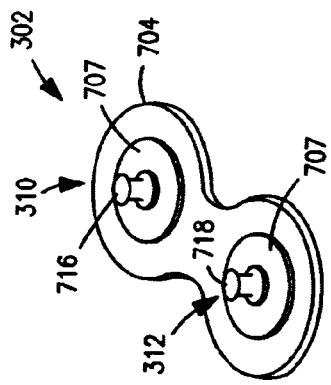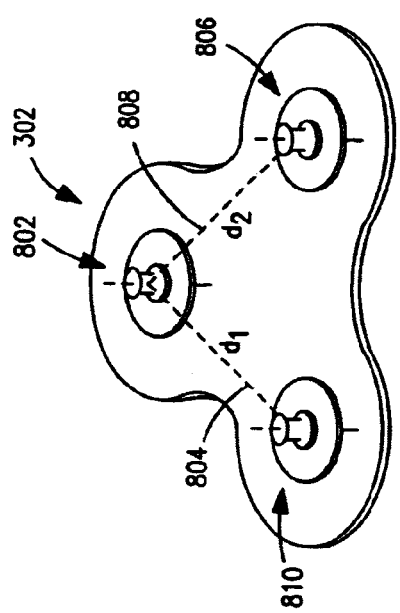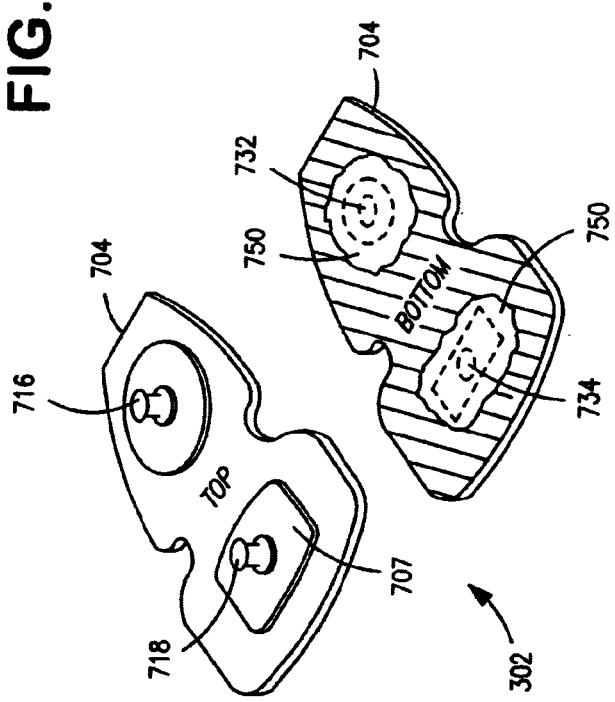

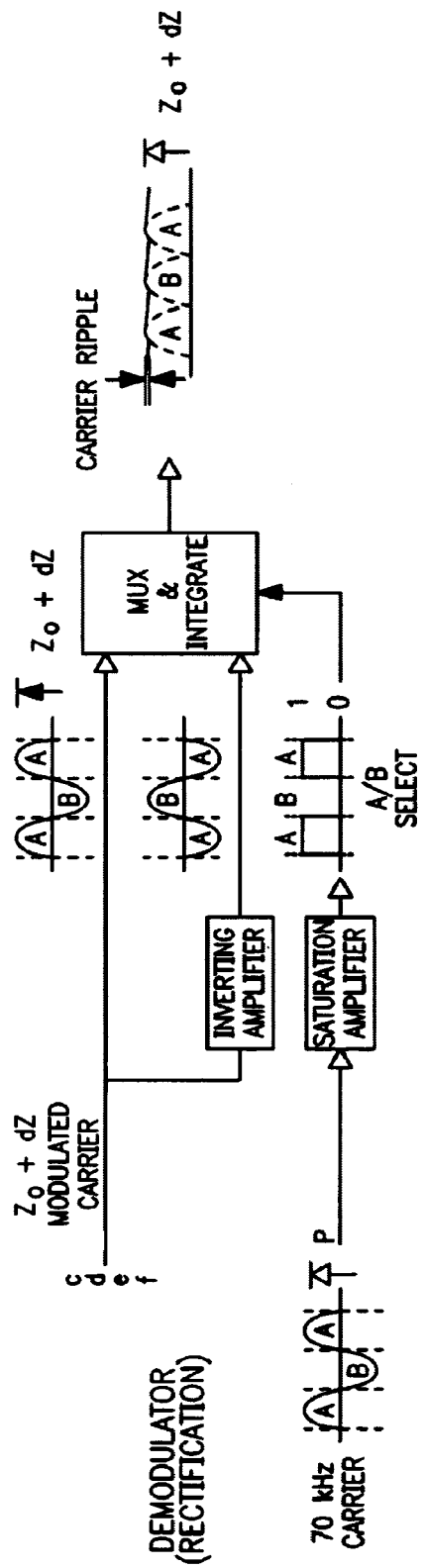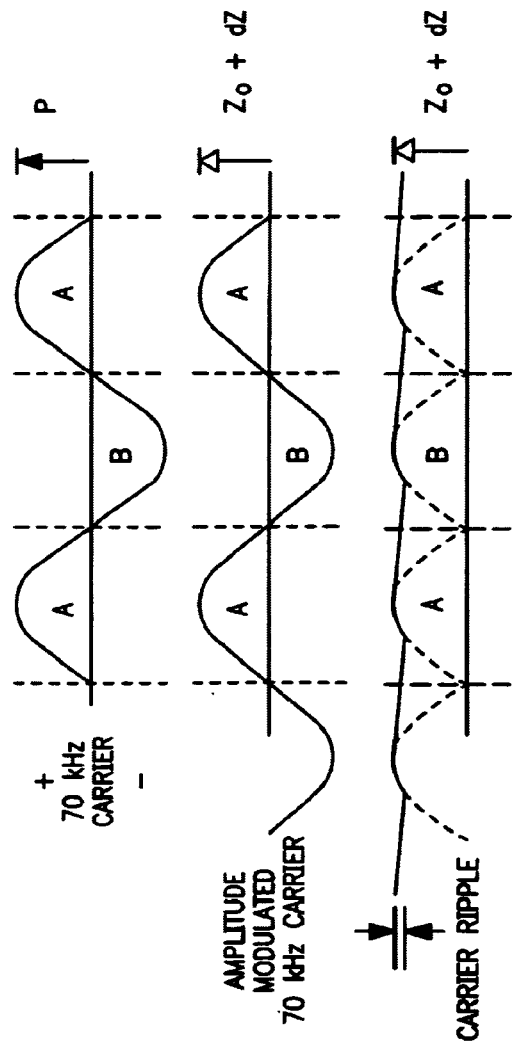
FIG. 13a

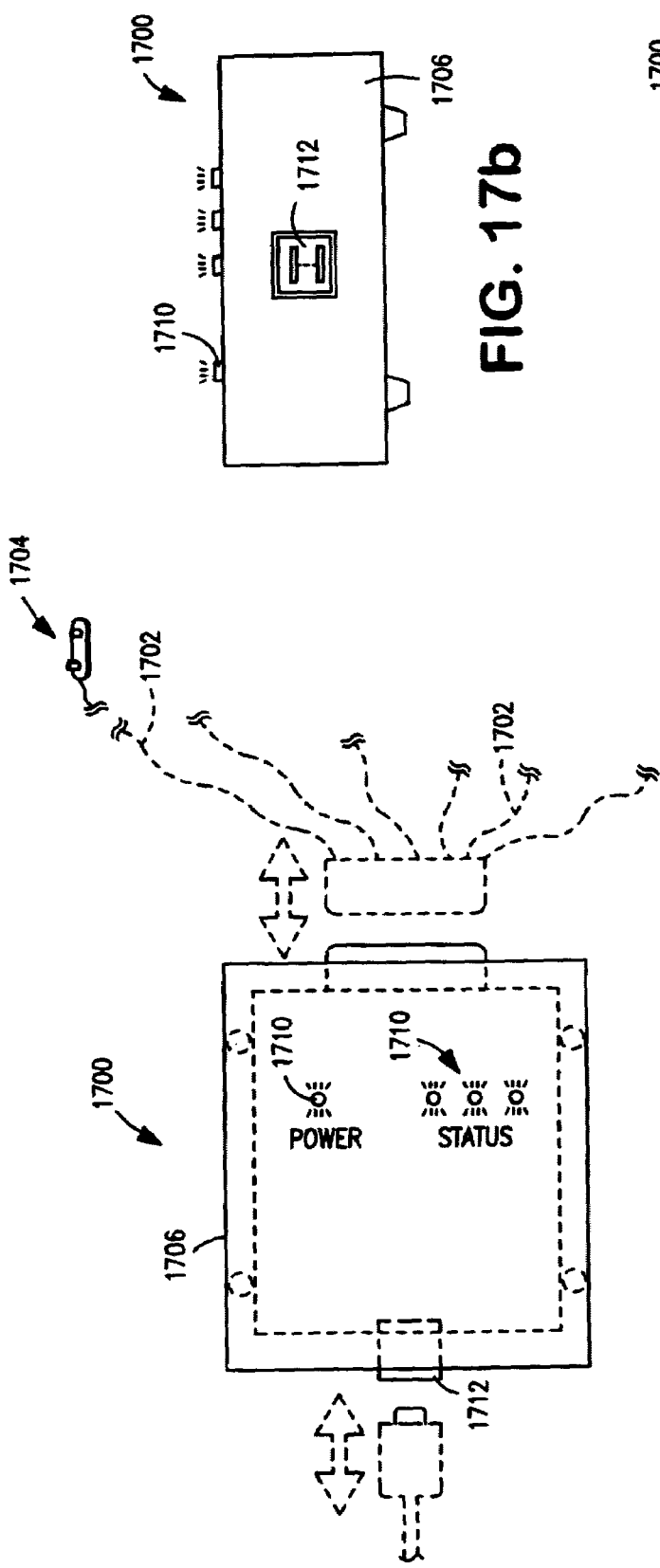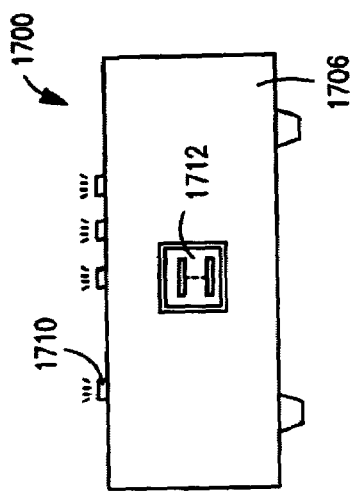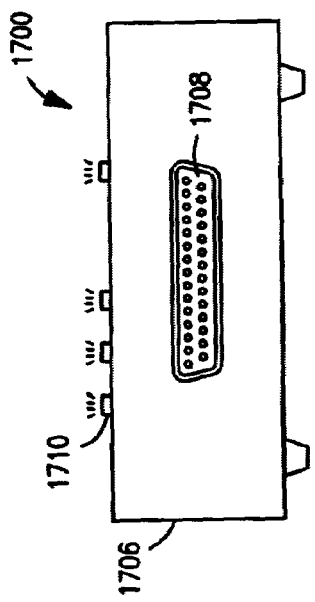

APPARATUS AND METHOD FOR DEFIBRILLATION OF A LIVING SUBJECT

This application is a continuation-in-part of U.S. patent application Ser. No. 09/903,473 entitled "Apparatus And Method For Determining Cardiac Output In A Living Subject" filed Jul. 10, 2001 now U.S. Pat. No. 6,602,201, which is a continuation-in-part of U.S. patent application Ser. No. 09/613,183 entitled "Apparatus And Method For Determining Cardiac Output In A Living Subject" filed Jul. 10, 2000 now U.S. Pat. No. 6,636,754, both assigned to the Assignee hereof, both incorporated herein by reference in their entirety.

RELATED APPLICATIONS

This application is related to co-pending U.S. patent application Ser. No. 09/764,589 entitled "Method And Apparatus For Hemodynamic Assessment Including Fiducial Point Detection" filed Jan. 17, 2001, and Ser. No. 10/329,129 entitled "Method and Apparatus for Waveform Assessment" filed Dec. 24, 2002, both of which are assigned to the Assignee hereof and incorporated by reference herein in their entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

The present invention relates generally to the field of biomedical analysis and treatment, and in one exemplary aspect to an apparatus and method for evaluating the need for, and applying, defibrillating electrical current.

2. Description of Related Technology

Noninvasive estimates of cardiac output (CO) can be obtained using impedance cardiography. Strictly speaking, impedance cardiography (ICG), also known as thoracic bioimpedance or impedance plethysmography, is used to measure the stroke volume of the heart. As shown in Eqn. (1), when the stroke volume is multiplied by heart rate, cardiac output is obtained.

$$CO = \text{stroke volume} \times \text{heart rate}. \quad (1)$$

The heart rate is obtained from an electrocardiogram. The basic method of correlating thoracic, or chest cavity, impedance, $Z_T(t)$, with stroke volume was developed by Kubicek, et al. at the University of Minnesota for use by NASA. See, e.g., U.S. Reissue Patent No. 30,101 entitled "Impedance plethysmograph" issued Sep. 25, 1979, which is incorporated herein by reference in its entirety. The method generally comprises modeling the thoracic impedance $Z_T(t)$ as a constant impedance, $Z_o$, and time-varying impedance, $\Delta Z(t)$, as illustrated schematically in FIG. 1. The time-varying impedance is measured by way of an impedance waveform derived from electrodes placed on various locations of the subject's thorax; changes in the impedance over time can then be related to the change in fluidic volume (i.e., stroke volume), and ultimately cardiac output via Eqn. (1) above.

Despite their general utility, prior art impedance cardiography techniques such as those developed by Kubicek, et al. have suffered from certain disabilities. First, the distance (and orientation) between the terminals of the electrodes of the cardiography device which are placed on the skin of the subject is highly variable; this variability introduces error into the impedance measurements. Specifically, under the prior art approaches, individual electrodes 200 such as that shown in FIGS. 2a and 2b, which typically include a button "snap" type connector 202, compliant substrate 204, and gel electrolyte 206 are affixed to the skin of the subject at locations determined by the clinician. Since there is no direct physical coupling between the individual electrodes, their placement is somewhat arbitrary, both with respect to the subject and with respect to each other. Hence, two measurements of the same subject by the same clinician may produce different results, dependent at least in part on the clinician's choice of placement location for the electrodes. It has further been shown that with respect to impedance cardiography measurements, certain values of electrode spacing yield better results than other values.

Additionally, as the subject moves, contorts, and/or respirates during the measurement, the relative orientation and position of the individual electrodes may vary significantly. Electrodes utilizing a weak adhesive may also be displaced laterally to a different location on the skin through subject movement, tension on the electrical leads connected to the electrodes, or even incidental contact. This so-called "motion artifact" can also reflect itself as reduced accuracy of the cardiac output measurements obtained using the impedance cardiography device.

A second disability associated with prior art impedance cardiography techniques relates to the detection of a degraded electrical connection or loss of electrical continuity between the terminals of the electrode and the electrical leads used to connect thereto. Specifically, as the subject moves or sweats during the measurement, the electrolyte of the electrode may lose contact with the skin, and/or the electrical leads may become partially or completely disconnected from the terminals of the electrode. These conditions result at best in a degraded signal, and at worst in a measurement which is not representative of the actual physiological condition of the subject.

Another significant consideration in the use of electrodes as part of impedance cardiographic measurements is the downward or normal pressure applied to the subject in applying the electrode to the skin, and connecting the electrical leads to the electrode. It is desirable to minimize the amount of pressure needed to securely affix the electrode to the subject's skin (as well as engage the electrical lead to the electrode), especially in subjects whose skin has been compromised by way of surgery or other injury, since significant pressure can result in pain, and reopening of wounds.

It is also noted that it is highly desirable to integrate cardiac output measurement capability into a compact, rugged, and efficient platform which is readily compatible with different hardware and software environments. The prior art approach of having a plurality of different, discrete stand-alone monitors which include, for example, a dedicated, redundant display and/or other output or storage device is not optimal, since there is often a need to conserve space at the subject's bedside or even in their home (e.g., in outpatient situations), as well as cost efficiency concerns. Furthermore, a plurality of discrete stand-alone monitors necessarily consume more electrical power (often each having their own separate power supplies), and require the subject or clinician to remain proficient with a plurality of different user interface protocols for the respective monitors. In many cases, the individual stand-alone monitors are also proprietary, such that there is limited if any interface between them for sharing data. For example, where two such monitors require a common parametric measurement (e.g., ECG waveform or blood pressure), one monitor frequently cannot transmit this data to the other monitor due to the lack of interface, thereby necessitating repeating the measurement.

Recognizing these deficiencies, more recent approaches have involved the use of modular devices, wherein for example a common monitor/display function is utilized for a variety of different functional modules. These modules are generally physically mounted in a rack or other such arrangement, with the common monitor/display unit also being mounted therein. A common power supply is also generally provided, thereby eliminating the redundancy and diversity previously described. However, heretofore, impedance cardiography equipment has not been made in such modular fashion, nor otherwise compatible with other modular devices (such as blood pressure monitoring or ECG equipment), such that such other signals can be obtained directly or indirectly from these devices and utilized within the ICG apparatus. The quality or continuity of these signals, whether obtained directly from the subject being monitored or from other modules, has not been readily and reliably provided for either.

Typical patient monitors include modules for several physiologic measurements such as ECG, blood pressure, temperature, and arterial pulse oximetry. The addition of ICG provides the physician with additional useful clinical information about the patient.

Furthermore, prior art ICG devices (modular or otherwise) do not provide the facility for direct transmission of the data obtained from the subject, or other parameters generated by the ICG device after processing the input data, to a remote location for analysis or storage. Rather, the prior art approaches are localized to the bedside or monitoring location. This is a distinct disability with respect to the aforementioned outpatient applications, since the subject being monitored must either manually relay the information to the caregiver (such as by telephone, mail, or visit), or perform the analysis or interpretation themselves. Additionally, it is often desirable to perform more sophisticated (e.g. algorithmic) comparative or trend analysis of the subject's data, either with respect to prior data for that same subject, or data for other subjects. The lack of effective transmission modes in the prior art to some degree frustrates such analysis, since even if the subject has the facility to perform the analysis (e.g., PC or personal electronic device with the appropriate software), they will not necessarily be in possession of their own prior data, which may have accumulated via monitoring at a remote health care facility, or that for other similarly situated subjects.

Defibrillation

External defibrillators and defibrillation techniques are well known in the prior art. During external defibrillation, a strong current of short duration is administered across the thorax of the subject via paddles or electrodes to convert rapid non-pulsatile twitching of the heart ventricles, or ventricular fibrillation (VF), to a slower pulsatile rhythm that allows the heart to pump blood. Successful defibrillation stimulates cells by passing a given current intensity through the cells for a period of time. Typically, in the clinical environment, highly trained personnel determine if a defibrillation current (shock) should be administered. Outside of the clinical environment, personnel with little or even no training are often tasked with using portable or similar defibrillators, such as the well known automatic external defibrillator (AEDs), to analyze cardiac rhythms and, if appropriate, advise/deliver an electric shock.

A critical feature of defibrillators used by non-skilled personnel, and especially AEDs, is the accurate analysis of the electrocardiogram rhythm to determine if a defibrillation shock is necessary. As recommended by the American Heart Association (AHA) Task Force on AED, coarse VF (peak-to-peak amplitude>200 µV) and rapid ventricular tachycardia (VT) rhythms should be shocked, as they are almost always associated with a pulseless, unresponsive patient. Ventricular tachycardia refers to a rapid heartbeat (e.g., >100 beats per minute) originating in the right or left ventricle which prevents the ventricles from filling adequately with blood. This inadequate filling precludes the heart from pumping normally. VF should generally be detected and shocked with >90% sensitivity; rapid VT should generally be detected and shocked with >75% sensitivity.

Benign rhythms should also be identified, and not shocked with >95% specificity. Such benign rhythms include for example normal sinus rhythm, atrial fibrillation (rapid twitching of the atrium), sinus bradycardia (slow heartbeat), supraventricular ventricular tachycardia (VT originating outside of the ventricles, or SVT), heart block (delayed normal flow of electrical impulses), premature ventricular contractions, and idioventricular rhythms (slow, regular rhythms without coordination between the atria and ventricles). To maximize safety in the event the electrodes were misapplied, asystole (no electrical activity) should be detected and not shocked with >95% specificity. See, e.g., Kerber, et al., "Automatic external defibrillators for public access defibrillation: recommendations for specifying and reporting arrhythmia analysis algorithm performance, incorporating new waveforms, and enhancing safety", *Circ,* 95:1677–1682, 1997.

Historically, arrhythmia detection has been performed using empirical methodology. For example, the Heartstream Forerunner manufactured by Philips Corporation, an exemplary prior art AED, uses a set of four indicators relating to ECG waveform shape and timing to provide the advisory function. These indicators are (i) rate, (ii) narrowness of the QRS complex, (iii) repeatability of QRS complexes, and (iv) amplitude. While such indicators are often sufficient to detect VF, ventricular and supraventricular tachycardia may not be always be easily distinguished. During typical AED usage outside the clinical environment, the patient is already unconscious, and SVT is very rarely presented. The Powerheart CRM, an automatic defibrillator manufactured by Cardiac Science, Inc., is used in the clinical setting. In an automatic defibrillator, the device automatically delivers a shock, rather than just providing an advisory to shock. For an automatic defibrillator, it is critical that SVT and pulsatile VT, during hemodynamic stability, be detected accurately and the patient not be shocked, as the patient may be conscious. Further, in the clinical environment, pulseless versus unstable ventricular tachycardias need to be distinguished, as pulseless VT is best treated with countershock, but unstable VT is best treated with synchronized cardioversion (a shock with lower energy level that is timed with the QRS complex). Accurate SVT and VT detection is difficult using empirical methodology since SVT and VT waveform shapes are highly variable. See, e.g., U.S. Pat. No. 6,480,734 entitled "Cardiac arrhythmia detector using ECG waveform-factor and its irregularity" issued Nov. 12, 2002, and U.S. Pat. No. 6,490,478 entitled "System and method for complexity analysis-based cardiac tachyarrhythmia detection" issued Dec. 3, 2002, both to Zhang, et al. and assigned to Cardiac Science.

Currently implemented AED and automatic defibrillator arrhythmia detection algorithms (such as those of the Philips and Cardiac Science approaches) are based on waveform time domain morphologies, with decision-making strategies based on absolute threshold criteria. These empirical methodologies decrease the sensitivity for detecting rhythms such as rapid ventricular tacchycardia.

Another prior art approach attempts to capitalize on the root reason for performing defibrillator arrhythmia analysis; i.e., to determine if insufficient cardiac output is present to warrant countershock therapy. See, e.g., Johnson, et al., "The transthoracic impedance cardiogram is a potential haemodynamic sensor for an automated external defibrillator," *Eur Heart J,* 19:1879–1888, 1998 (hereinafter "Johnson"). The Johnson approach uses the impedance cardiogram as a hemodynamic sensor for AEDs. However, their approach is flawed in that, inter alia, it fails to consider or account for the effects of electrode configuration on the electric field distributions and hence the resolution of significant ICG waveform features. Specifically, the Johnson apparatus utilizes a single electrode configuration, which significantly decreases B and X point resolution. B and X point resolution were further degraded by ensemble averaging of dZ/dt, with respect to the R point.

Further, Johnson employs manually selected beats and dZ/dt features, which is at best cumbersome. Also, the dZ/dt features chosen in Johnson to classify shockable rhythms are based on the C point amplitude, $dZ/dt_{MAX}$. This method is less than optimal, since C point amplitude has been demonstrated to be highly variable on a beat basis in both normal and cardiac subjects, due to respiration-synchronous fluctuations and other physiological factors. For example, in congestive heart failure (CHF) patients, standard deviations of greater than 100% have been demonstrated by the Assignee hereof. Thus, C point-related features are prone to significantly more physiologic variability than those associated with the B and X points. With such C point-related features, only 80% of the nonshockable rhythms (20/25) could be classified, well below the AHA recommendation of 95% specificity. Hence, under the prior art approach of Johnson (and others), a significant number of patients not requiring shocking are erroneously shocked or not shocked due to misclassification and related inaccuracies. Erroneous shocks can lead to severe burns, while failure to shock during fibrillation leads to death.

Based on the foregoing, there is a need for an improved apparatus and method for determining the need for, and applying, defibrillating current to a subject. Such improved apparatus and method ideally would provide the user with an accurate advisory of the need for shock, and be capable of automatic application of the shock when needed without further user intervention if so selected. This capability would permit users of literally any skill and training level to accurately and properly treat subjects displaying a variety of different cardiac conditions, such treatment including discrimination of those situations where shock is or is not required.

SUMMARY OF THE INVENTION

The present invention satisfies the aforementioned needs by providing an improved method and apparatus for measuring the cardiac output of a living subject.

In a first aspect of the invention, an improved apparatus for measuring the cardiac output of a living subject is disclosed. In one exemplary embodiment, the living subject is a human being, and the apparatus comprises a system having a plurality of electrode pairs, a constant current source, a plurality of electrical leads connecting the constant current source with the plurality of electrode pairs, a differential amplifier for measuring the differential voltage at the electrodes, and circuitry for measuring ECG potentials from the electrode pairs. A predetermined distance is maintained between each of the individual electrodes in each electrode pair, thereby mitigating error sources relating to the relative placement of individual electrodes from the cardiac output measurement. Cardiac stroke volume is measured using the aforementioned apparatus by applying a constant current to the stimulation electrodes, measuring the resulting voltage differential at the measurement electrodes, and determining the stroke volume from the measured voltage and a predetermined relationship describing intra-thoracic impedance. The system also measures cardiac rate via the ECG potentials at the electrodes; cardiac output is then determined using the measured cardiac stroke volume and cardiac rate from the ECG potential.

In a second aspect of the invention, an improved cardiac output electrode assembly is disclosed. In one exemplary embodiment, the electrode assembly comprises a pair of electrode terminals disposed a predetermined distance from one another within an insulating substrate using a "snap" arrangement and electrolytic gel interposed between the electrode and skin of the subject. The substrate and gel materials of the electrode assembly are advantageously selected so as to provide a uniform and firm physical contact of the gel (and accordingly the electrode terminals) with the skin of the patient, and position of the terminals with relation to one another. The predetermined spacing of the electrodes also facilitates the detection of discontinuities in the system (such as an electrode becoming disconnected from the patient) through the measurement and comparison of impedance waveforms obtained from various electrode terminals. Additionally, the electrode pairs are used in conjunction with connectors having opposable jaws adapted such that no downward or normal pressure need be applied when a connector is fastened to an electrode terminal, yet consistent electrical properties are maintained.

In a third aspect of the invention, an improved method of measuring the cardiac output of a living subject is disclosed. The method generally comprises providing a plurality of electrode pairs; positioning the electrode pairs at predetermined locations above and below the thoracic cavity, generating a constant current; applying the constant current to one electrode of each of the electrode pairs; measuring the voltage at the second electrode of each electrode pair; determining cardiac stroke volume from the measured voltage; and determining cardiac output based on stroke volume and cardiac rate. In one exemplary embodiment, four electrode pairs are utilized, each having a predetermined spacing between both of the individual electrodes of the pair. The electrode pairs are placed at locations above and below the thoracic cavity of the subject, on both the right and left sides. Both differential voltage (related to the time-variant component of total thoracic impedance) and cardiac rate are measured via the electrode pairs for both sides of the subject.

In a fourth aspect of the invention, an improved method of monitoring the electrical continuity of a plurality of electrodes in an impedance cardiography system is disclosed. In one exemplary embodiment, the method comprises providing a plurality of electrically conductive terminals; disposing the terminals in relation to the thoracic cavity of a subject; generating a current between a first terminal and a second terminal, the current passing through at least a portion of the thoracic cavity; measuring an impedance waveform from the second terminal; and comparing the measured impedance waveform to a similar waveform measured from another terminal, the difference between the impedance waveforms being used to evaluate the electrical continuity of the first terminal.

In a fifth aspect of the invention, an improved impedance cardiography module adapted to implement various of the foregoing aspects is disclosed. The module comprises a plurality of interfaces adapted to receive signals such as impedance and ECG waveforms; determinations of cardiac output and other related parameters are output via another interface to a host or monitoring device. In one exemplary embodiment, the module of the present invention comprises a digital processor-based device adapted to process impedance and other signals derived from one or more living subjects, and output signals to the monitor/display unit according to an established communications protocol. A microprocessor/DSP architecture is used in conjunction with signal filtration, analog-to-digital conversion, and other signal conditioning/processing within the module to extract useful cardiographic information from the patient signals received via the interfaces, and communicate this information to the monitor/display unit or other output device under control of the microprocessor. Other inputs such as the subject's blood pressure, multiple ECG waveforms, and the like may be utilized by the module during the aforementioned CO determination. The module may further be configured to generate the stimulation signal (e.g., constant current previously described) which is provided to the patient electrodes. In another embodiment, the module is further configured for impedance cardiographic and electrocardiographic waveform fiducial point detection and analysis using discrete wavelet transforms.

In yet another embodiment, the module includes a network interface adapted to couple the module to a data network capable of distributing the data generated by the module and other devices to local and/or remote network nodes, such as local stations within a health care facility, or to a remote health care or medical facility in the case of outpatient applications. Communication with other network nodes, locations, or personal electronic devices is accomplished using, for example, modulator/demodulator (modem) apparatus, wireless interface such as Bluetooth™, local- or wide-area network (LAN/WAN) topologies, circuit or packet-switched high-bandwidth data networks (such as asynchronous transfer mode), internet, intranet, the Wireless Medical Telemetry Service (WMTS) medical band (608–614 MHz), synchronous optical networks (SONET), FDDI, or even satellite communications.

In yet another embodiment, the ICG module of the invention comprises a yoke adapted to interface with a fixed or mobile electrocardiograph system via a flexible coupling. The yoke is highly mobile and is adapted to electrically interface with the leads attached to the subject, as well as with the host monitor. In one embodiment, the yoke further includes indications of the operating status of the yoke, as well as other data interfaces for transmitting ICG data to, and receiving other types of data (such as blood pressure data) from, other processing modules. In another embodiment, the yoke comprises a wireless data interface (such as Bluetooth™ or IEEE Std. 802.11 WLAN interface) between the yoke and the monitor. In yet another embodiment, the yoke is provided with a wireless interface between itself and the patient electrodes.

In yet another embodiment, the ICG module apparatus is configured to operate in conjunction with a dialysis (e.g., hemodialysis) system. Because cardiovascular events account for over 50% of deaths in dialysis patients per year in the United States, more vigilant cardiovascular disease management, including hemodynamic monitoring through impedance cardiography, may increase the survival rate of this patient population. The ICG module is adapted to receive data such as patient blood pressure from the dialyzer or one of the dialyzer's modules, which may operate contemporaneously with the ICG module while the patient is being dialyzed and monitored.

In yet another embodiment, the improved ICG module of the invention comprises a card or board level plug-in module adapted for receipt within a host device such as a personal computer or dedicated monitor/display unit.

In a sixth aspect of the invention, an improved method of waveform selection for input to the module processing is disclosed. In one exemplary embodiment, the input waveforms comprise ECG waveforms used in the CO determination, and the method comprises evaluating each waveform for signal quality based upon at least one parameter; ranking each waveform based on the foregoing quality evaluation; and selecting the one waveform with the best rank for further processing. The Q and R fiducial points are used to determine the quality evaluation parameters, which may include for example R-wave amplitude, QR interval difference, and RR interval difference. In this fashion, the module of the present invention evaluates the various sources of input data, and selects the best one from the available signals for further signal processing.

In a seventh aspect of the invention, an improved software environment adapted for use with the aforementioned ICG module is disclosed. In one exemplary embodiment, the software environment comprises initialization, operating, and processing modules adapted to perform various start-up, signal processing, communication, and error detection functions within the module.

In an eighth aspect of the invention, an improved defibrillator apparatus is disclosed, and generally comprises apparatus adapted for evaluating the need for applying defibrillation energy to a living subject based on impedance waveforms. In one exemplary embodiment, the evaluation is based at least in part on the variation in B and X fiducial points within successive cardiographic impedance waveforms obtained from the subject, with the variation being measured using standard deviation (STD).

In another embodiment, the evaluation is based at least in part on forming a time-scale domain representation of the impedance data obtained from said subject.

In yet another embodiment, the evaluation is based at least in part on identifying pacing spikes within electrocardiographic data obtained from said subject.

In yet another embodiment, the evaluation is performed at least in part by fuzzy decision logic as applied to the impedance cardiography waveforms obtained from said subject.

In still another embodiment, the evaluation is performed at least in part by detecting QRS complexes within the waveforms without use of an absolute threshold.

In yet another embodiment the evaluation comprises processing ICG and ECG signals to identify artifacts therein, the processing using said artifacts to generate a shock scale upon which at least in part determines whether the energy will be applied.

In still another embodiment, the apparatus is adapted to receive ICG and ECG signals derived from the subject and process at least a portion of the signals in the time-scale domain, the processing further comprising generating a high-accuracy shock advisory.

In a ninth aspect of the invention, an improved processing module adapted for use with a defibrillator is disclosed. The module generally comprises first processing apparatus adapted for processing ECG signals from a living subject; second processing apparatus operatively coupled to the first processing apparatus and adapted for processing ICG signals from the subject; and decision logic operatively coupled to the second processing apparatus and adapted to determine whether defibrillation energy should be applied to the subject based at least in part on the processing of the ICG signals.

In a tenth aspect of the invention, an improved method of artifact detection within a physiologic waveform is disclosed. The method generally comprises: detecting a first feature within the waveform; identifying a location within the first feature; and identifying a local maximum relative to the location, the local maximum comprising the artifact. In one exemplary embodiment, the waveform comprises an ECG, the first feature a QRS complex, and the artifact an R point disposed therein. The identification of the location within the QRS complex is conducted in the time-scale domain, with this location providing the basis for a "window" within which the local maximum is identified, the local maximum being designated as the R point.

In an eleventh aspect of the invention, an improved method of evaluating whether to apply defibrillating shock to a subject is disclosed, generally comprising: obtaining waveforms from the subject; detecting beats within the waveforms; based at least in part on the detecting, detecting a plurality of fiducial points within the waveforms; processing the fiducial points to generate at least one parameter relating to the cardiac function of the subject; and evaluating whether to apply the defibrillating shock based at least in part on at least one parameter.

In a twelfth aspect of the invention, an improved method of substantially avoiding the application of unnecessary defibrillation shocks to a living subject is disclosed, the method generally comprising: obtaining impedance waveforms from the subject; accurately determining cardiac output using at least the waveforms; and correlating the cardiac output determination to physiologic conditions not requiring defibrillation. In one exemplary embodiment, the method comprises using one or more of the foregoing features (e.g., predetermined electrode spacing, pacing spike-based parsing, time-scale domain processing, and fuzzy logic decision process) to provide a highly accurate analysis of cardiac function which avoids misclassification of non-shockable rhythms as shockable, thereby avoiding the unnecessary and potentially detrimental application of defibrillation energy.

In a thirteenth aspect of the invention, an improved method of treating a living subject is disclosed, the method generally comprising: obtaining impedance and electrocardiographic waveforms from the subject; analyzing the waveforms to determine whether the subject exhibits shockable or non-shockable rhythms, the act of analyzing comprising determining the cardiac output of the subject using a plurality of fiducial points; and, where shockable rhythms are present, administering defibrillating energy to the subject.

In a fourteenth aspect of the invention, improved defibrillator electrode apparatus, is disclosed, generally comprising: a first electrode for delivering defibrillation energy to a living subject; and a second electrode means for delivering ICG stimulation current and sensing impedance waveforms the subject. In one exemplary embodiment, the defibrillation and ICG electrodes are integrated into substantially unitary structures, thereby facilitating easy application of all electrodes to the subject concurrently by the operator.

BRIEF DESCRIPTION OF THE DRAWINGS

FIG. 3a is a plane view of a typical human thorax illustrating an exemplary placement of the electrode arrays of the present invention during cardiac output measurement.

FIG. 3b is a schematic diagram illustrating the measurement of cardiac output using the electrode arrays and current source of the present invention.

FIG. 7a is an assembly diagram illustrating the construction of a first embodiment of the electrode array of the present invention.

FIG. 7b is a cross-sectional view detailing the shape of the electrode terminals of the electrode array of FIG. 7a, and the construction thereof.

FIG. 7c illustrates top and bottom perspective views of the electrode array of FIG. 7a when fully assembled.

FIG. 7d is a perspective view of a second embodiment of the electrode array of the invention.

FIG. 8 is a perspective view of a third embodiment of the electrode array of the invention.

FIG. 13a is a graphical representation of the impedance signal extraction process performed by the ICG module of the present invention.

FIGS. 17a–c are top, rear, and front plan views, respectively, of the module of FIGS. 12–14, configured as a yoke adapted for mobility and electrical interface with a monitoring device.

FIG. 24b is logical flow diagram of one exemplary embodiment of the method of FIG. 24a.

DETAILED DESCRIPTION OF THE INVENTION

Figure 1:
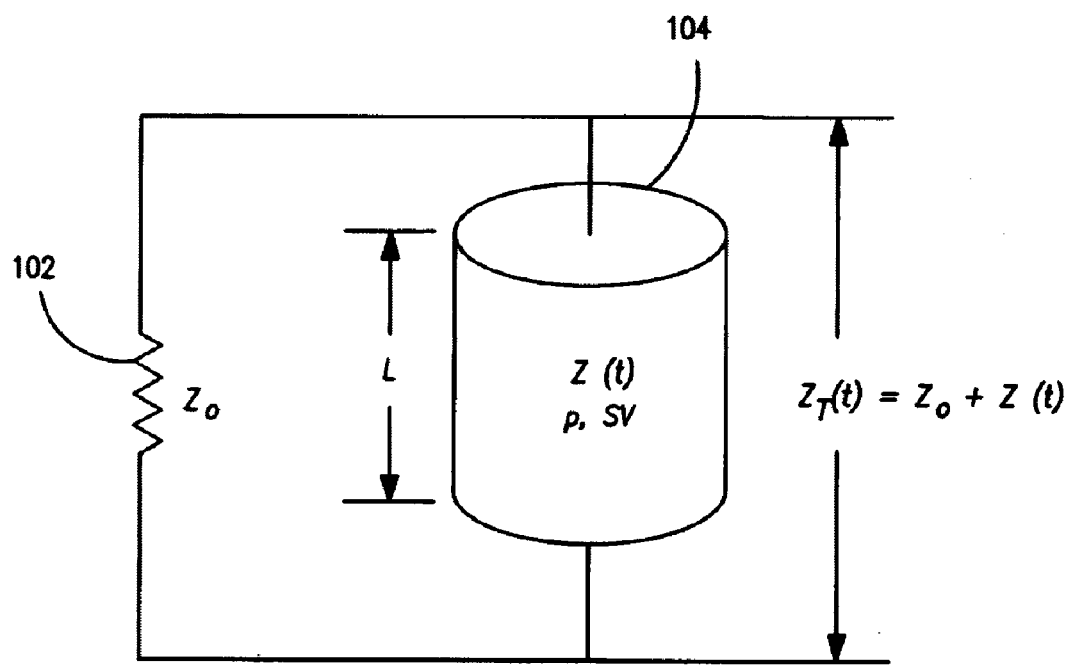
FIG. 1 is schematic diagram illustrating the parallel column model of the impedance of the thoracic cavity of a human being.
Figure 2A:
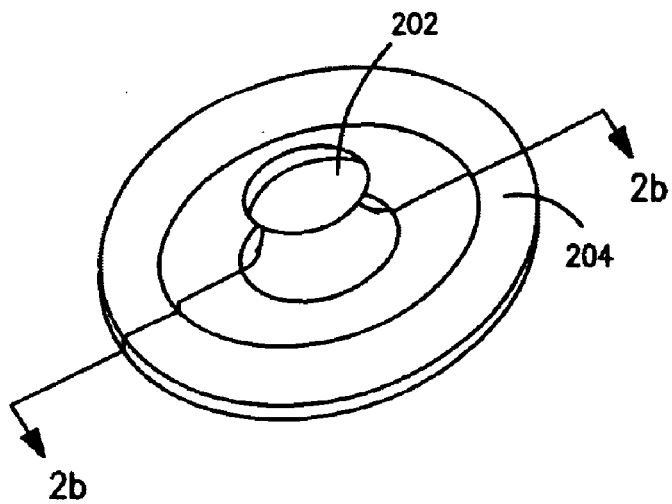
FIGS. 2a and 2b are perspective and cross-sectional views, respectively, of a prior art impedance cardiography electrode assembly.
Figure 2B:
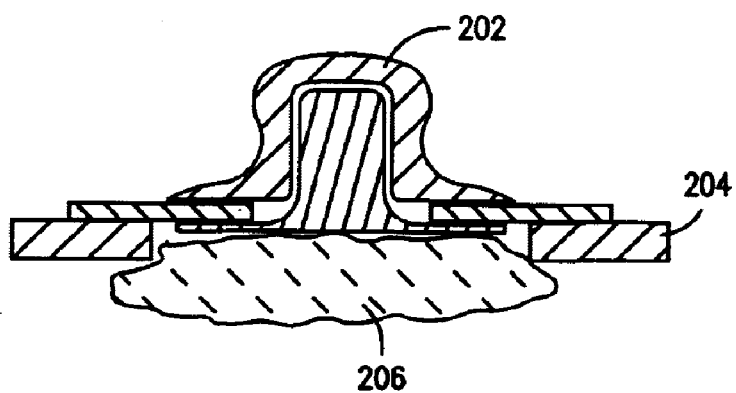

Reference is now made to the drawings wherein like numerals refer to like parts throughout.

It is noted that while the invention is described herein in terms of an apparatus and method for determining cardiac output suitable for use on the thorax of a human subject, the invention may also conceivably be embodied or adapted to monitor cardiac output at other locations on the human body, as well as monitoring cardiac output on other warm-blooded species. All such adaptations and alternate embodiments are considered to fall within the scope of the claims appended hereto.

As used herein, the term "digital processor" is meant generally to include all types of digital processing devices including, without limitation, digital signal processors (DSPs), reduced instruction set computers (RISC), general-purpose (CISC) processors, microprocessors, and application-specific integrated circuits (ASICs). Such digital processors may be contained on a single unitary IC die, or distributed across multiple components.

As used herein, the terms "monitor" and "monitoring device" are used generally to refer to devices adapted to perform monitoring, display, user interface, and/or control functions. Such devices may be dedicated to a particular function, or multi-purpose devices adaptable to performing a variety of functions and/or interfacing with a number of functional modules.

As used herein, the terms "shock", "countershock", "defibrillation", "defibrillating energy" and "defibrillating current" are used interchangeably to refer to the process of applying electrical potential or current to the tissue of a subject in order to induce a desired response from that tissue, such as for example re-acquisition of normal synchronized excitations of the cardiac tissue.

Methodology

Referring now to FIGS. 3a-5, the general methodology of measuring cardiac output in a living subject according to the invention is described.

As previously discussed, the thoracic impedance $Z_T(t)$ of a living subject may be modeled as comprising a constant impedance, $Z_o$, and time-varying impedance, $\Delta Z$ (t). According to the well-known "parallel-column" model of the thorax, this change in thoracic impedance, $\Delta Z$ (t), is related to the pulsatile blood volume change. In this model, illustrated in the form of a schematic diagram in FIG. 1 herein, effectively constant tissue impedances such as bone, muscle, and fat are modeled as a conducting volume $Z_o$ 102 in parallel with the pulsatile impedance of the blood $\Delta Z$ (t) 104. This second impedance 104 is a time-varying fluid column with resistivity, ρ, cylindrical length, L, and a time-varying cross-sectional area that oscillates between zero and a value A, the latter which correlates to the stroke volume V. When the pulsatile volume is at a minimum in the cardiac cycle, all the conducting tissues and fluids are represented by $Z_o$. During the cardiac cycle, the cylinder cross-sectional area increases from zero until the cylinder's volume equals the blood volume change.

Figure 4:
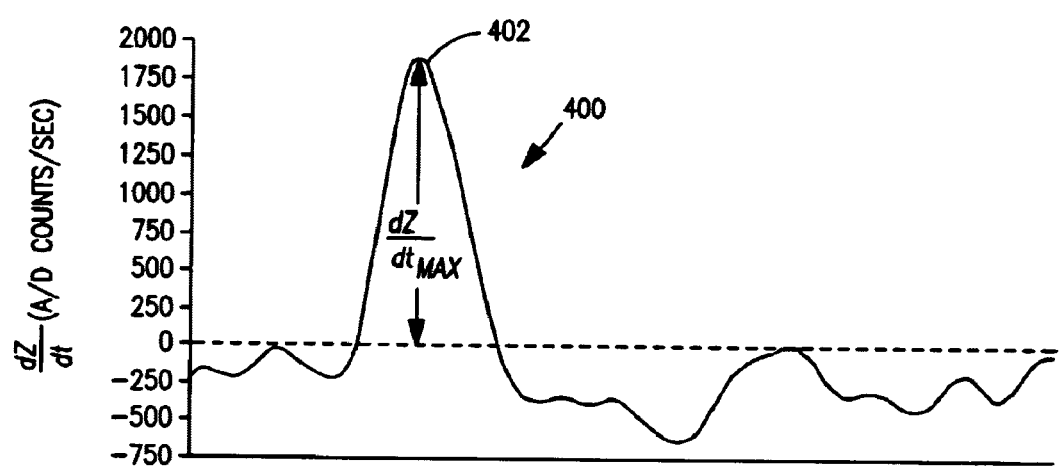
FIG. 4 is graph of the derivative of the time-variant component $\Delta Z$ (t) of thoracic impedance as a function of time, illustrating the systole "peak" used in determining ventricular ejection time (VET).

Because $Z_o$ is much greater than $\Delta Z(t)$, the relationship of Eqn. (2) holds:

$$SV = \rho \left(\frac{L^2}{Z_0^2}\right) VET \left(\frac{dZ(t)}{dt}\right)_{min}, \quad (2)$$

where L is the distance between the measurement electrodes in cm (FIG. 3a), VET is the ventricular ejection time in seconds, and $$\left(\frac{dZ(t)}{dt}\right)_{min}$$

is the magnitude of the largest negative derivative of the impedance change occurring during systole in ohms/s. Often, the impedance derivative 400 is purposely inverted as shown in FIG. 4 so that the original negative minimum change will appear as a positive maximum 402, $$\left(\frac{dZ(t)}{dt}\right)_{max},$$

in a manner more familiar to clinicians.

The ventricular ejection time (VET) is estimated from features in the impedance waveform, which is obtained from the measurement terminals of the electrode arrays 302, 304, 306, 308 placed on various locations of the subject's thorax as illustrated in FIGS. 3a and 3b. In the present embodiment, a value of 150 ohm-cm is used for the resistivity of the blood, although it will be recognized that other values may be substituted as appropriate.

It is noted that the description of the volume of participating tissue may be modified. Rather than model the thorax as a cylinder as shown in FIG. 1 above, the thorax may instead be modeled as a truncated cone (as first described by Sramek and Bernstein). This approach results in a modified stroke volume calculation as in Eqn. (3):

$$SV = \frac{L^3}{4.25 Z_0} VET \left(\frac{dZ(t)}{dt}\right)_{min}. \quad (3)$$

With either of the two aforementioned approaches (i.e., cylindrical or truncated cone), the pulsatile impedance is estimated using Ohm's law, which is well known in the electrical arts. Specifically, current from a constant current source, $I_T(t)$, is applied, and the resulting voltage, $V_T(t)$, is measured in order to calculate the ratio of Eqn. (4):

$$Z_T(t) = \frac{V_T(t)}{I_T(t)}. \quad (4)$$

In the selected frequency range (i.e., 68 kHz), the typical impedance associated with a human subject's skin is 2 to 10 times the value of the underlying thoracic impedance $Z_T(t)$. To aid in eliminating the contribution from skin and tissue impedance, the present invention uses at least two, and typically four electrode arrays 302, 304, 306, 308 for measurement, as shown in FIG. 3a. The physical construction and these electrode arrays is described in detail with reference to FIGS. 7a–8 herein.

In a simple application, one electrode array 302 comprising a stimulation electrode terminal 310 and a measurement electrode terminal 312 is applied above the thorax 300 of the subject, while a second electrode array 304 (having stimulation electrode terminal 314 and measurement electrode terminal 316) is applied below the thorax 300. The AC current from the current source is supplied to the stimulation electrode terminals 310, 314. As shown in FIG. 3b, current flows from each stimulation electrode terminal 310, 314 through each constant skin impedance, $Z_{sk1}$ or $Z_{sk4}$, each constant body tissue impedance, $Z_{b1}$ or $Z_{b1}$, and each constant skin impedance, $Z_{sk2}$ or $Z_{sk3}$, to each measurement electrode terminal 312, 316. The voltages at the measurement electrode terminals 312, 316 are measured and input to a differential amplifier to obtain the differential voltage, $V_T(t)$. The desired thoracic impedance, $Z_T(t)$, is then obtained using the relationship of Eqn. (4).

As shown in FIG. 3a, two sets of electrode arrays may advantageously be used to monitor the impedance associated with the left and right portion of the thorax 300 in the present invention. When eight electrode terminals (four arrays 302, 304, 306, 308) are used in this manner, the four measurement arrays are also used to obtain an electrocardiogram, based on one of four vectors modified from Lead I, II, III, or IV. The resulting electrocardiograms are based on the original Lead configurations, but are not of diagnostic quality. Regardless of the modified Lead configuration used, the Q wave of the ECG QRS interval is used to determine the heart rate and to trigger measurements of VET within the $$\frac{dZ(t)}{dt}$$

waveform.

Figure 5:
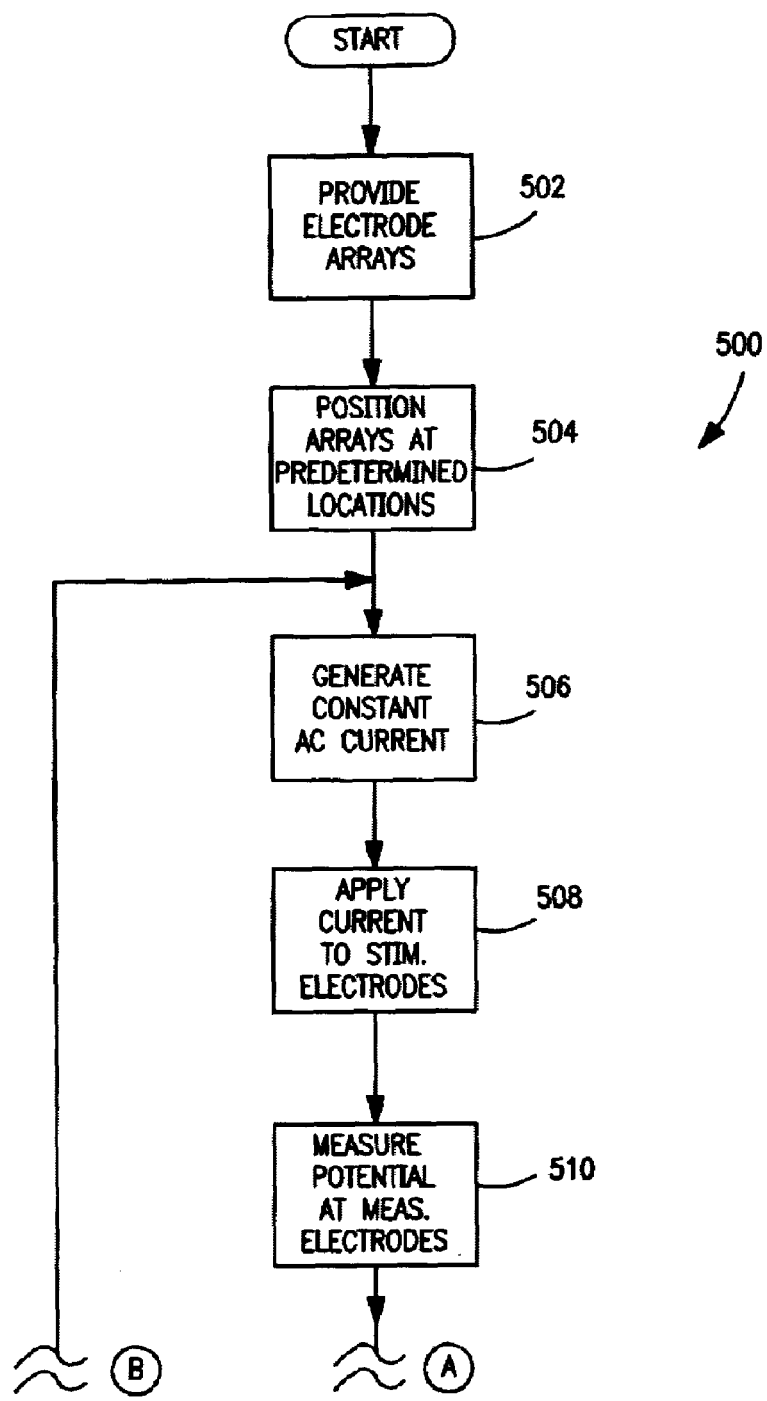
FIG. 5 is a logical flow diagram illustrating one exemplary embodiment of the method of measuring cardiac output within a living subject according to the invention.
Figure 5:
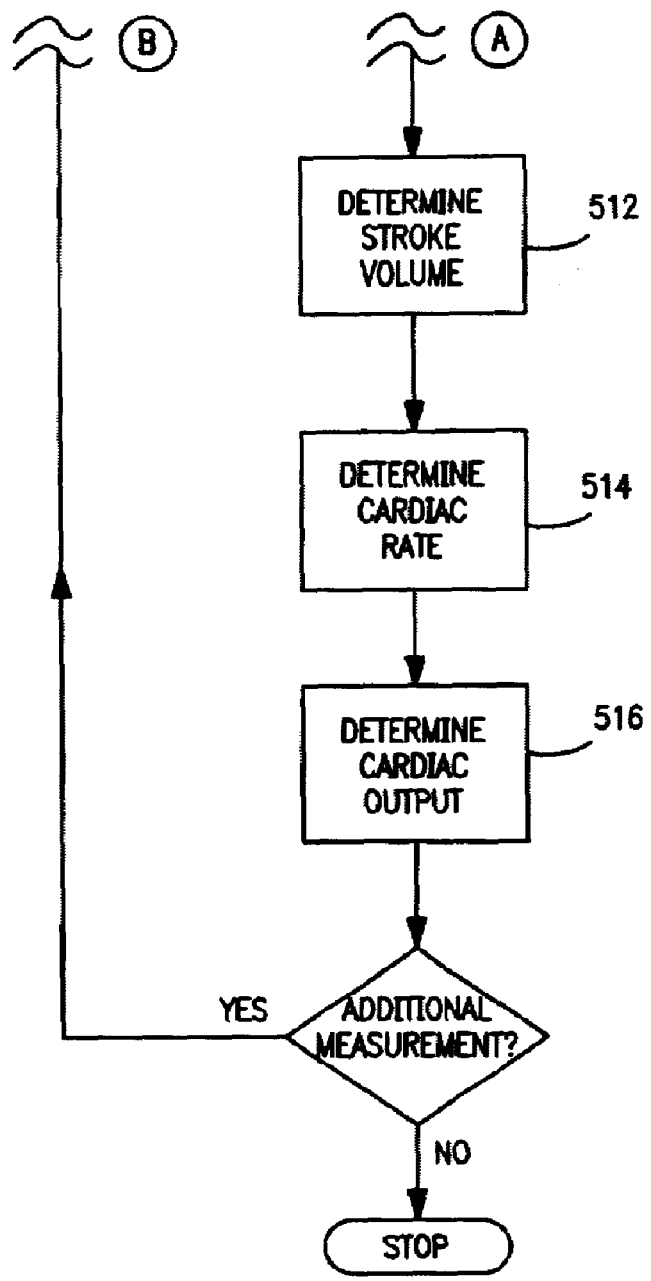

FIG. 5 illustrates the logical flow of the method of measuring cardiac output according to the invention. As shown in FIG. 5, the method 500 generally comprises first providing a plurality of electrode "arrays" of the type previously described herein per step 502. The electrode arrays are positioned at predetermined locations above and below the thoracic cavity per step 504, as illustrated in FIG. 3a herein. In one embodiment of the method, these locations are chosen to be on the right and left sides of the abdomen of the subject, and the right and left sides of the neck. These locations, with prior art band electrodes, were first used by Kubicek. Other locations and/or combinations of arrays may be substituted with equal success.

Next, a substantially constant AC current is generated in step 506, and the current applied to the stimulation electrode terminal 310, 314 of each of the electrode arrays in step 508. The voltage generated at the measurement electrode terminal 312, 316 of each electrode array is next measured in step 510. As previously discussed, this voltage is generally reduced from that applied to the stimulation electrode by virtue of the impedance of, inter alia, the thoracic cavity. Note that the measured voltage may be absolute, or relative (i.e., a differential voltage) as desired. Next, in step 512, the cardiac stroke volume from the measured voltage, using for example the relationship of Eqn. (3) above. Cardiac rate (step 514) is also determined by using the measurement electrodes to sense the ECG potentials generated by the heart of the subject. Lastly, in step 516, cardiac output is determined based on the stroke volume determined in step 512 and the cardiac rate in step 514 using the relationship of Eqn. 1 above.

Apparatus

Figure 6:
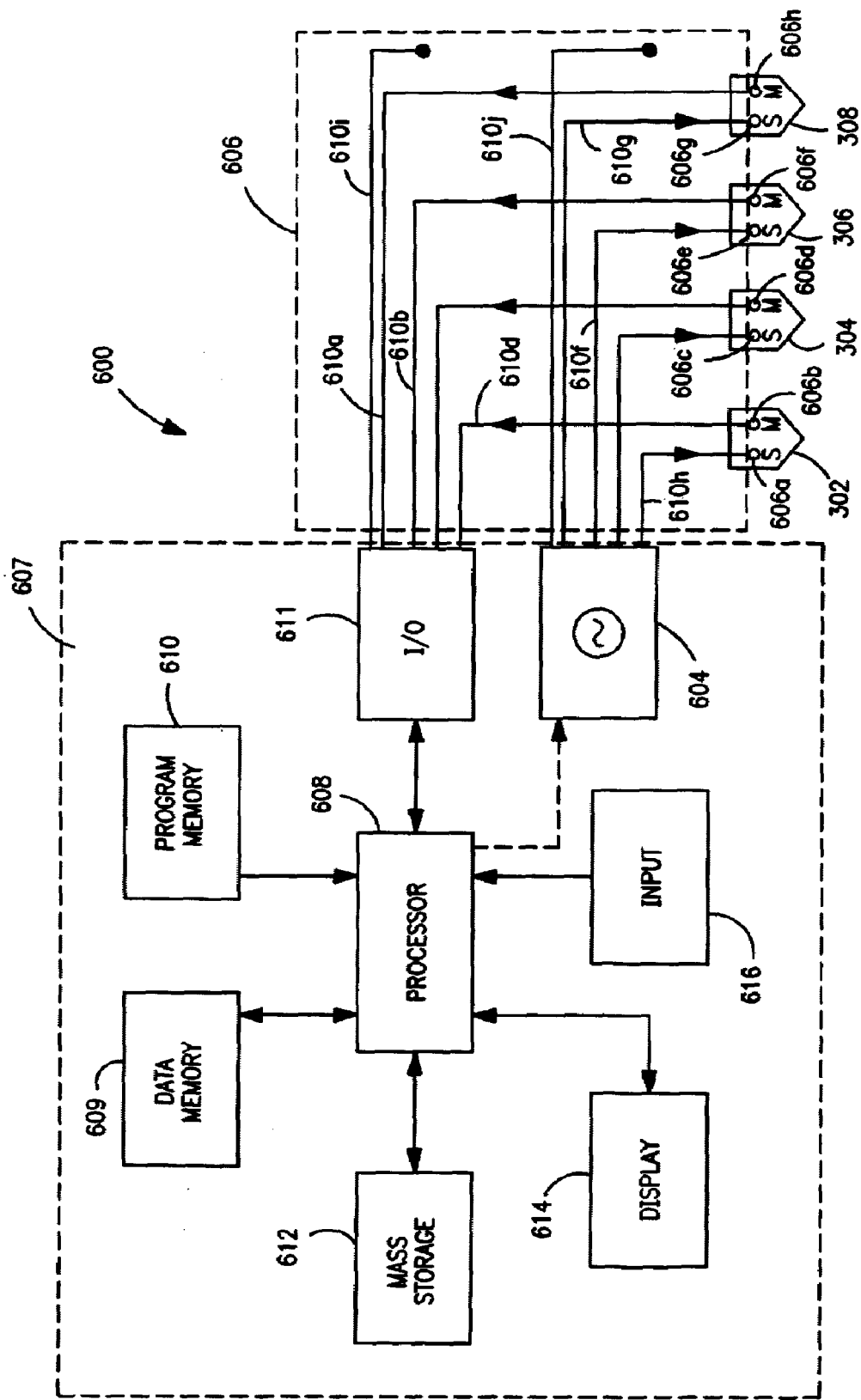
FIG. 6 is a logical block diagram illustrating one exemplary embodiment of the cardiac output measurement system of the present invention.

Referring now to FIG. 6, a first embodiment of the apparatus for measuring cardiac output using the above-described technique is disclosed. In addition to the four electrode arrays 302, 304, 306, 308 previously discussed, the system 600 generally comprises an alternating current (AC) current source 604 capable of generating a substantially constant current, a plurality of electrical leads in the form of a multi-ended lead assembly 606 for connecting the instrument monitor 607 to the individual terminals of the electrode arrays 302, 304, 306, 308, a processor 608 with associated algorithms capable of running thereon for performing analysis of the signals measured from the measurement terminals, data and program memory 609, 610 in data communication with the processor 608 for storing and retrieving program instructions and data; an I/O interface 611 (including analog-to-digital converter) for interfacing data between the measurement electrodes and the processor 608; a mass storage device 612 in data communication with the processor for storing and retrieving data; a display device 614 (with associated display driver, not shown) for providing an output display to the system operator, and an input device 616 for receiving input from the operator. It will be recognized that the processor 608, memory 609, 610, I/O interface 611, mass storage device 612, display device 614, and input device 616 (collectively comprising the instrument monitor 607) may be embodied in any variety of forms, such as a personal computer (PC), hand-held computer, or other computing device. The construction and operation of such devices is well known in the art, and accordingly is not described further herein.

The applied current derived from the current source 604 is a 70 kHz sine wave of approximately 2.5 mA peak-to-peak. The measured voltage associated with the aforementioned sine wave is on the order of 75 mV peak-to-peak. These values are chosen to advantageously minimize electric shock hazard, although it will be appreciated that other frequencies, currents, or voltages may be substituted. The construction and operation of AC current sources is well known in the electronic arts, and accordingly is not described further herein.

The electrode lead assembly 606 of the illustrated embodiment contains a ten wire assembly (two wires are left unused) that branches to eight individual connectors 606a–h. The conductors 610a–h of the lead assembly are fashioned from electrically conductive material such as copper or aluminum, and are insulated using a polymer-based insulation having the desired dielectric strength as is well known in the electrical arts. The length of the conductors may also be controlled so as to match the impedance of each individual conductor to that of the others within the assembly 606.

Using one of four modified lead configurations, the body surface potential is measured between two measurement electrodes. This time-varying voltage reflects the electrical activity of the heart, and contains one QRS interval per cardiac cycle. The biopotential is analyzed to identify each QRS complex. The frequency of QRS complexes determines the heart rate. The Q wave within the QRS complex is then used to trigger identification of VET within the $$\frac{dZ(t)}{dt}$$

waveform, as the opening of the aortic valve (the beginning of VET) occurs after the appearance of the Q wave.

Additional embodiments of the cardiac output measurement apparatus of the invention are described subsequently herein with respect to FIGS. 11–22.

Referring now to FIGS. 7a–7c, the electrode arrays 302, 304, 306, 308 of the invention are described in detail. As illustrated in FIG. 7a, each array comprises a flexible substrate 704 having a plurality of apertures 706, 708 formed therein. In the illustrated embodiment, two terminals 310, 312 are disposed through the apertures such that the top portions 716, 718 of the terminals project above the plane of the substrate 704. The two terminals 310, 312 comprise a stimulation terminal 310 and measurement terminal 312 as previously described with respect to FIG. 3a. The stimulation terminal 310 is used to apply the potential necessary to generate the current flowing through the thoracic cavity of the subject. It will be noted that despite designation of one terminal as a "stimulation terminal" and one as a "measurement" terminal, the role of these terminals may be reversed if desired, since they are functionally and physically identical but for the potential applied thereto (or measured therefrom). It is noted that the asymmetric shape of the substrate 704 of the embodiment of FIGS. 7a–7c may be used to assist the clinician in rapidly determining which electrode is the stimulation electrode and which the measurement electrode, such as by assigning a convention that the end of the array having a given shape always contains the stimulation electrode. Additionally, the substrate may be shaped to adapt to certain physical features of the patient, such as by using a substrate having a broader width so as to better conform to the generally cylindrical shape of the subject's neck. Any number of different substrate shapes may be employed; FIG. 7d illustrates one such alternative shape.

As shown in FIGS. 7a–7c, the terminals 310, 312 are firmly held in place within the substrate 704 at a predetermined distance 705 by a mounting element 707 or any one of a variety of other constructions as will be described in greater detail below. The distance (measured centerline-to-centerline on the terminals 310, 312) is approximately 5 cm in the embodiment of FIG. 7a, although it will be recognized that other distances may be substituted. Desired distances may be determined through experimentation, anecdotal observations, calculations, or any other suitable method; however, experimental evidence obtained by the Applicant herein indicates that a distance of 5 cm is optimal for impedance cardiography measurements.

The substrate 704 in the embodiment of FIG. 7a is formed from a Polyethylene foam, although other materials such as cloth or vinyl may be substituted. The polyethylene foam is chosen for its compliance and flexibility, thereby allowing it to conform somewhat to the contours of the subject's anatomy, while still maintaining sufficient rigidity for maintaining the terminals 312, 314 in the desired position and orientation.

As shown in FIG. 7b, the terminals 310, 312 of each array comprise a generally cylindrical shaped sidewall portion 720 having a first diameter 722, and a top portion 724 having a second diameter 726, the second diameter 726 being greater than the first diameter 722 in order to assist in retaining a connector mated to the terminal 310, 312 as described in greater detail below. The outer wall 721 of the sidewall portion 720 is essentially vertical in orientation (i.e., parallel to the central axis 725 of the terminal 310, 312), while the top portion is progressively rounded as shown. The terminals may be manufactured from an extruded metal such nickel, with a coating of brass, or may be molded from carbon. Alternatively, the terminals may be molded of plastic, and coated with a metal such as gold or impregnated with carbon. The extruded metal possesses the advantage of low cost, while the molded plastic impregnated with carbon possesses the advantage of radiolucency. A terminal molded of plastic and coated with gold may possess low noise artifact.

The terminals 310, 312 of the electrode array comprise a two piece construction, having an upper terminal element 730 and a lower terminal element 732 as shown in FIGS. 7a and 7b. The post 734 of the lower terminal element 732 is adapted to be frictionally received within the cavity 736 of the upper terminal element when the two components are mated. In this fashion, the upper and lower elements 730, 732 form a single unit when assembled, with the mounting element 707 being frictionally held or "pinched" between the lower surface 740 of the upper element 730 and the upper surface 742 of the lower element 732. The post 734 of the lower element perforates the mounting element 707, or alternatively penetrates through a pre-existing aperture 738 formed therein. The lower elements 730, 732 of the electrode array terminals 310, 312 are coated with Ag/AgCl, although other materials with the desirable mechanical and electrochemical properties such as Zinc Chloride may be used if desired.

The electrolytic element 750 of each electrode array comprises an electrolytic gel of the type well known in the bio-electrical arts; in the present embodiment, the gel comprises an ultraviolet (UV) cured potassium chloride (KCl) gel, although it will be recognized that other types of compounds or materials may be used. UV curing of the gel allows the element 750 to have a more solidified consistency and improved mechanical properties, thereby preventing excessive spreading or thinning of the element when the array is applied to the subject while still maintaining its overall adhesiveness and electrolytic properties. As shown in FIGS. 7b and 7c, the element 750 is sized so as to encompass the edges 752 of the respective aperture 706, 708 in the substrate 704 over which it is placed when assembled, although other configurations may be used. The top portion 755 of the element 750 fits at least partially within the aperture 706, 708 and conforms substantially thereto, thereby effecting contact with the bottom surface 760 of the bottom terminal element 732. In this way, ions are passed between the skin of the subject and the terminals of the array via the gel element 750. The gel also provides for adhesion of the array to the skin of the subject, although the array of the present embodiment also includes a separate adhesive 762 which is applied to the bottom surface of the substrate 704, as shown in FIG. 7c.

Since the placement of the electrolytic element 750 with respect to the terminals 310, 312 of the array may in certain cases affect the ultimate measurements of cardiac output obtained with the system, the gel of the element 750 is advantageously placed in the embodiment of FIGS. 7a–c so as to be symmetric with respect to the terminal 310, 312. It will be recognized, however, that the element(s) 750 may also be placed so as to produce certain desired electrolytic conditions. Similarly, the element 750 may be split into two or more component parts if desired.

Furthermore, it is noted that while the embodiment of FIGS. 7a–c employs two fixed terminals that are effectively immovable within the substrate, means for allowing adjustment or change of the relative position of the terminals may be substituted. For example, as illustrated in FIG. 8, a terminal array having three terminal posts may be used, the second post 802 being spaced a first distance 804 from the first post 806, and the third post 810 being spaced a second distance 808 from the first post 806, such that the clinician can select one of two terminal spacings as desired.

Figure 9:
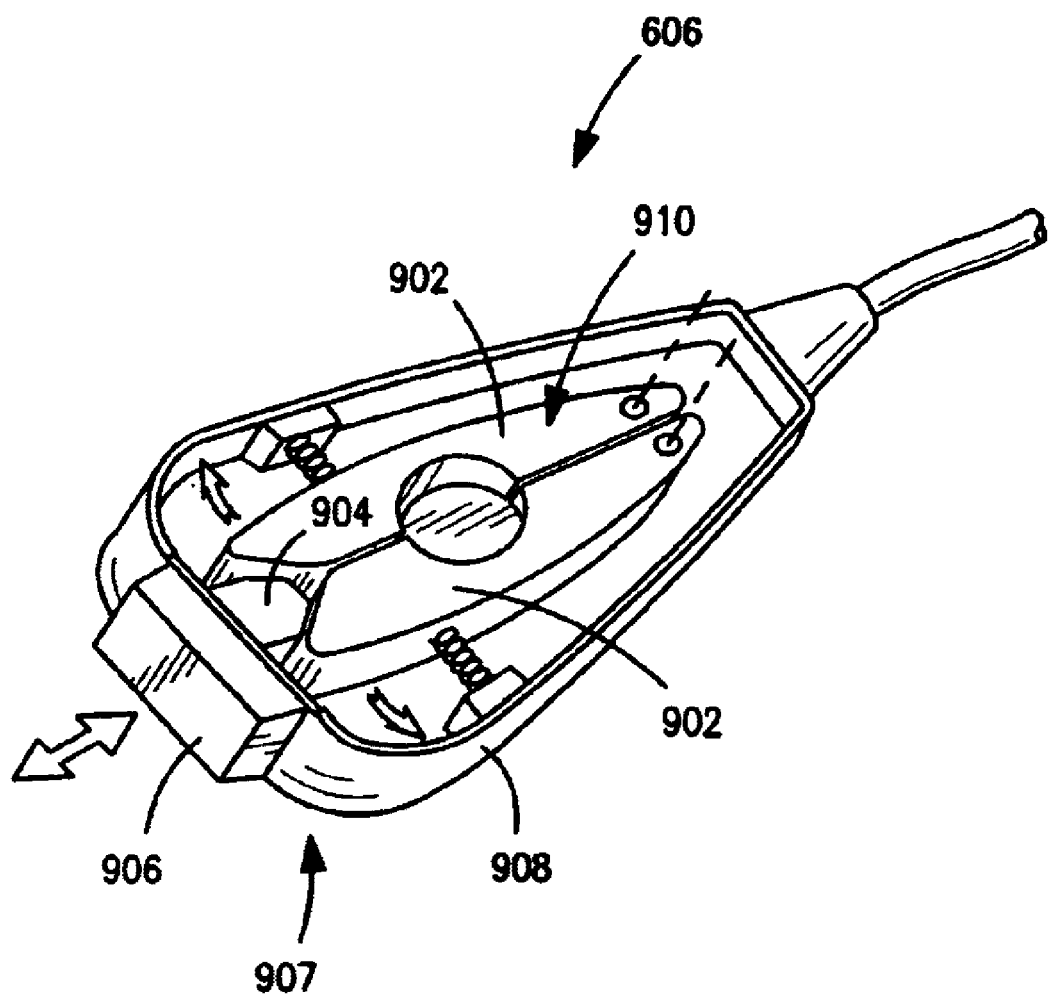
FIG. 9 is perspective view of one embodiment of a biased-jaw electrical connector as used in conjunction with the present invention.

As illustrated in FIG. 9, each electrode lead assembly connector 606a–h is designed to mitigate the downward force required to mate the connector with its respective electrode array terminal. Specifically, each connector 606a–h contains two spring-biased conductive jaws 902 that are spread apart by the cam surface 904 of an actuator button 906 disposed on the front 907 of the connector body 908. The connector jaws 902 and bias mechanism are designed to allow the upper and sidewall portions 724, 720 of the electrode terminal 310, 312 (FIG. 7b) to be received within the recess 910 of the jaws 902 when the button 906 is fully depressed. In this fashion, effectively no downward force is required to engage the connector to its respective terminal. The jaws 902 are contoured to engage substantially the entire surface of the sidewall portion 720 of the terminal when the actuator button 906 is released. Since the sidewall portion 720 of the terminal is effectively circular in cross-section, the connector may advantageously rotate around the axis of the terminal 310, 312 when lateral tension is applied to the conductor attached to that connector. U.S. Pat. No. 5,895,298 issued Apr. 20, 1999, entitled "DC Biopotential Electrode Connector and Connector Condition Sensor," and incorporated herein by reference in its entirety, describes a bias jaw electrical connector of the type referenced above in greater detail.

When used with the four two-terminal electrode arrays 302, 304, 306, 308 shown in FIG. 3a, each connector 606a–h is fastened to one of the two terminals 310, 312 of an electrode array. The 68 kHz constant current is applied from the current source to four electrode terminals (i.e., one terminal per array). Hence, complete circuits are formed between the current source and the I/O device 611 of the system 600 via the electrical conductors and connectors associated with the stimulation electrode terminals, the stimulation electrode terminals themselves, the thorax of the subject, the measurement terminals, and the electrical conductors and connectors associated with the measurement terminals.

Method of Evaluating Electrical Continuity

Figure 10:
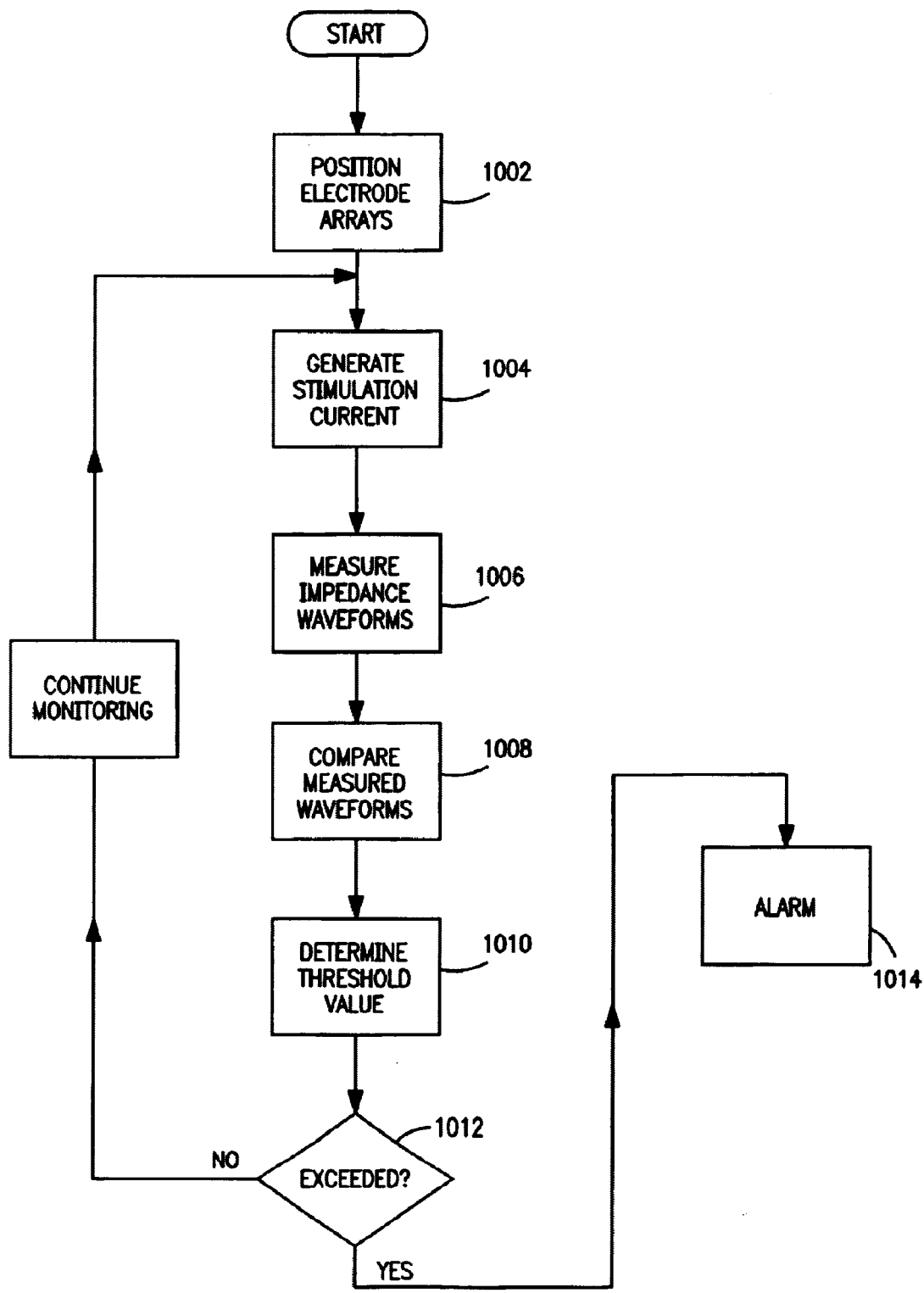
FIG. 10 is a logical flow diagram illustrating one exemplary embodiment of the method of evaluating electrical lead continuity according to the invention.

Referring now to FIG. 10, the method of evaluating the electrical continuity of one or more leads within the system is described. Note that while the following description is based on the two-terminal array configuration (FIGS. 7a–7c) and the use of four arrays as shown in FIG. 3a, the method may be applied to many alternate configurations with equal success.

First, in step 1002, the electrode arrays are disposed on the skin of the subject. The position at which the electrode arrays are disposed on the subject are measured in relation to the thoracic cavity as illustrated in FIG. 3a, or alternatively may be inferred by the weight and height of the subject. Next, a current is generated between the stimulation electrodes and the measurement electrodes of the respective arrays in step 1004. As previously discussed, the current passes through at least a portion of the subject's thoracic cavity, encountering a time-variant impedance therein.

An impedance waveform is then measured from two or more of the measurement terminals of the arrays in step 1006. The waveforms comprise measurements of impedance as a function of time, which is well known in the cardiographic arts. These measured waveforms are then compared to one another in step 1008 to detect changes or variations between them. In the present embodiment, two waveforms are differenced by way of a simple differencing algorithm resident on the processor 608 of the system 600 (FIG. 6), although it will be recognized that other approaches may be used. For example, the base impedance may be calculated for the left and right sides. The larger base impedance may then be subtracted from the smaller base impedance, with this difference then divided by the smaller impedance. The resulting percentage ratio, when greater than a predetermined threshold value, may represent the presence of detached or loose electrodes. While some variation between the waveforms is normal, significant variations are indicative of either a degraded electrical connection, such as between the electrode array terminal and its respective connector, or between the electrolytic gel and the skin of the patient, or even the gel and the terminal of the array or between the cable and connector. A threshold value is determined and set by the operator of the system in step 1010 such that when the threshold "difference" is exceeded as determined by the aforementioned algorithm (step 1012), the operator will be alerted to the degraded condition such as by a visual or audible alarm in step 1014.

In another embodiment of the method, the difference in impedance (or voltage) between the individual terminals 310, 312 of one or more electrode arrays is measured and used as the basis for the continuity determination. Specifically, the difference in the values measured from one terminal 310 with respect to another terminal 312 of the exemplary two-terminal array 302 illustrated herein is measured; when this value exceeds a certain threshold difference value (e.g., 650 Ohms, although other values may be substituted based on any number of factors), a loose electrode or otherwise degraded connection is suspected. It will be recognized that this methodology may also be employed when more that two electrical terminals are electrically connected to the system. For example, if three electrodes (e.g., electrodes 1, 2, and 3) of an electrode array are being used, the algorithm of the present invention would be adapted to measure the difference between each of the non-repeating permutations (i.e., 1–2,1–3, and 2–3) and compare such differences to the threshold.

It will be recognized by those of ordinary skill that other approaches may be utilized for analyzing the impedance (voltage) measurements obtained from the electrode arrays in evaluating electrical continuity. Furthermore, it will be recognized that the aforementioned threshold value may be algorithmically determined and/or parametrically variant. For example, based on data obtained by the system before and/or during operation, the present invention may periodically or continuously calculate new threshold values as a function of time. Alternatively, the system may be adapted to calculate a plurality of such impedance difference values across each of the terminal arrays in use, and average the values periodically to maintain a "moving average" of impedance differences. As yet another alternative, other physiological parameters of the subject being monitored could be used as "triggers" for revised threshold determination and/or impedance difference calculation. Many other such variations and alternatives are possible consistent with the methodology of the present invention.

It is noted that the use of the multi-terminal electrode arrays having predetermined and substantially equal terminal spacing as previously described allows such comparisons between electrode waveforms to be made; errors resulting from uncontrolled spacing of the terminals are effectively eliminated. Using prior art electrodes, the aforementioned method would be largely ineffective, since these error sources would force the threshold value to be set artificially high, thereby potentially masking conditions of degraded electrical continuity which could affect the ultimate accuracy of and cardiac output estimation made by the system.

ICG Module

Referring now to FIGS. 11–14, the improved impedance cardiography module of the present invention is described. The ICG module of the invention utilizes the electrical bio-impedance measurements previously described herein to continuously generate a signal indicative of pulsatile thoracic impedance changes. This pulsatile thoracic impedance signal is processed to produce signals indicative of other related parameters, such as the ventricular ejection time (VET) and the maximum rate of change of pulsatile thoracic impedance, which are used to calculate the volume of blood pumped per stroke according to equations previously discussed. While described specifically in terms of the BioZ® ICG module manufactured by the Assignee hereof, it will be appreciated that the broader inventive concepts disclosed herein may be embodied in any number of different forms and combinations of functionality, several of which are described subsequently herein as alternate embodiments.

As previously discussed, the voltage developed across the thoracic impedance at any instant in time can vary due to a number of different factors. Specifically, the voltage is affected by four primary components: (i) base impedance; (ii) respiration; (iii) cardiac changes; and (iv) patient motion.

The base impedance comprises the largest component of the modulated waveform, and represents the nominal conductivity of the thorax. It is a function of the tissue and fluid distribution within the interrogated area. The average value of the base impedance, or TFI, is roughly 30 Ohms, but can vary from 5 to 60 Ohms in adult humans.

Inhalation and expiration by the patient causes significant impedance changes as gases enter and exit the lungs. The ventilation cycle is relatively long, typically 0.2 to 0.7 Hz with variable magnitude.

Impedance changes occur due to the cardiac cycle, such as after ventricular depolarization (QRS complex), and have very small magnitudes (approximately 0.05–0.3 Ohms). These impedance changes are the result of aortic expansion after blood is ejected from the ventricle, and contraction as blood is flows into the circulatory system.

Movement by the patient causes significant impedance changes due to fluid shifts and density/volume changes in the thorax, with varying frequency and magnitude. The motion component of impedance is effectively eliminated when the patient is monitored at rest.

Figure 11:
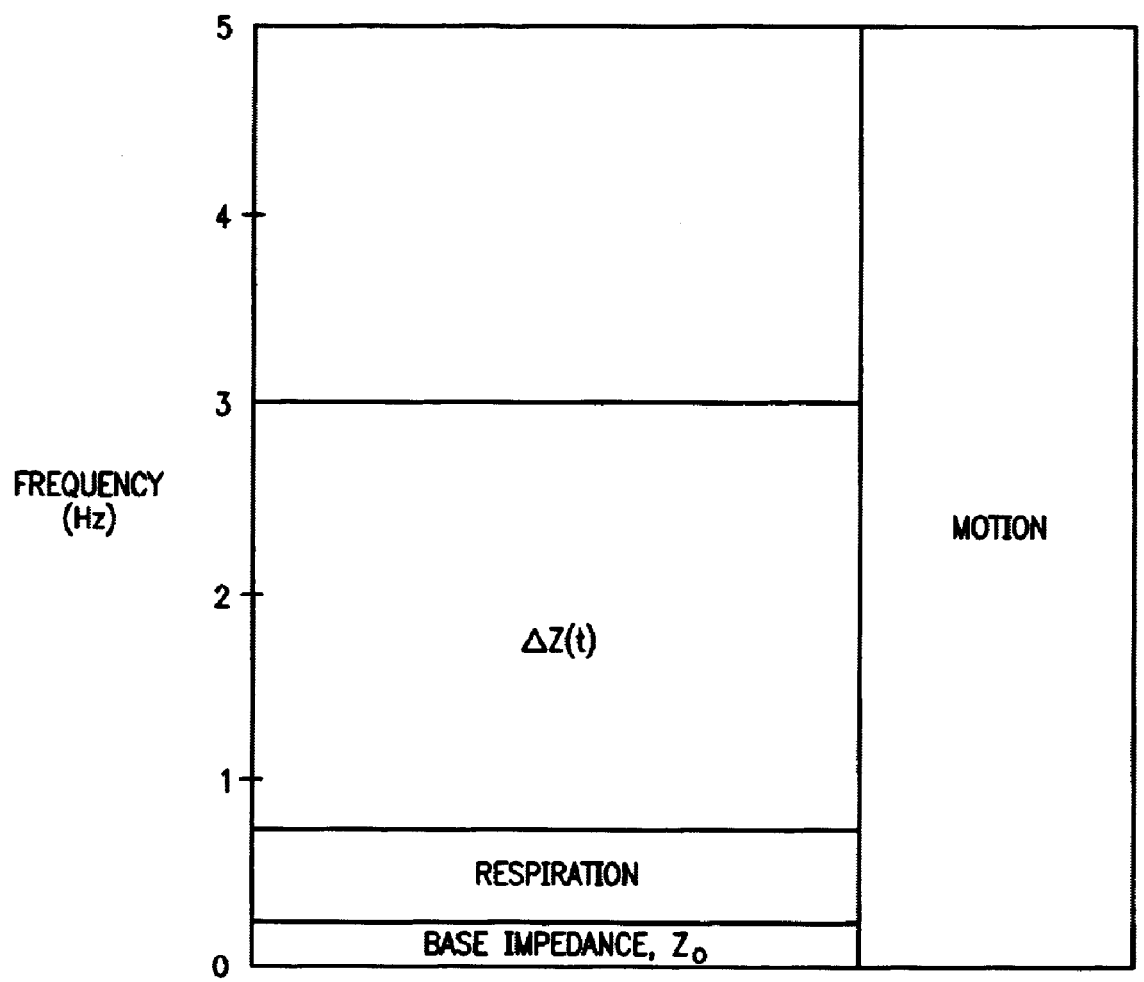
FIG. 11 is a graph illustrating the frequency ranges of thoracic signals for a typical adult human subject.

FIG. 11 is a graph illustrating the frequency ranges of these four signal components for a typical adult human subject.

The ICG module of the invention advantageously addresses the foregoing components of thoracic impedance through its signal processing circuitry and algorithms, now described in detail.

Figure 12:
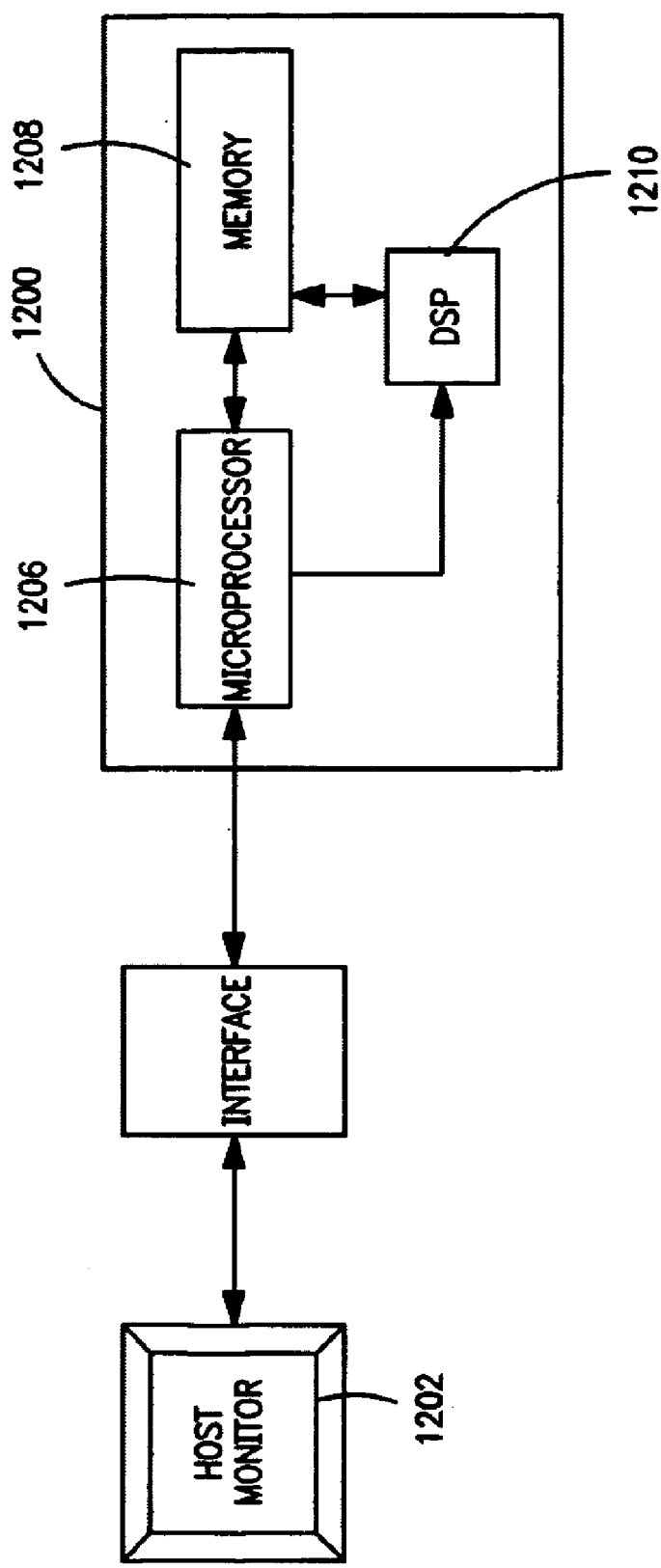
FIG. 12 is a functional block diagram illustrating one exemplary embodiment of the ICG module of the invention, including the connection of the module to a communications interface/monitoring system.

As shown in FIG. 12, the ICG module 1200 of the invention is electrically coupled to the host monitor 1202 via the interface device 1204. The ICG module 1200 generally comprises a microprocessor 1206, storage device 1208, and digital signal processor 1210, as described in greater detail below with respect to FIG. 13. The module 1200 communicates with a host monitor 1202 to continuously monitor and display the cardiac output and pulse rate of the subject under evaluation. Communications are in the illustrated embodiment conducted according to a predetermined protocol (such as a serial interface protocol of the type well known in the art), although other approaches may be substituted with equal success. The module further includes other features such as input power conditioning and "soft-start" current limiting functionality, software/firmware download from the host device, and electrical isolation (e.g., 4000 V) for the subject being monitored.

Figures 1, 13:
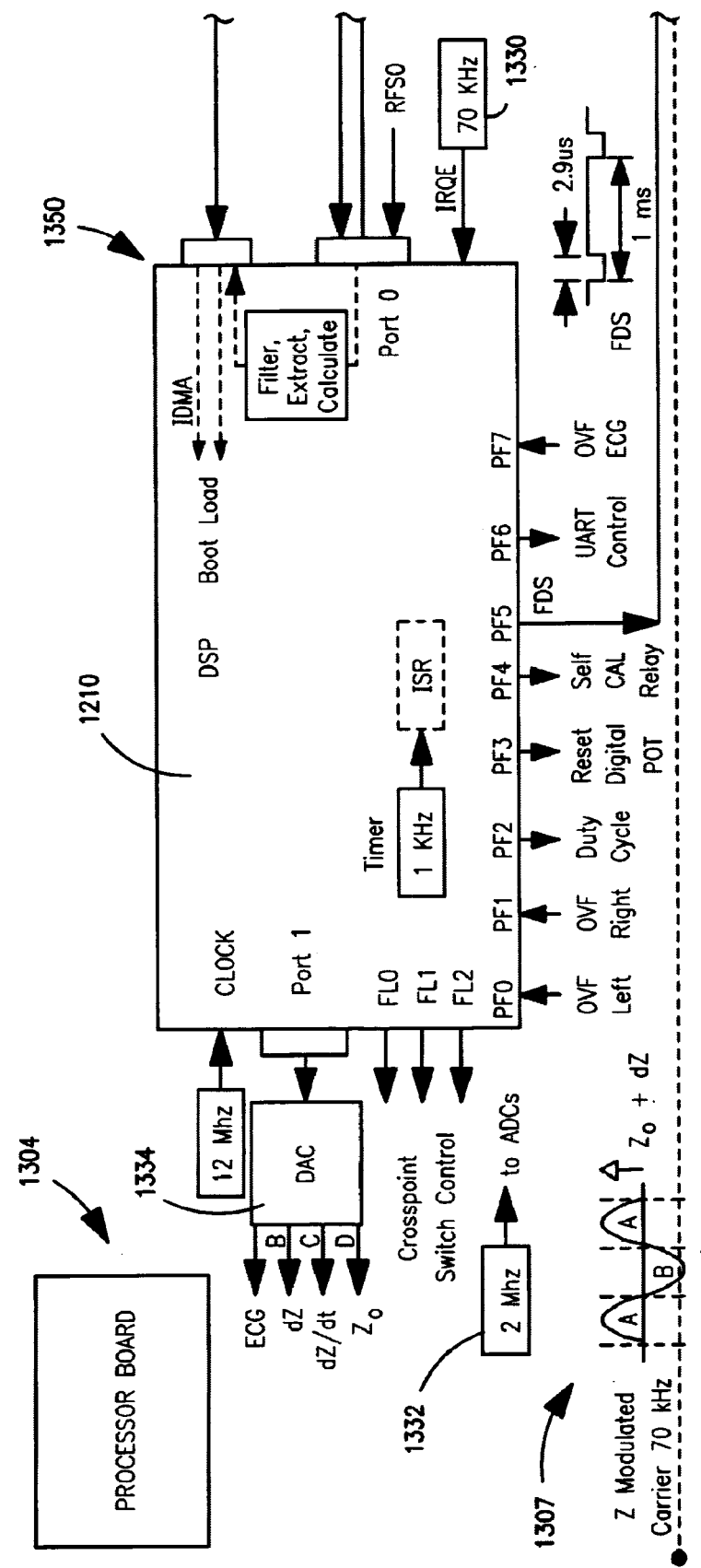
FIG. 13 is a functional block diagram illustrating the processor and patient interface boards of the ICG module of FIG. 12, and relationship of components comprising these boards.
Figures 2, 13:
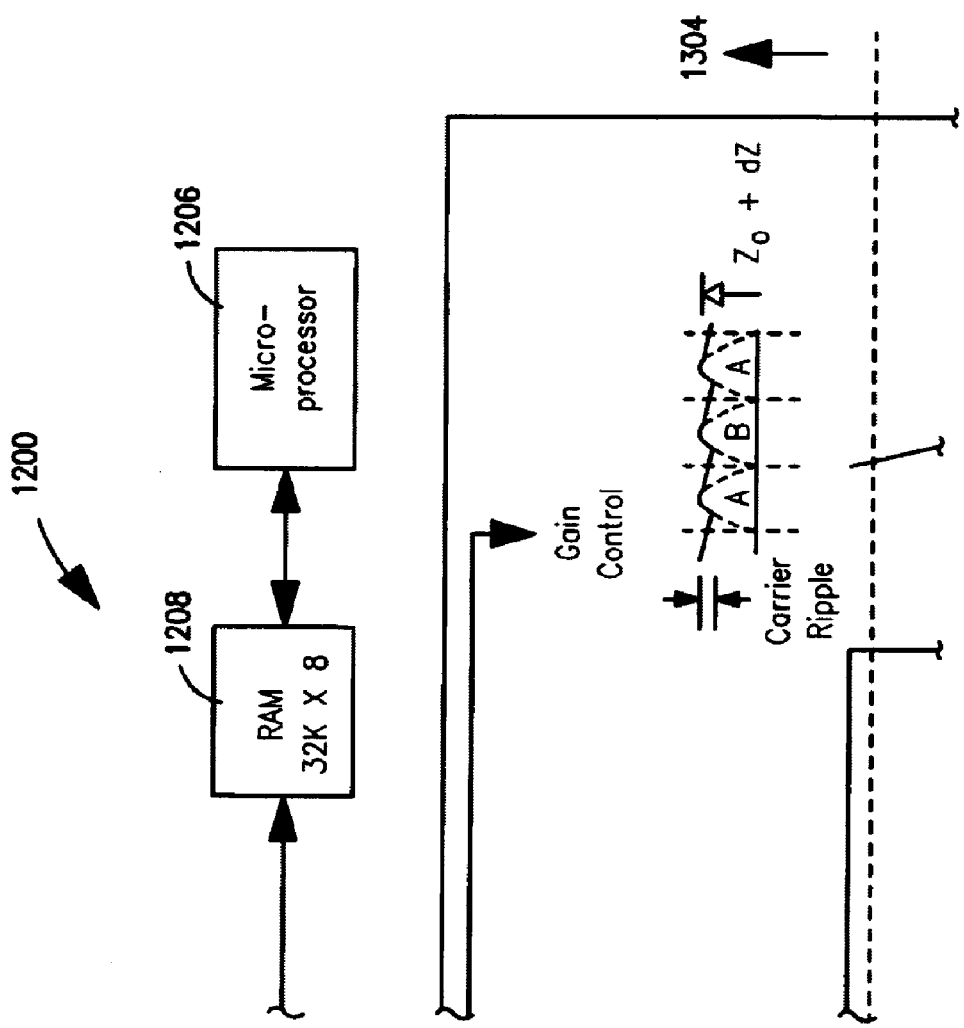
Figures 3, 13:
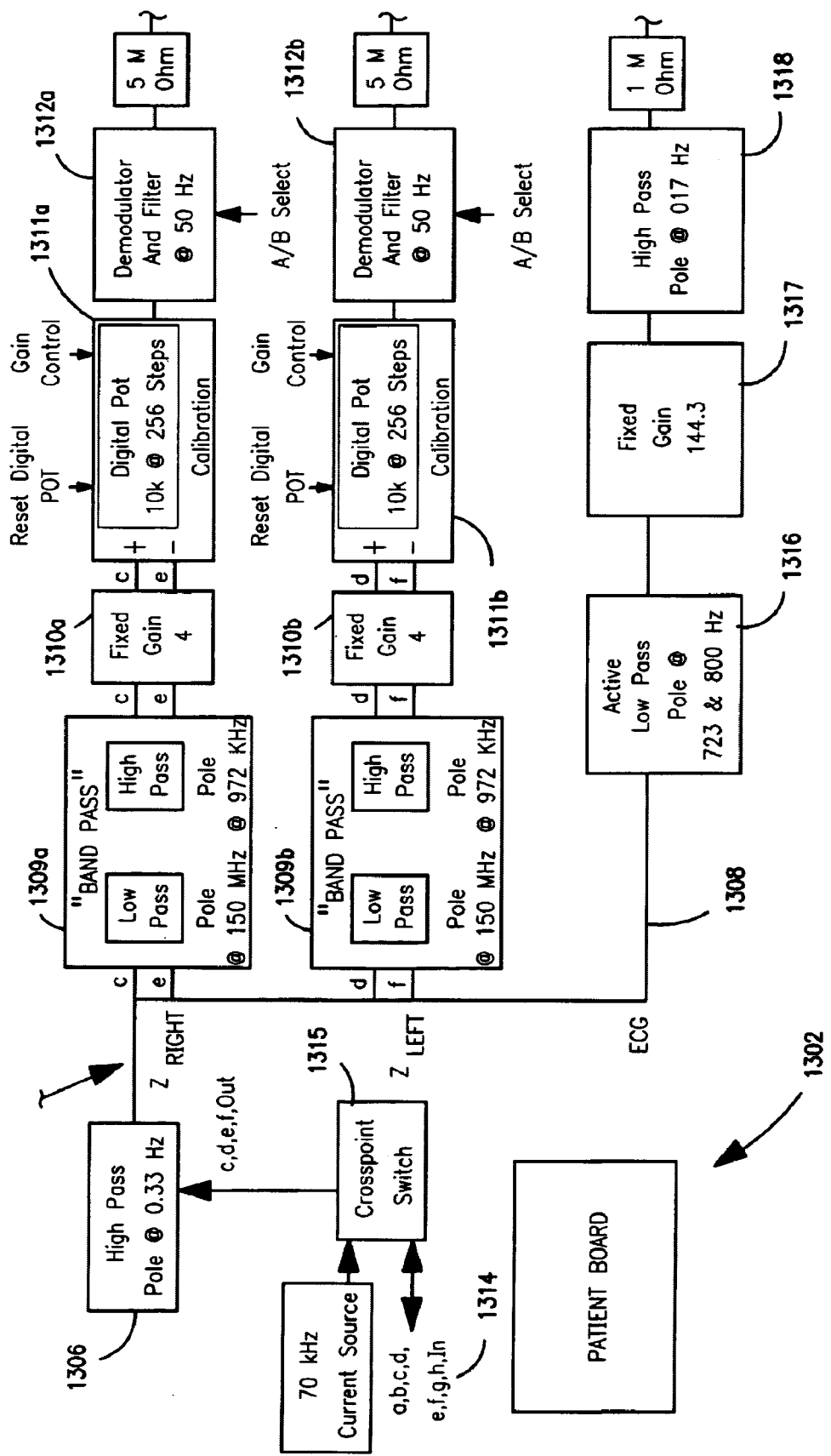
Figures 4, 13:
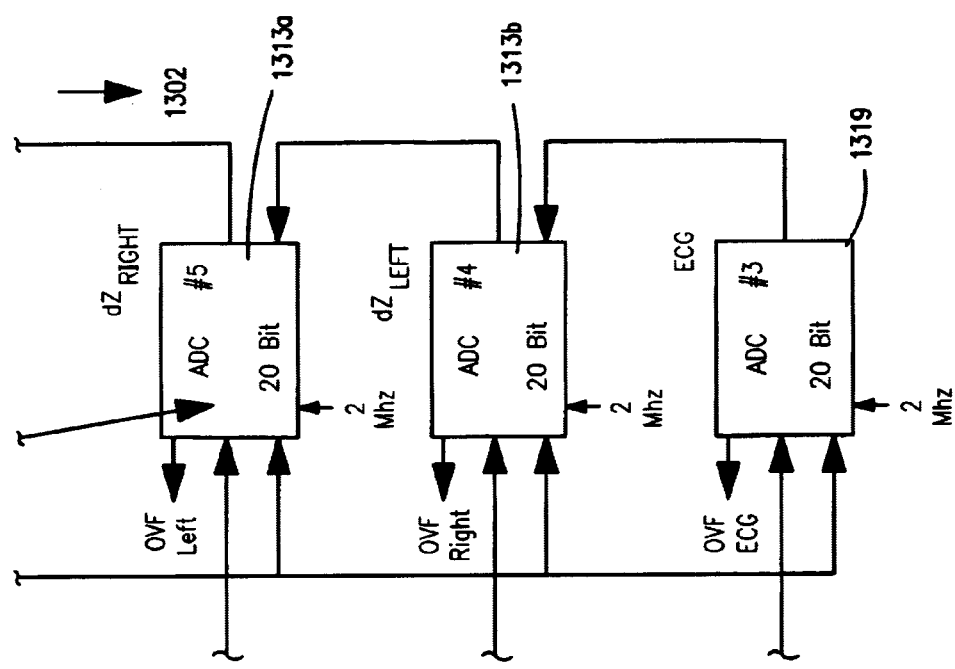

As shown in FIG. 13, the exemplary embodiment of the module 1200 comprises two component boards 1302, 1304, identified herein as the "patient board" 1302 and the "processor board" 1304. It will be recognized that these may or may not be separate physical boards or substrates. The patient board 1302 provides a number of functions, including (i) interface with the external signal sources; e.g., the patient leads and electrodes which provide, inter alia, the impedance and ECG waveform signals to the module; (ii) ECG vector select (described in greater detail below); and (iii) input signal filtration, conditioning, and domain conversion. The patient board 1302 also isolates the electrical and the mechanical ($\Delta Z$) components of cardiac activity from each other, and from the components of respiration and motion present in the signals derived from the subject under evaluation. A first high-pass filter (pole at 0.33 Hz) 1306 filters the input impedance waveform 1307 and ECG waveform 1308. Band-pass filters 1309a, 1309b comprising a low-pass filter with pole at 1.59 MHz and high-pass filter with pole at 9.72 kHz are used to further filter the respective high-pass filtered impedance waveforms of each input channel (a channel being defined for the purposes of this exemplary discussion as a pair of electrodes; i.e., "left" channel and "right" channel). Fixed gain amplifiers 1310a, 1310b receive the output of the band-pass filters 1309a, 1309b for each channel, and provide a fixed gain output signal to respective digital potentiometers 1312a, 1311b, the output of which is supplied to respective demodulators/filters 1312a, 1312b. The output of the demodulator/filter units 1312a, 1312b is passed through 5 M Ohm resistors and subsequently input to respective analog-to-digital converters (ADCs) 1313a, 1313b, which are clocked according to a 2 MHz clock signal (described below).

Figure 21:
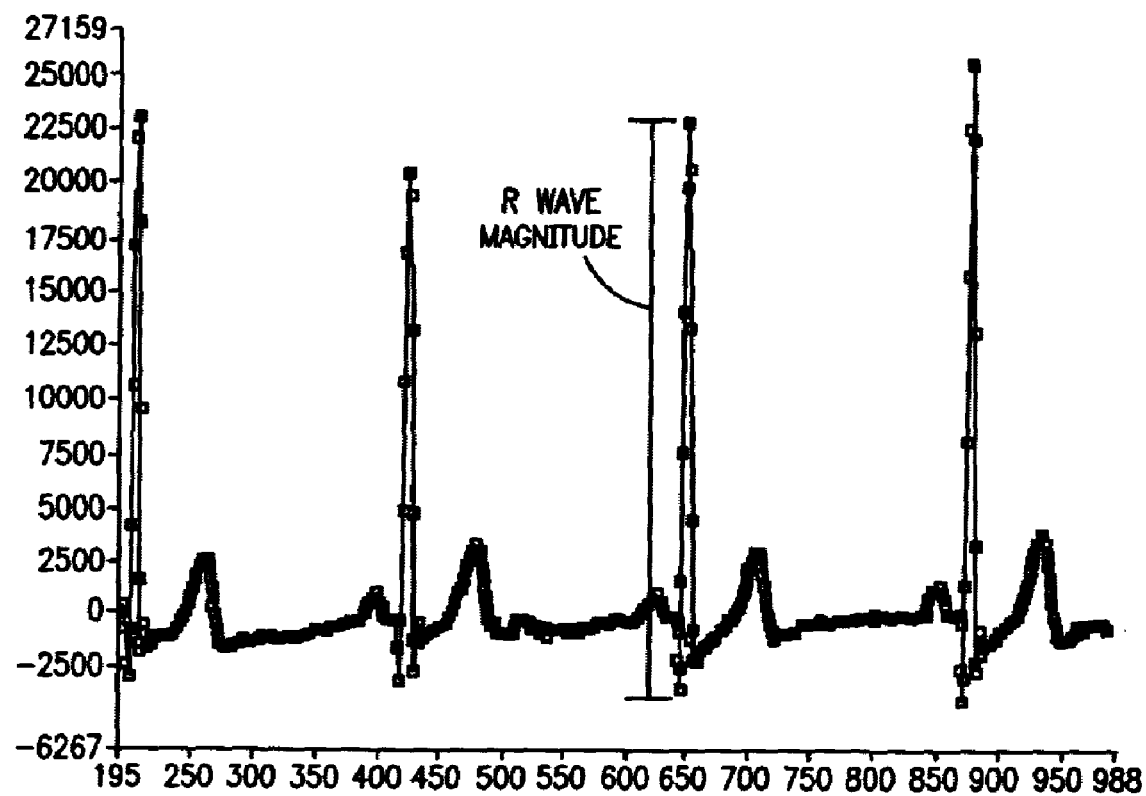
FIG. 21 is a graphical representation of the R-wave amplitude calculation according to the invention.
Figure 22:
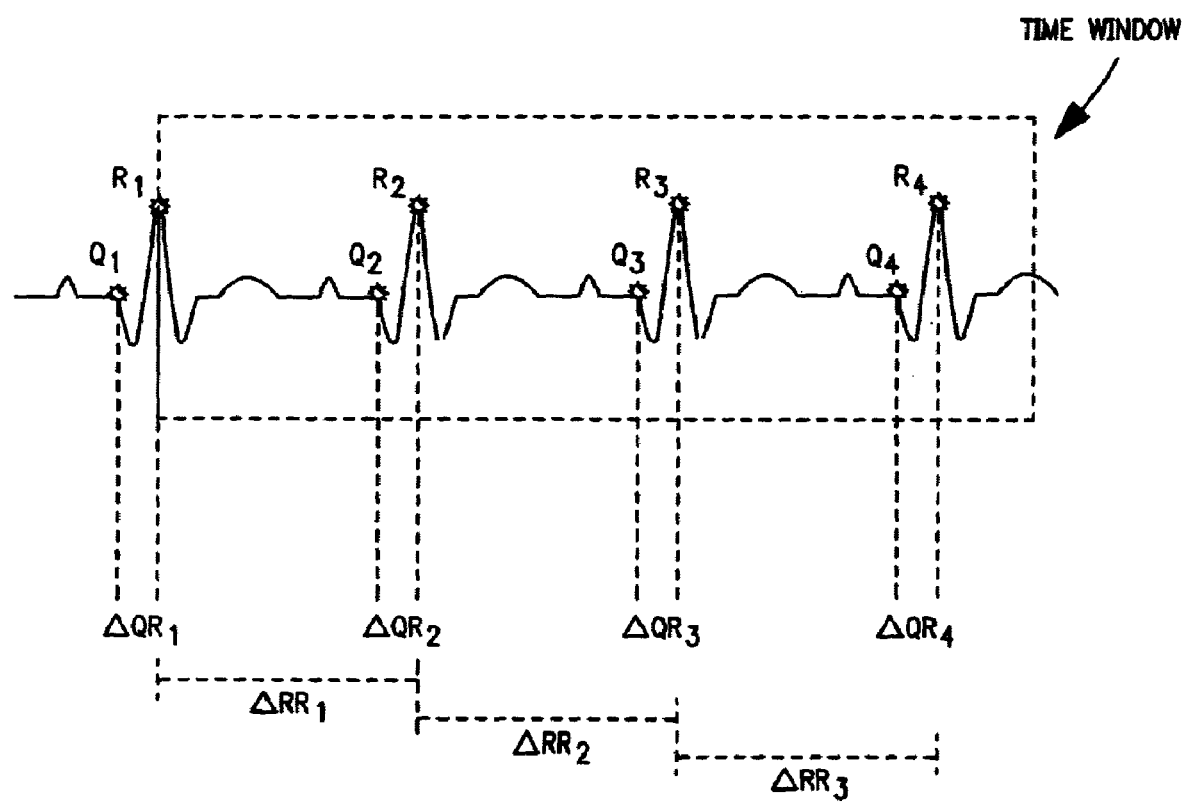
FIG. 22 is a graphical representation of the methodology for calculating the exemplary QR and RR interval difference parameters according to the invention.
Figure 23:
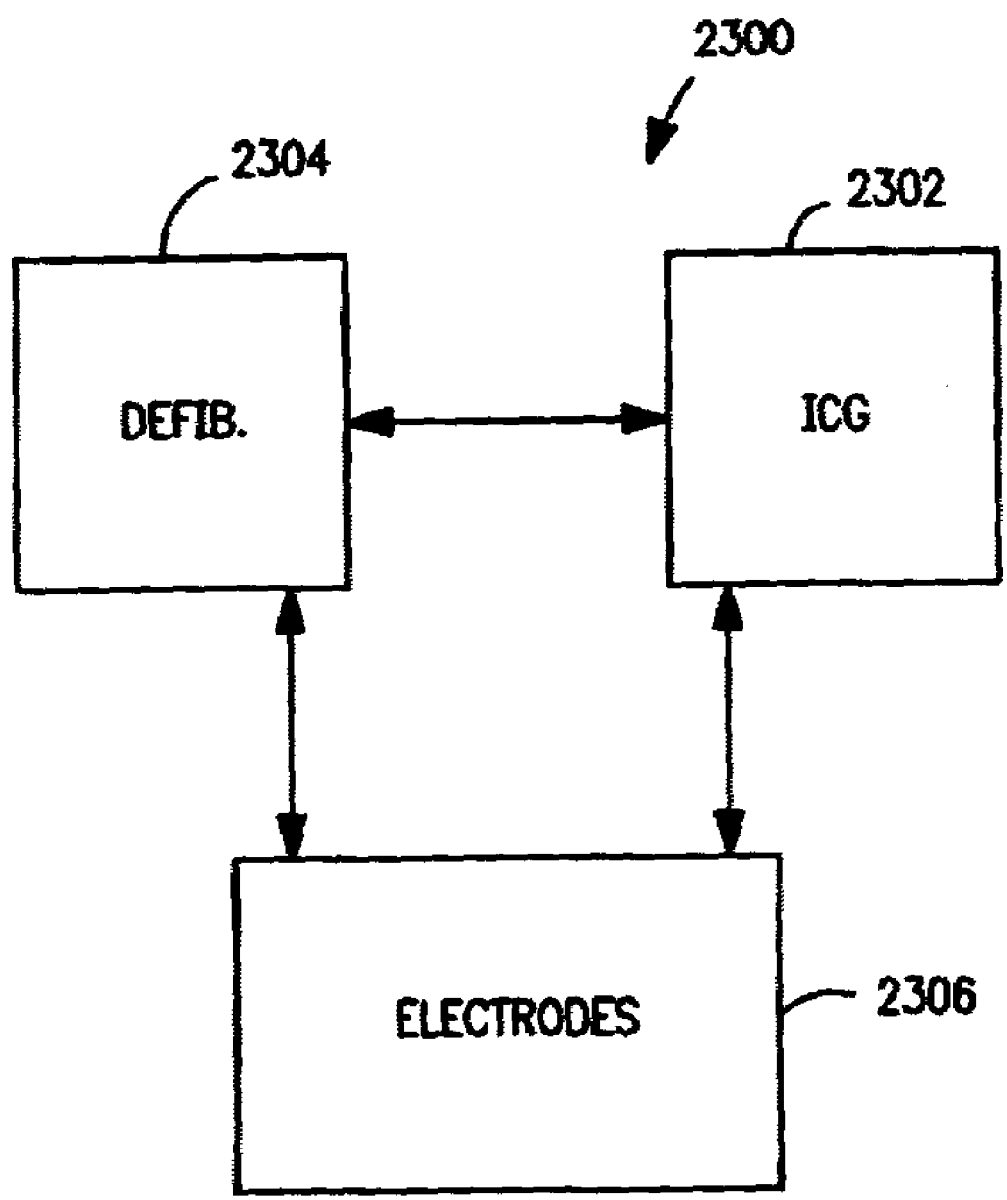
FIG. 23 is functional block diagram of one exemplary embodiment of the defibrillator apparatus of the present invention.

The patient board 1302 further comprises a plurality of ECG inputs 1314 which are obtained from the aforementioned electrode pairs and input to a crosspoint switch 1315 (e.g., a 16×16 analog multiplexer such as the AD75019 device manufactured by Analog Devices), which selects the best "quality" input from among the four inputs as described in detail below with respect to FIGS. 20–22. The selected ECG signal is low-pass filtered 1316, amplified to a fixed gain 1317, high-pass filtered 1318, and then supplied (via 1 M Ohm resistor) to the ECG ADC 1319. The three ADCs 1313a, 1313b, 1319 output digitized signals to the DSP 1210 on the processor board 1304, described below.

The patient board 1302 also uses this crosspoint switch to provide several other functions, including connection of leads to the patient, provision of multiple ECG vectors, loose electrode testing (previously described), cable identification, and calibration.

The processor board 1304 comprises a digital signal processor (DSP) 1210 with direct memory access (DMA) of the type well known in the electronic arts, a microprocessor 1206, a storage device 1208 coupled with the DSP 1210 and microprocessor 1206 via a data bus, a first signal (constant current) source 1330 generating a nominal 70 kHz output signal, a second signal source 1332 generating a nominal 2 MHz output signal, a clock signal generator (12 MHz nominal), and digital-to-analog converter (DAC) 1334.

In one variant, the module is configured with a DC/DC converter operating at 90 kHz, and the aforementioned ICG current source at 70+/−6 kHz.

FIG. 13a graphically illustrates the impedance signal extraction process performed by the ICG module 1200 of the present invention.

In the illustrated embodiment of FIG. 13, the microprocessor 1206 comprises a microcomputer running at a crystal frequency of approximately 32.7 KHz, although it will be recognized that other platforms may be substituted with equal success. The system clock is generated by an on-chip phase-locked loop (PLL) and is software programmed for an operating frequency of 16 MHz. The device is operated in the 8-bit bus operating mode with all data transfers occurring on data lines 8 through 15. The processor also has a QSPI built in, which in the present embodiment is used for communications to the host device, such as by using a serial interface protocol of the type previously referenced herein.

The ICG module 1200 utilizes a three-part software architecture comprising three modules: (i) "Initialization" module; (ii) "Operating" module; and (iii) "Processing" module. Any one of the three software code modules can be independently downloaded.

The Initialization operating system of the microprocessor 1206 comprises a variant of the "C Executive" system manufactured by JMI Software Consultants, Inc., although it will be recognized that other operating systems may be substituted. C Executive comprises a real-time, memory-resident, event driven monitor program designed for embedded systems which require multi-tasking functionality and ROM storage. The initialization module software uses the initialization OS for process scheduling, input and output, and inter-process communication.

Figure 13B:
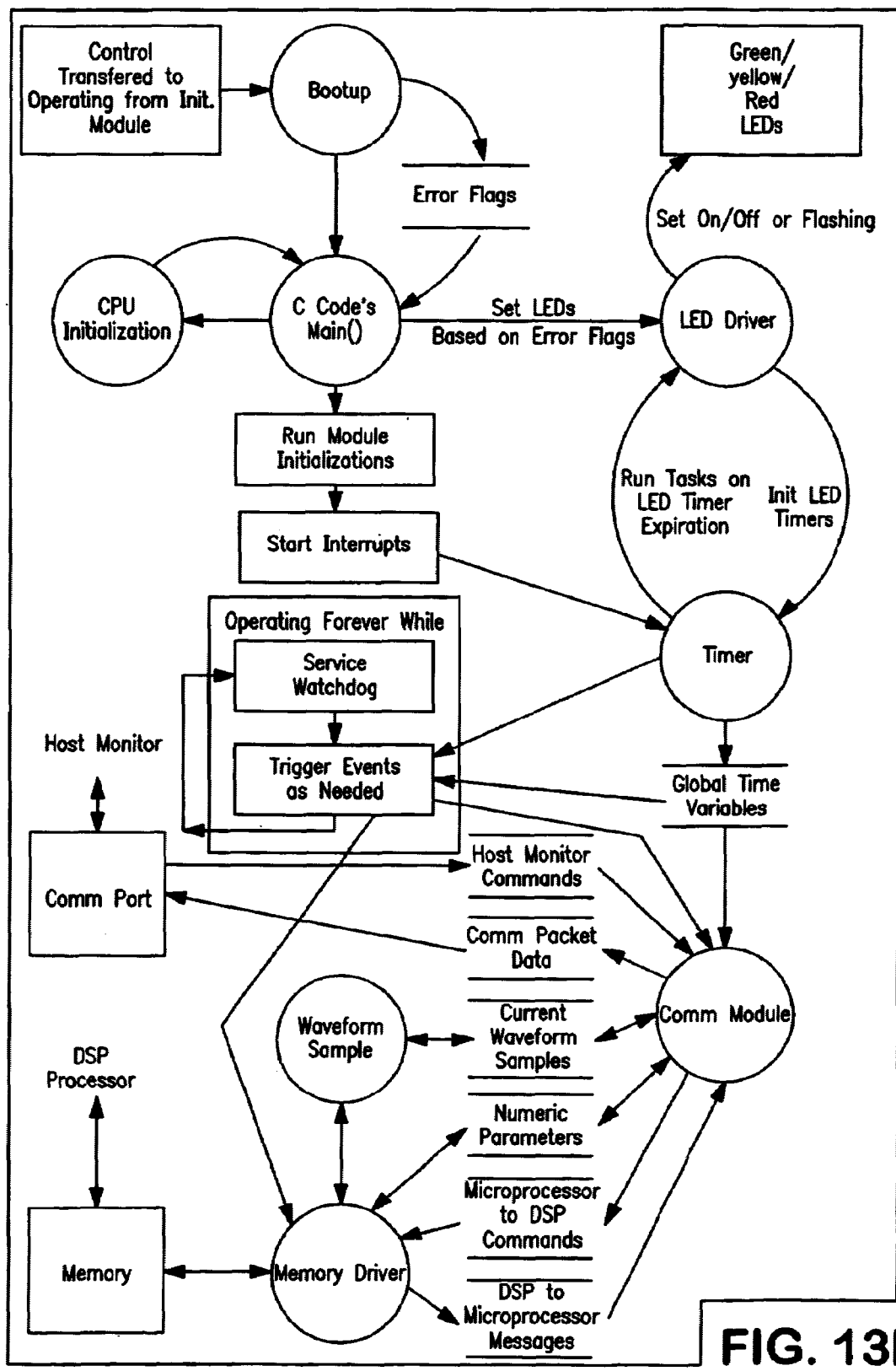
FIG. 13b is a logical flow diagram illustrating the Operating module program flow within the microprocessor of the ICG module of FIG. 13.

The processor Operating code does not use any operating system. Upon booting, the microprocessor registers are set for proper operation. Chip selects, interrupts, internal memory, stack pointer and initial program counter are all the responsibility of the Operating module's boot process. FIG. 13b graphically illustrates the high-level program flow of the Operating software module of the illustrated embodiment.

The processing module executes the bioimpedance algorithms. It also controls peripheral functions, such as the gain of the impedance amplifiers, the setting the ECG vector, reading of the impedance and ECG A/D converters, and detection of electrical continuity. The DSP 1210 of the invention comprises an Analog Devices ADSP-2181 device, although it will be recognized that any digital processing device adapted for algorithms such as those described herein may be used with proper adaptation. For example, members of the Texas Instruments 'C4x family of floating point DSPs, 'C5x family of fixed point processors, 'C6x family of VLIW processors, the Lucent DSP 16000 family, or even a user-customized processor core or ASIC may be used. Many other types of digital signal processors exist, any number of which may be adapted for use with the present invention.

Figure 13C:
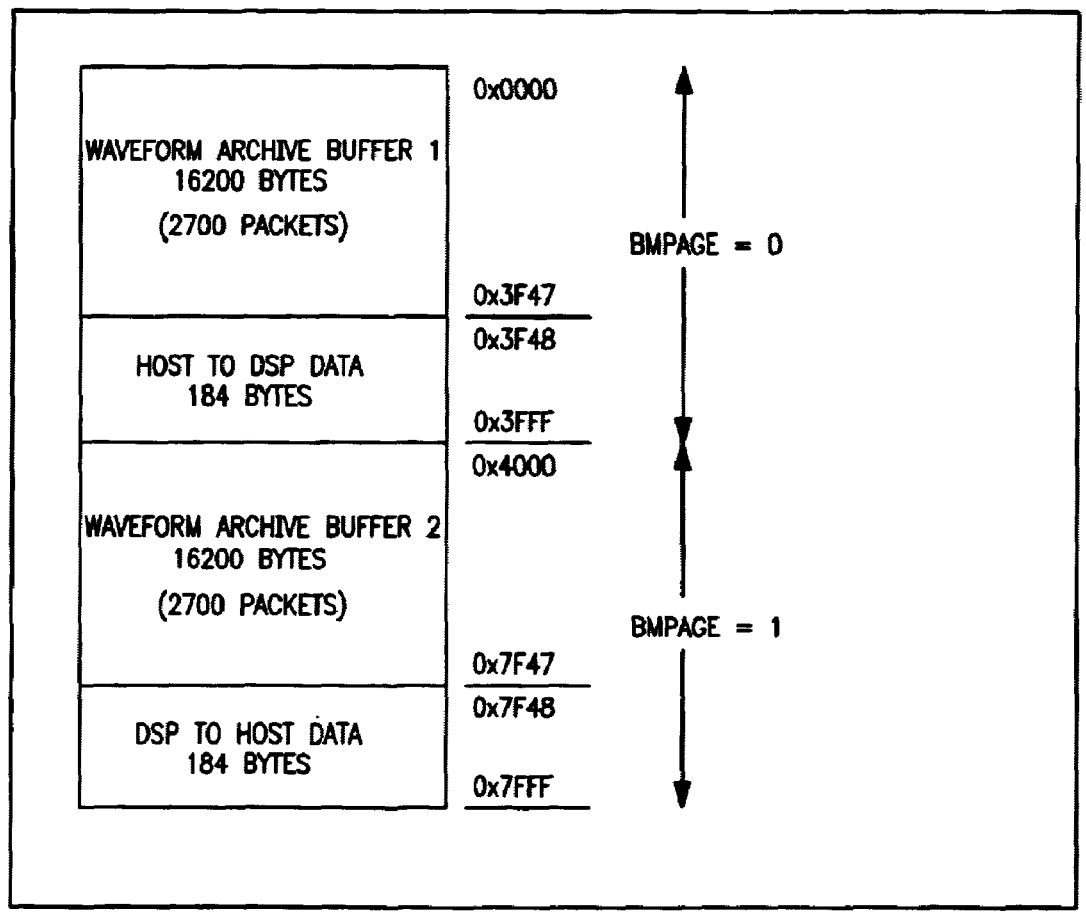
FIG. 13c is a graphical representation of one exemplary memory map used with the storage device of the processor board of FIG. 13.

Parameters determined from the digitized data are communicated to the microprocessor 1206 via the storage device 1208, specifically by writing data words to predetermined locations within the storage device. In the present embodiment, a dual-port RAM (DPR) is selected to allow dual-port access and two-way communication by the DSP 1210 (via, e.g., the BDM port) and microprocessor 1206 via first and second memory ports, respectively; however, it will be recognized that other types and configurations of storage device including DRAM, SDRAM, SRAM, dual data rate synchronous DRAM (DDR-SDRAM), ROM, or even non-semiconductor storage devices may be substituted. The embodiment of FIG. 13 further comprises a DMA unit of the type well known in the art, thereby facilitating direct memory accesses by the processor(s). The module 1200 is further configured such that address and data bus interfaces exist between the microprocessor 1206 and storage device 1208, and between the DSP 1210 and storage device 1208, thereby providing for memory addressing and data transfer by both processors. FIG. 13c illustrates one exemplary embodiment of the memory map used with the DPR 1208 of the ICG module.

An address range is also specified at the microprocessor 1206 and connected to the DSP's DMA port 1350 for DSP code download from the microprocessor 1206 (and host 1202) to the DSP 1210 during operation.

The impedance and ECG waveform data present within the module consists of all measured and calculated parameters related to a specific cardiac event, without any averaging. The start of data is placed at the Q point of the cardiac cycle measured. Waveform data is stored in the order shown in Table 1:

TABLE 1

| Byte | Value | Description |
| --- | --- | --- |
| 0 | Start_data | Framing byte = 0xff |
| 1 | Error_status | Error codes for cardiac cycle |
| 2 | DSP Version integer | XX.00 |
| 3 | DSP Version fraction | 0.XX |
| 4 | ECG full scale range MSB | |
| 5 | ECG full scale range LSB | |
| 6 | ΔZ full scale range MSB | |
| 7 | ΔZ full scale range LSB | |
| 8 | R—R interval MSB | Ms |
| 9 | R—R Interval LSB | |
| 10 | PEP MSB | Ms |
| 11 | PEP LSB | |
| 12 | LVET MSB | Ms |
| 13 | LVET LSB | |
| 14 | Predicted LVET MSB | Ms |
| 15 | Predicted LVET LSB | |
| 16 | Base Impedance MSB | Ω × 100 |
| 17 | Base Impedance LSB | |
| 18 | Integral MSB | ΔZ integral * 100000 |
| 19 | Integral LSB | |
| 20 | Baseline MSB | ΔZ baseline value for Integral |
| 21 | Baseline LSB | |
| 22 | $\frac{dZ(t)}{dt_{max}}/Z_o$ MSB | value* 10000 |
| 23 | $\frac{dZ(t)}{dt_{max}}/Z_o$ LSB | |
| 24 | $\frac{d^2Z(t)}{dt^2_{max}}/Z_o$ MSB | value* 1000 |
| 25 | $\frac{d^2Z(t)}{dt^2_{max}}/Z_o$ LSB | |
| 26 | Ideal Weight MSB | Kg × 100 |
| 27 | Ideal Weight LSB | |

TABLE 1-continued

| Byte | Value | Description |
| --- | --- | --- |
| 28 | R wave dv/dt detection threshold MSB | Samples |
| 29 | R wave dv/dt detection threshold LSB | |
| 30 | Pacer dv/dt detection threshold MSB | Samples |
| 31 | Pacer dv/dt detection threshold LSB | |
| 32 | Gender | 0 = male, 1 = female |
| 33 | Height | Cm |
| 34 | Weight | Kg |
| 35 | Body frame | 0 = small, 1 = medium, 2 = large |
| 36 | Age | Years |
| 37 | MAP | MmHg |
| 38 | Systolic Pressure | MmHg |
| 39 | Diastolic Pressure | MmHg |
| 40 | CVP | MmHg |
| 41 | PAOP | MmHg |
| 42 | Display Update Rate | 1–60 cycles |
| 43 | Cycle Averaging | 1–60 cycles |
| 44 | ECG Vector | 0 = EF, 1 = CF, 2 = DF, 3 = ED |
| 45 | Waveform Buffer Configuration | |
| 46 | Demo Waveform Flag | 0 = OFF, 1 = ON |
| 47 | Pacer Detection | 0 = OFF, 1 = ON |
| 48 | Electrode configuration | 0 = average, 1 = left, 2 = right |
| 49 | End data | Framing byte = 0xff |

So-called "live" waveform data is written into memory 1208 at a predetermined rate and at predetermined addresses to facilitate subsequent analysis; Table 2 illustrates the data write operations into memory performed by the DSP 1210 at a 200 Hz rate:

TABLE 2

| Data | Memory address | Description |
| --- | --- | --- |
| ΔZ | 7FA0 | |
| ECG | 7FA2 | |
| Respiration | 7FA4 | |
| dZ/dt | 7FA6 | |
| pacer impulse | 7FA8 | |
| Pace enhanced ECG | 7FAA | ECG + pacer spikes |
| ECG gain factor | 7FAC | |
| Loose Electrode | 7FAE | |

The module 1200 further utilizes a 512K×8 static RAM (SRAM) array for temporary data storage. The static RAM is also used as temporary storage of ICG Monitor program code during program download of the software. The program code is stored in a 128K×8 sectored "flash" EPROM. This device can be erased on an individual sector basis. The first sector of the flash memory is used for storing the initialization (boot-up) code. In general, this sector of code is not modified, thereby ensuring that even if a download of code fails, the module will still be able to attempt another download. The other seven sectors of the flash memory are used for storage of the Operating code. As previously described below, the Operating code is the code which is run during normal operation of the module. This code can be updated using the host monitor or other external storage device.

The DSP 1210 of the present embodiment is also configured to receive a variety of useful data from the host/interface, as set forth in Table 3 below:

TABLE 3

| Data | Example DPR address | Description |
|---|---|---|
| Gender | 3F50 | 0x0000 = male |
|  |  | 0x0001 = female |
| Height | 3F52 | Centimeters |
| Weight | 3F54 | Kilograms |
| Body Type | 3F56 | 0x0000 = small |
|  |  | 0x0001 = medium |
|  |  | 0x0002 = large |
| Age | 3F58 | Years |
| MAP | 3F5A | MmHg |
| Systolic | 3F5C | MmHg |
| Diastolic | 3F5E | MmHg |
| CVP | 3F60 | MmHg |
| PAOP | 3F62 | MmHg |

Figure 13D:
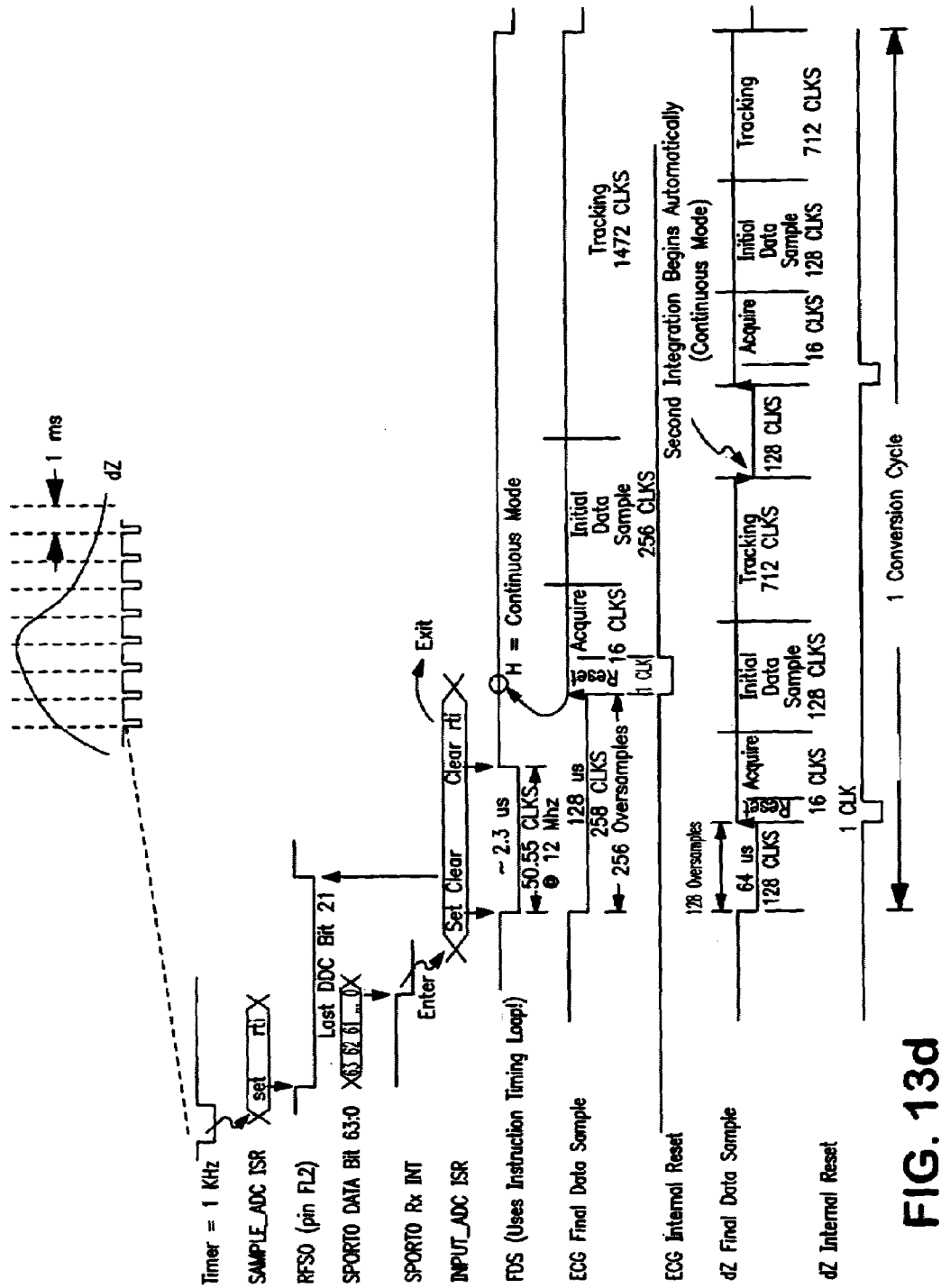
FIG. 13d is a graphical representation of the DSP port (e.g., SPORT0) and ADC data acquisition and timing relationships of the module of FIG. 12.

Other ports on the DSP 1210 are used for various functions in the module. For example, the SPORT0 is a standard port of the DSP which is used to transmit setup control to the ADCs 1313a, 1313b, 1319, digital potentiometers 1311a, 1311b, and the crosspoint switch, and receive data from the ADCs. DSP port SPORT1 is used to transmit data to the DAC 1334. FIG. 13d graphically illustrates the SPORT0 and ADC data acquisition and timing relationships of the present embodiment in detail.

Figure 14:
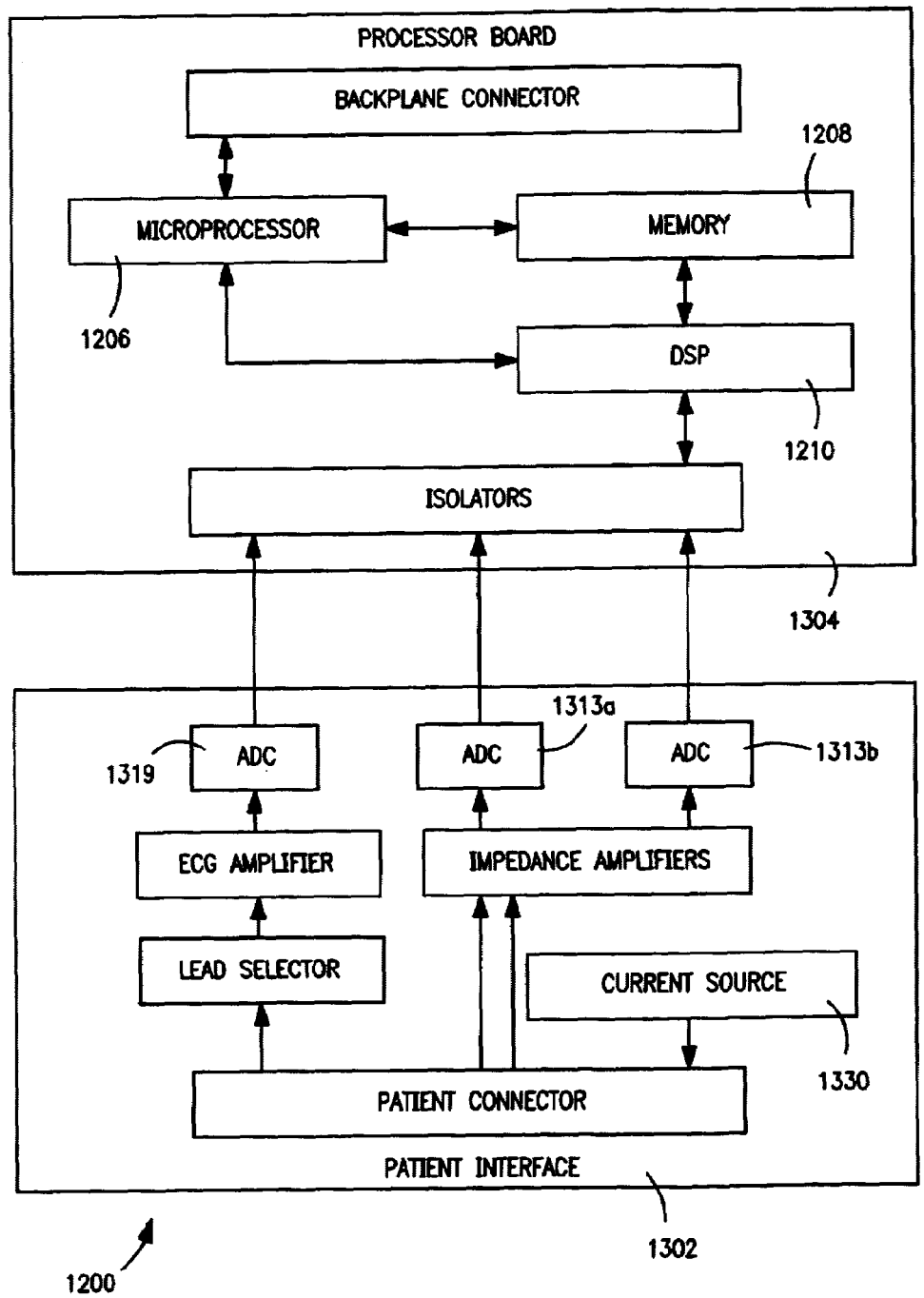
FIG. 14 is functional block diagram illustrating the data flow within the ICG module of FIGS. 12–13.

FIG. 14 illustrates portions of the data and signal flow within and between the patient and processor boards (and associated components) of the ICG module of FIGS. 12–13.

Appendix I hereto provides a listing of the various parameters utilized within or generated by the ICG module 1200. Note that the VEPT (Volume of Electrically Participating Tissue) and BSA (Body Surface Area) are, according to the present methodology, determined using the sex, height and weight of the patient measured, although other approaches may be substituted. Hemodynamic parameters are calculated from the values HR, PEP, VET, TFI, $$\frac{dZ(t)}{dt_{max}}$$

and $$\frac{d^2 Z(t)}{dt^2_{max}}$$

which are extracted from the aforementioned ECG, $$\frac{dZ(t)}{dt}$$

and $$\frac{d^2 Z(t)}{dt^2}$$

waveforms. Indexed parameters are obtained by dividing the parameter (e.g., BSA, CO, CI, SI) by the appropriate index.

Appendix II details the communications protocol (including memory address) for the patient data communicated by the exemplary embodiment of the module to the host device.

Fiducial Point Detection

Two important parameters present in estimations of cardiac output are (i) the maximum negative change in the impedance signal (Z(t)) as a function of time, $$\frac{dZ(t)}{dt_{max}};$$

and (ii) the ventricular ejection time (VET). These parameters, as well as other related parameters, are found from features referred to as "fiducial points" that are present in the inverted first derivative of the impedance waveform, $$\frac{dZ(t)}{dt}.$$

For example, the maximum value of $$\frac{dZ(t)}{dt},$$

referred to as $$\frac{dZ(t)}{dt_{max}},$$

is generally determined from the time at which the inverted derivative value has the highest amplitude, also commonly referred to as the "C point". The value of $$\frac{dZ(k)}{dt_{max}}$$

is calculated as this amplitude value. VET (also known as LVET, relating to the left ventricle of the heart in a human) corresponds generally to the time during which the aortic valve is open. That point in time associated with aortic valve opening, also commonly known as the "B point", is generally determined as the time associated with the onset of the rapid upstroke (a slight inflection) in $$\frac{dZ(t)}{dt}$$

before the occurrence of the C point. The time associated with aortic valve closing, also known as the "X point", is generally determined as the time associated with the inverted derivative global minimum, which occurs after the C point.

In addition to the foregoing "B", "C", and "X" points, the so-called "O point" may be of utility in the analysis of the cardiac muscle. The O point represents the time of opening of the mitral valve of the heart. The O point is generally determined as the time associated with the first peak after the X point. The time difference between aortic valve closing and mitral valve opening is known as the iso-volumetric relaxation time, IVRT.

Impedance cardiography further requires recording of the subject's electrocardiogram in conjunction with the thoracic impedance waveform previously described. Processing of the impedance waveform for hemodynamic analysis requires the use of ECG fiducial points as landmarks. Processing of the impedance waveform is generally performed on a beat-by-beat basis, with the ECG being used for beat detection. In addition, detection of some fiducial points of the impedance signal may require the use of ECG fiducial points as landmarks. Specifically, individual beats are identified by detecting the presence of QRS complexes within the ECG. The peak of the R wave (commonly referred to as the "R point") in the QRS complex is also detected, as well as the onset of depolarization of the QRS complex ("Q point"). In patients with a pacemaker, the natural process of ventricular depolarization is either supplemented or entirely overridden.

Accordingly, in another embodiment, the ICG module of the present invention is further modified to incorporate fiducial point detection within the aforementioned impedance and/or ECG waveforms provided as inputs to the module. Specifically, "event markers" are placed within the waveform buffers to indicate the algorithm detection points with reference to the waveform samples. Table 4 below shows some of the marker values used for the various fiducial points:

TABLE 4

| Fiducial Point | Marker Value |
| --- | --- |
| Q point | 0x10 |
| B point | 0x20 |
| X point | 0x30 |
| dZ/dt max | 0x50 |
| d²Z/dt² max | 0x60 |

The difference between each detected X and B point is used to calculate ventricular ejection time (LVET). The magnitude of the largest negative derivative of the impedance change occurring during systole ($dZ/dt_{max}$) is calculated from the C point. LVET and $dZ/dt_{max}$ are then used to calculate the stroke volume, from which cardiac output is derived.

In yet another variant, fiducial point detection within the ICG module is conducted using the wavelet transform methodology as disclosed in co-pending U.S. patent application Ser. No. 09/764,589, entitled "Method And Apparatus For Hemodynamic Assessment Including Fiducial Point Detection", filed Jan. 17, 2001, assigned to the Assignee hereof, and incorporated herein by reference in its entirety herein. The fiducial points of the ΔZ and dZ/dt waveforms (e.g., B, C, X, and O) are detected in this variant using discrete wavelet transforms, rather than by empirical detection, which is based on processing features in the first and second derivatives of ΔZ(t). The wavelet transform methodology advantageously requires only simple additions and multiplications of real numbers, thereby substantially simplifying the processing associated with the cardiac output determination performed by the DSP 1210 and associated algorithms. Furthermore, the wavelet transform methodology, compared to the empirical methodology, is much less sensitive to noise artifact.

Similarly, fiducial points are utilized in evaluating the electrocardiogram waveform of the subject, with specific individual "beats" of the subject's cardiac muscle being identified through detection of one or more fiducial points, either by the aforementioned wavelet transforms or by other means. The peak of the R wave (R point) in the QRS complex as well as the onset of depolarization of the QRS complex (Q point) are also detected. The time interval between the R waves is also used to calculate the subject's heart rate.

Alternate ICG Module Configurations

Figure 15B:
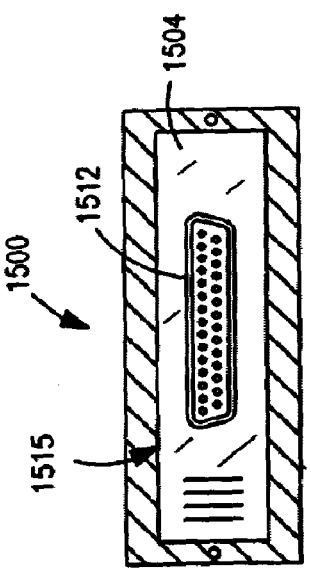
FIGS. 15a–c are top, rear, and front plan views, respectively, of the module of FIGS. 12–14, configured so as to be received within an equipment rack.
Figure 15C:
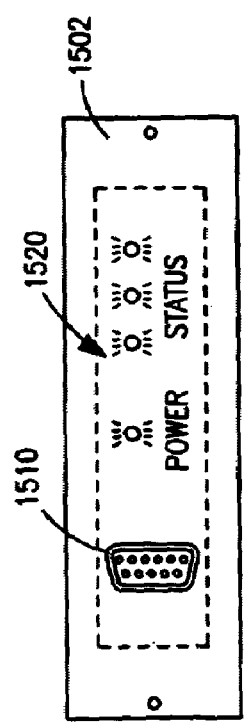
Figure 15A:
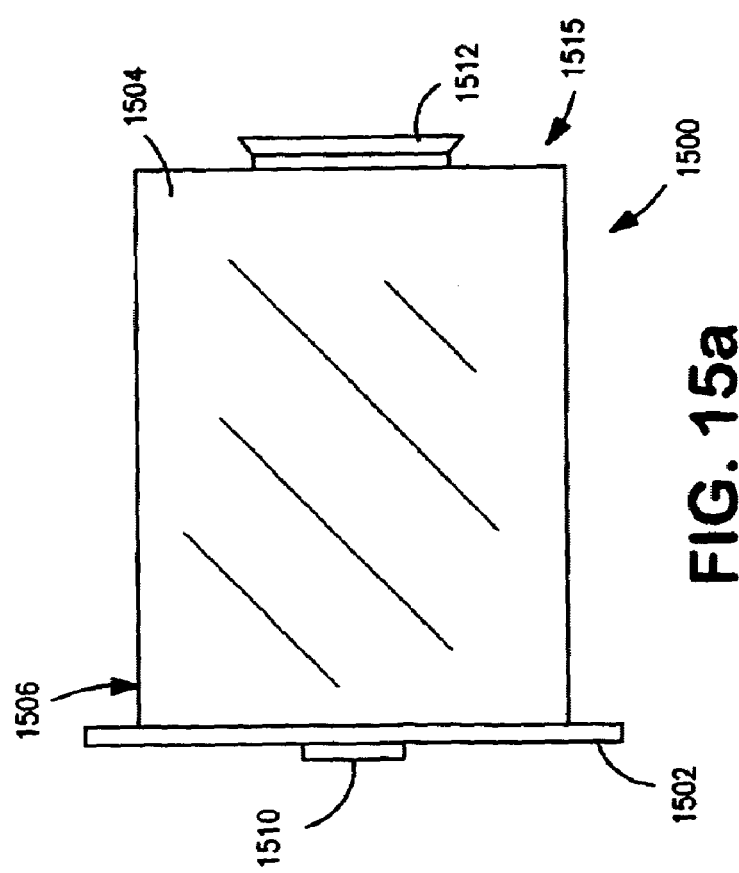

Referring now to FIGS. 15a–c, one embodiment of the ICG module of the present invention adapted for rack mounting is described. As shown in FIG. 15, the module 1500 is fitted with a faceplate 1502 disposed generally at the front portion 1506 of the module housing 1504, as well as a plurality of electrical connectors 1510, 1512, one connector 1510 disposed generally at the front portion 1506 of the housing, and one connector 1512 at the rear portion 1515 of the housing 1504. A debug port connector (not shown) is also provided to facilitate debug of the microprocessor 1206. Optional module status indicators 1520 are also disposed on the faceplate 1502 so as to be viewable by a user or clinician during operation of the module when the module is received within an equipment "rack" (described in greater detail below). In the illustrated embodiment, the module housing 1504 is shaped and sized so as to be received within the rack adjacent or generally in proximity to other modules, such that space is economized.

The front panel connector 1510 comprises the ICG module interface with the patient being monitored, including electrical connection to the measurement and stimulation electrode terminals previously described herein. The front panel connector 1510 may be of any configuration, such as a multi-pin standardized male or female electrical connector of the type well known in the art, although literally any configuration (proprietary or otherwise) may be substituted.

The rear panel connector 1512 allows for electrical connection of the module to the host monitor/interface unit, such as for example via a multi-pin female connector for mating with backplane connectors of the host monitoring equipment (including any voltage supply associated therewith). It will be recognized, however, that other types and "pin-outs" of connector or data/power interface may be substituted with equal success, dependent primarily on the host equipment with which the module must interface.

The equipment module 1500 of FIG. 15 may also be configured with a network data interface (described in detail below with respect to FIG. 19), thereby allowing the distribution of data to a plurality of different local and/or remote nodes for analysis, storage, or other functions.

Figure 16:
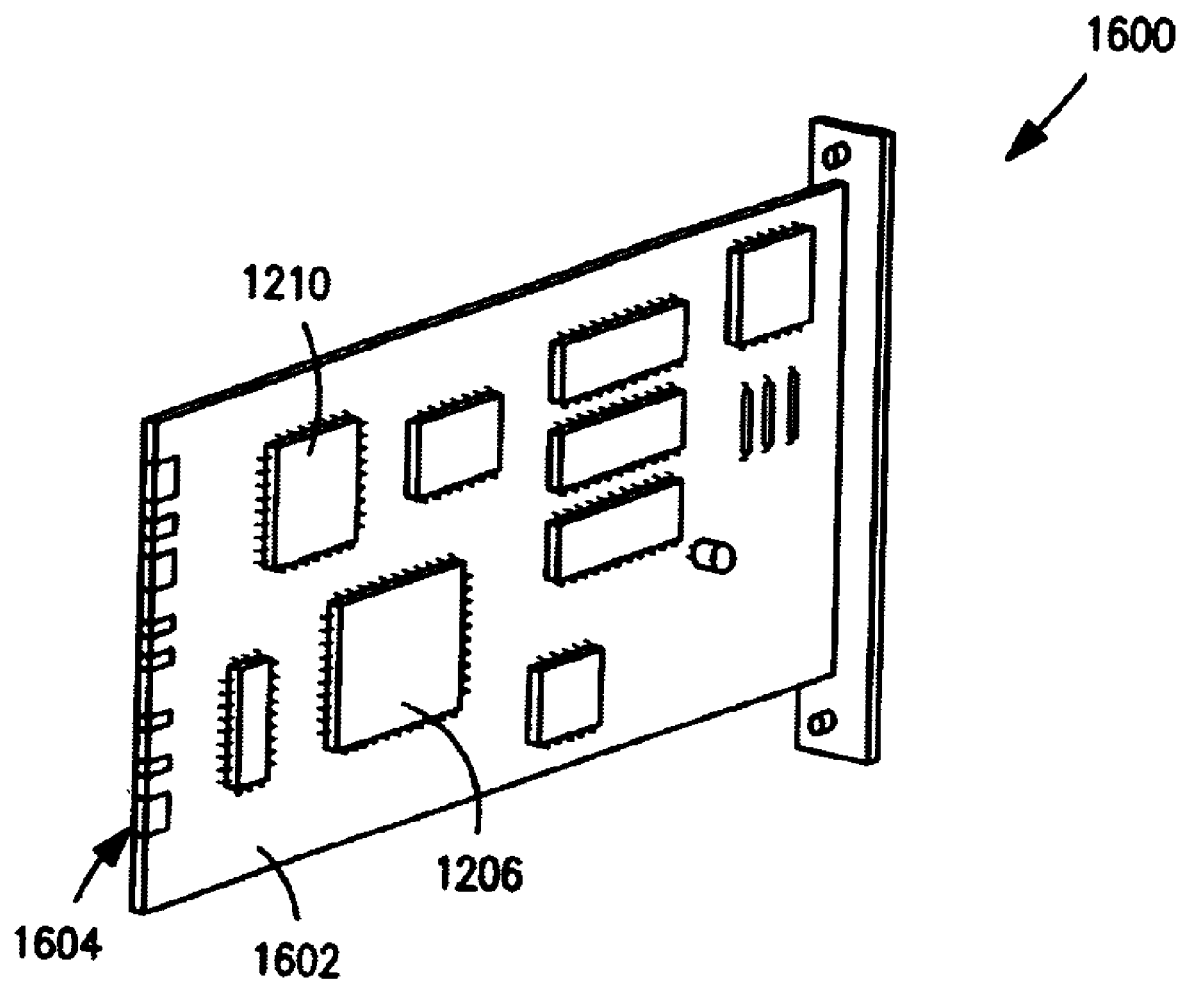
FIG. 16 is a perspective view of the module of FIGS. 12–14, configured as a plug-in circuit card for use within a host device.

FIG. 16 illustrates yet another embodiment of the ICG module of the invention, configured as a plug-in circuit card 1600 for use within a host device such as a dedicated stand-alone monitor or host monitoring device (e.g., one that has a primary function which may or may not be related to ICG or cardiography), personal computer, laptop computer, hand-held computer, minicomputer, or SUN UNIX workstation. The circuit card 1600 integrates all of the functionality of the embodiment of FIG. 1300, including processor and patient interface boards, onto one card substrate 1602. A standardized edge-type electrical connector 1604 is also provided to permit interface with the card receptacle of the host device (not shown), which may be configured according to any electrical interface standard (such PCMCIA, PC Card, or otherwise).

In yet another embodiment (not shown), the ICG module of the invention comprises a card generally similar to that shown in FIG. 16, except that the edge-type connector 1604 is replaced with a ribbon-cable and associated connector (or other type of connector) of the type well known in the electrical arts for interfacing the module with other circuit elements and boards within the host device. As yet another alternative, the ICG module may be plugged directly into another module within the host device. It will be recognized that literally any type of electrical interconnection scheme and protocol between the ICG module of the present invention (whether in "card" form as in FIG. 16 or otherwise) and the host device with which the module is used may be employed consistent with the invention.

FIGS. 17a–c illustrate yet another embodiment of the ICG module of the invention, configured as a "yoke" 1700 adapted for mobility and electrical interface with a monitoring device. As used herein, the term yoke is meant to include any configuration of mobile or transportable device which is used to facilitate centralization of a plurality of patient signals. In the present embodiment, the yoke 1700 is adapted to receive a plurality of electrical leads 1702 (whether as individual leads, in one variant, or as a single multi-terminal electrical connector 1708, in another variant) which are connected to the electrodes 1704 disposed on the thorax of the patient being monitored. The yoke 1700 is configured to be light weight and rugged, and utilizes a molded plastic impact-resistant housing 1706 of the type well known in the polymer arts, although other materials may be used. The yoke housing 1706 contains the electronics of the ICG module, including processor and patient interface boards (not shown), and further optionally includes an LED 1710 or other status indication for the ICG module. The output of the ICG module electronics in the yoke 1700 is transferred to the monitoring device (not shown) via a data interface 1712, in the present embodiment a universal serial bus (USB) connection and cable of the type well known in the electrical arts. This USB interface advantageously allows the yoke 1700 to interface data with any number of different types of devices, each of which include their own USB interface.

Alternatively, a wireless interface between the yoke 1700 and host monitor (or for that matter, between the yoke 1700 and the patient electrodes) may be used. For example, in one exemplary variant, an RF transceiver and modulator device are provided and adapted to generally comply with the well known "Bluetooth™" wireless interface standard. The Bluetooth "3G" wireless technology allows users to make wireless and instant connections between various communication devices, such as mobile devices (e.g., cellular telephones, PDAs, notebook computers, local or remote patient monitoring stations, and the like) and desktop computers or other fixed devices. The Bluetooth topology supports both point-to-point and point-to-multipoint connections. Multiple "slave" devices can be set to communicate with a 'master' device. In this fashion, the yoke 1700 of the present invention, when outfitted with a Bluetooth wireless suite, may communicate directly with other Bluetooth compliant mobile or fixed devices including a receiver disposed at the host monitor, or alternatively other Bluetooth-capable devices such as a cellular telephone, PDA, notebook computer, or desktop computer. Alternatively, WMTS telemetry may be utilized. The operation of the wireless interface is effectively transparent to the yoke 1700 and host monitor, although it will be recognized that data may be "buffered" within one or more intermediary storage devices (not shown) if desired.

Additionally, it will be recognized that for purposes of saving space within the yoke 1700, the signal processing and transceiver/modulator components of the interface may be embodied in a fully integrated "system on a chip" (SoC) application specific integrated circuit (ASIC) of the type generally known in the semiconductor fabrication arts (not shown). The SoC ASIC incorporates, inter alia, a digital signal processor (DSP) core, embedded program and data random access memories, RF transceiver circuitry, modulator, analog-to-digital converter (ADC), and analog interface circuitry necessary to support sampling, conversion, processing, and transmission of the cardiac output (or other) data to the host monitor's receiver.

Alternatively, a number of different subjects undergoing cardiac monitoring/analysis using the yoke 1700 of the present invention (or other comparable devices) may be monitored in real time at a centralized location using a single monitor receiver. Specifically, the monitor receiver (not shown) and transceiver are adapted to receive a plurality (currently seven, under prevailing Bluetooth architecture, although such number may be increased or decreased) of signals from remote ICG module devices, whereby the individual signals may be multiplexed or alternatively processed in parallel by the host monitor and interface (with the addition of appropriate multiplexing or parallel processing hardware of the type well known in the electronic arts). Hence, a host monitor configured to receive such multiplexed or parallel channel data may be used to monitor the cardiac output and other related parameters of multiple subjects at once.

Bluetooth-compliant devices, inter alia, operate in the 2.4 GHz ISM band. The ISM band is dedicated to unlicensed users, including medical facilities, thereby advantageously allowing for unrestricted spectral access. Maximum radiated power levels from the yoke's transceiver are in the mW range, thereby having no deleterious effect on the physiology of the subject due to radiated electromagnetic energy. As is well known in the wireless telecommunications art, radiated power from the antenna assembly (not shown) of the yoke transceiver may also be controlled and adjusted based on relative proximity of the transceiver, thereby further reducing electromagnetic whole body dose to the subject. The modulator of the yoke uses one or more variants of frequency shift keying, such as Gaussian Frequency Shift Keying (GFSK) or Gaussian Minimum Shift keying (GMSK) of the type well known in the art to modulate data onto the carrier(s), although other types of modulation (such as phase modulation or amplitude modulation) may be used.

Spectral access of the device may be accomplished via frequency divided multiple access (FDMA), frequency hopping spread spectrum (FHSS), direct sequence spread spectrum (DSSS, including code division multiple access) using a pseudo-noise spreading code, or even time division multiple access, depending on the needs of the user. For example, devices complying with IEEE Std. 802.11 may be substituted in the probe for the Bluetooth transceiver/modulator arrangement previously described if desired. Literally any wireless interface capable of accommodating the bandwidth requirements of the system may be used, such as the new WMTS biomedical band of 608–614 MHz. As yet another embodiment, an infrared device (e.g., Infrared Data Association "IrDA") may be substituted or even used in conjunction with the aforementioned wireless interface of the yoke.

Figure 18:
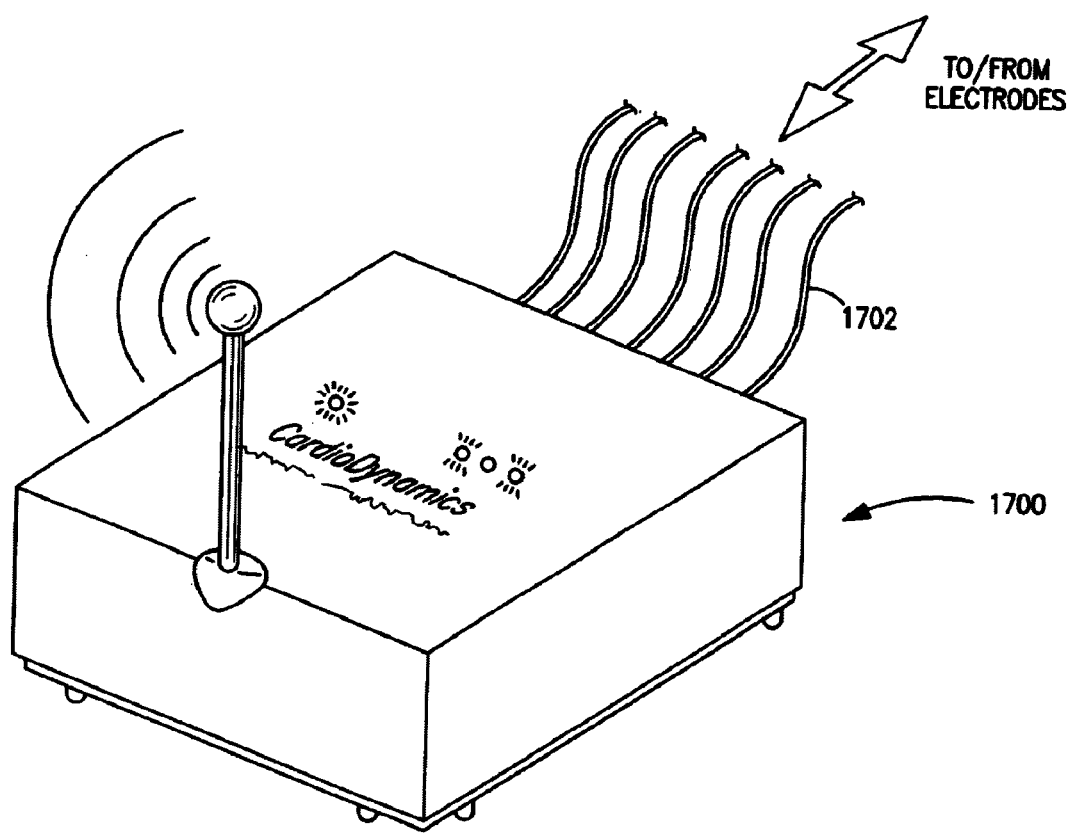
FIG. 18 is a perspective view of the yoke of FIGS. 17a–c, adapted for wireless communication with the monitoring device.

FIG. 18 is a perspective view of the yoke of FIGS. 17a–c, adapted for wireless communication with the monitoring device as just described.

Figure 19:
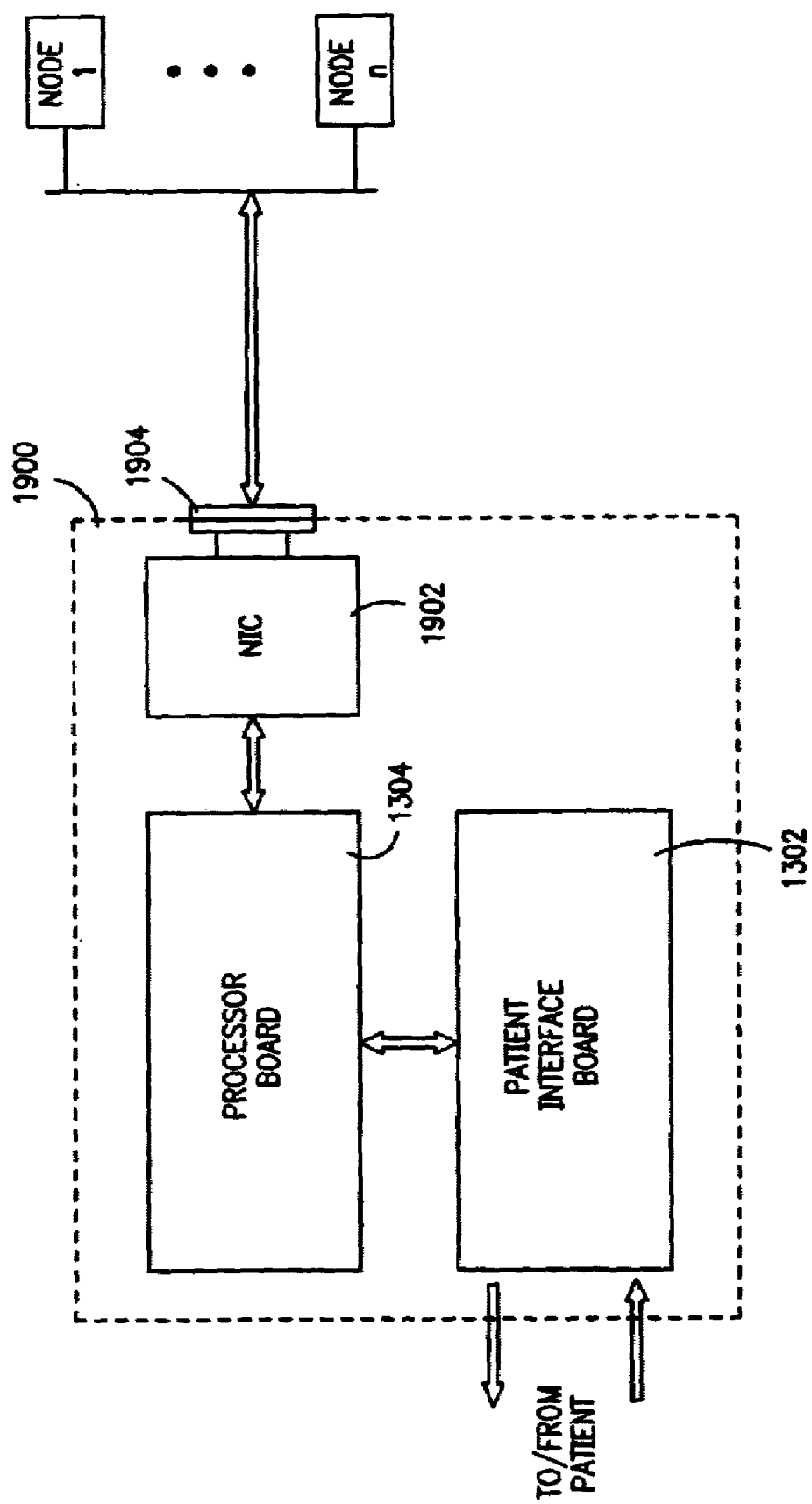
FIG. 19 is a block diagram of the module of FIGS. 12–14, including network interface and associated data network.

Referring now to FIG. 19, yet another embodiment of the ICG module of the invention is described, wherein the module 1900 is fitted with a network interface device 1902 (e.g., LAN card) and associated data network connector 1904. The network interface card 1902 and connector 1904 (including attendant NIC software running on the ICG microprocessor 1206) allow the cardiac output and other data generated by the module to be transferred to one or more remote nodes, such as the various stations of a local area network or wide area network. The network interface device 1902 in the present embodiment comprises an IEEE 802 Ethernet card adapted for packetized data transfer, although it will be recognized that any number of different network hardware environments (including, e.g., X.25, Token Ring, SONET, FDDI, Gibagbit Ethernet, or ATM) and protocols (e.g., TCP/IP, RTP, or FTP) may be utilized. In another embodiment (not shown), the ICG module may be outfitted with a modulator/demodulator apparatus of the type well known in the data communication arts, or DSL, ADSL, or DOCSIS device. I can't remove the page break-!Literally any data network device, including satellite uplink/downlink, can be used for transferring cardiac data to/from the ICG module consistent with the invention.

Input Vector Selection

The ICG module of the present invention includes provision, via the aforementioned patient board 1302, for receiving a plurality of input signals ("vectors") that may be used in the cardiac output determination. These input vectors typically include ECG signals that are derived, for example, from the various ICG/ECG electrodes disposed on the subject's body. Alternatively, such signal sources may comprise one or more other modules or devices. Regardless of source or type of signal, these input vectors may vary significantly in terms of signal quality and/or continuity. Therefore, the present invention is advantageously adapted to automatically (and continuously, if desired) analyze and arbitrate between the various input vectors based on their relative attributes (e.g., signal quality). This feature of the invention is now described in detail with respect to FIGS. 20–22.

As previously described with respect to FIG. 13, the ECG vector of the ICG module is selected using a vector select multiplexer 1315. In the embodiment of FIG. 13, the vector is selectable from a plurality of electrode pairs located at various points on the thorax of the subject, as shown in Table 5 below:

TABLE 5

| Vector | ECG Channel |
|---|---|
| 1 | EF |
| 2 | CF |
| 3 | DF |
| 4 | ED |

Figure 20:
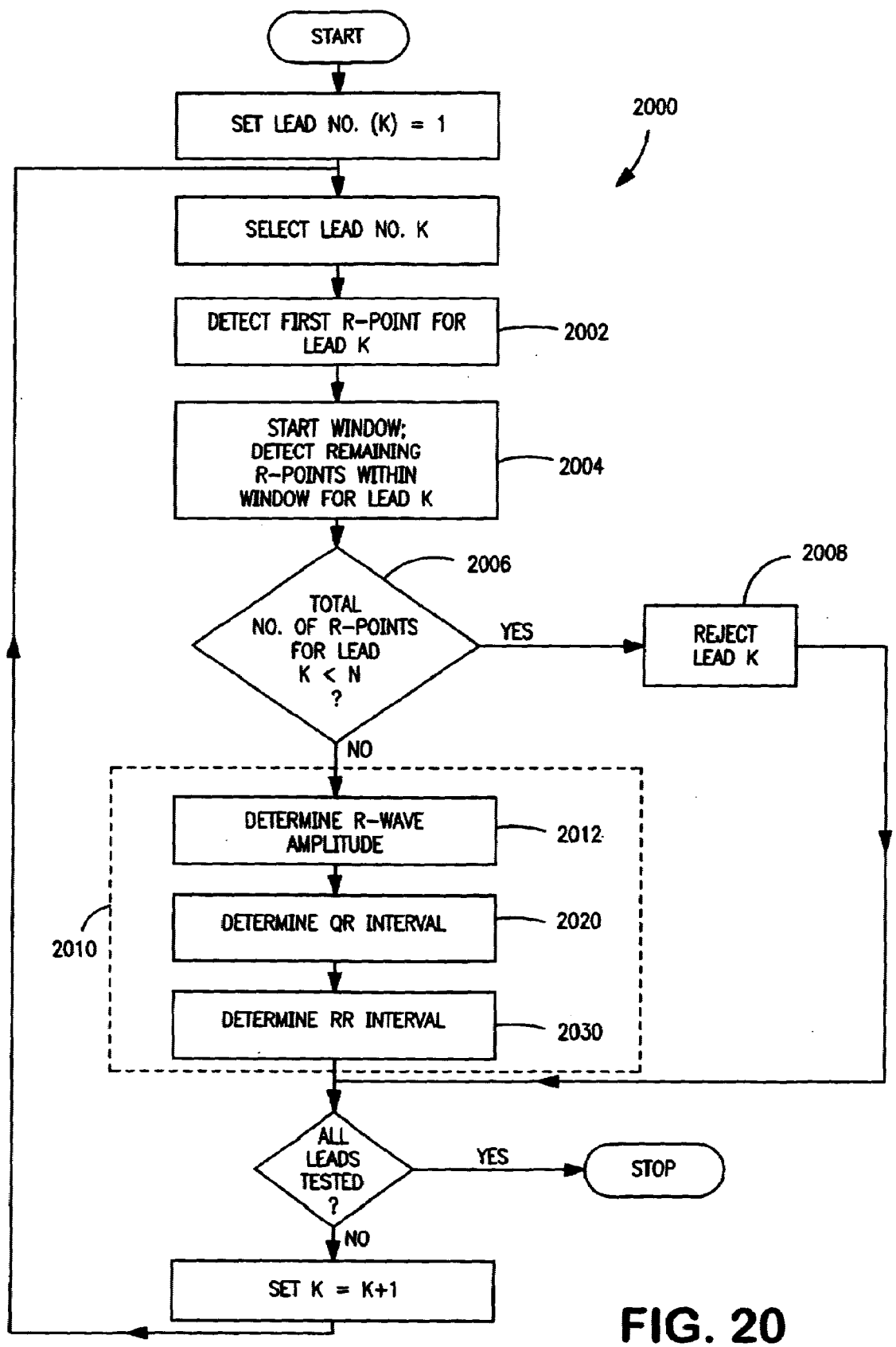
FIG. 20 is a logical flow diagram illustrating the methodology of auto-parameter (e.g., ECG) vector selection according to the invention.

FIG. 20 illustrates the methodology of ECG vector selection. It will be recognized that while the following discussion is drawn with respect to a plurality of ECG input vectors, other types of signals may be analyzed and arbitrated using the methodology of the invention. In the first main step 2004 of the method of vector selection 2000, each electrical lead providing a signal input is tested within a predetermined (e.g., six second) time window, beginning at the first detected R point (step 2002) in the input vector under analysis. If the total number of R points detected within the window is less than a given value n (e.g., 4) per step 2006, the lead is rejected per step 2008.

Figure 20A:
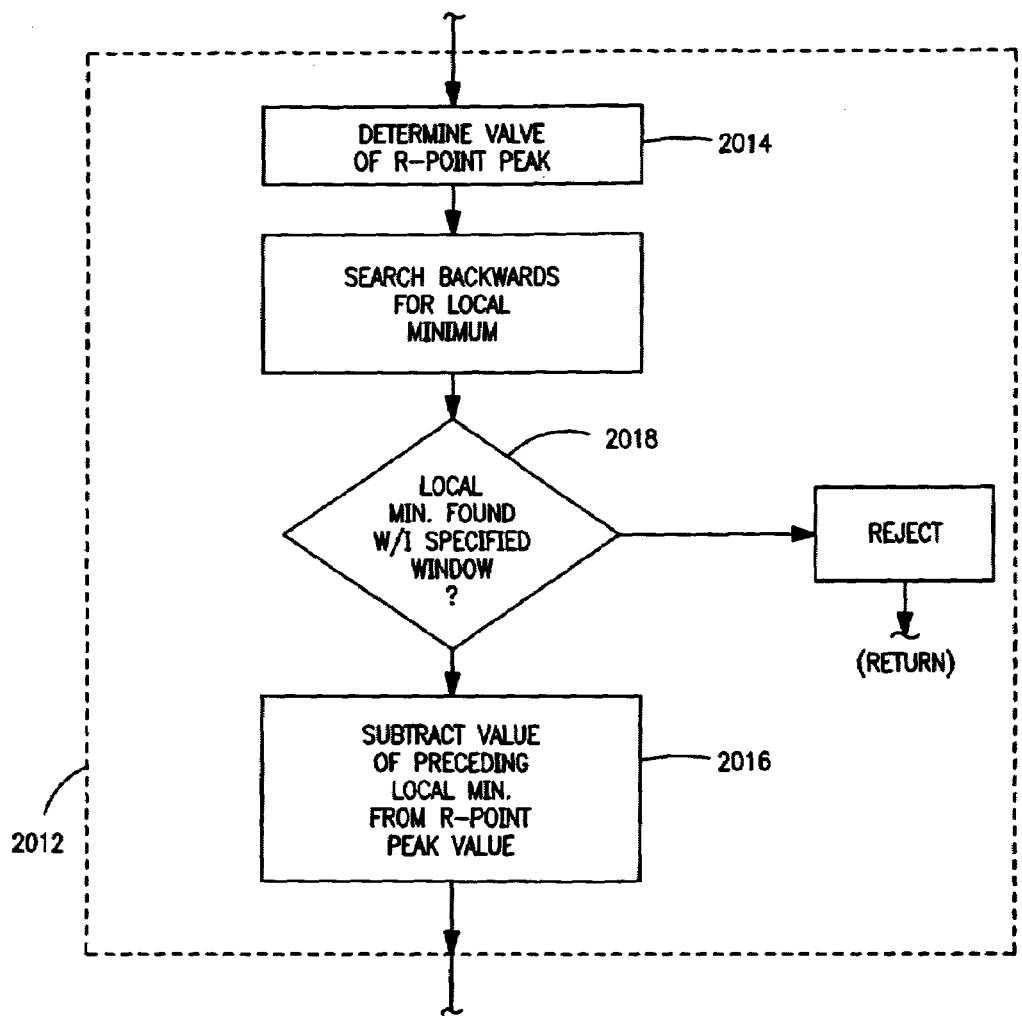
FIG. 20a is a logical flow diagram illustrating one exemplary method of determining the R-wave amplitude factor.

Additionally, each lead is evaluated per step 2010 of the present method 2000 based upon three factors: (i) R-wave magnitude, (ii) QR interval difference, and (iii) RR interval difference. R-wave magnitude (RM) is the peak-to-peak magnitude of the R point, which is calculated per step 2012 as shown in FIG. 20a by taking the value of the R peak (step 2014) and subtracting the value of the preceding local minimum (step 2016). If there is no local minimum found within a "back" sample or temporal window of a given size (e.g., 80 samples) per step 2018, the R point is rejected. FIG. 21 illustrates the calculation process graphically in terms of a typical QRS complex.

Figure 20B:
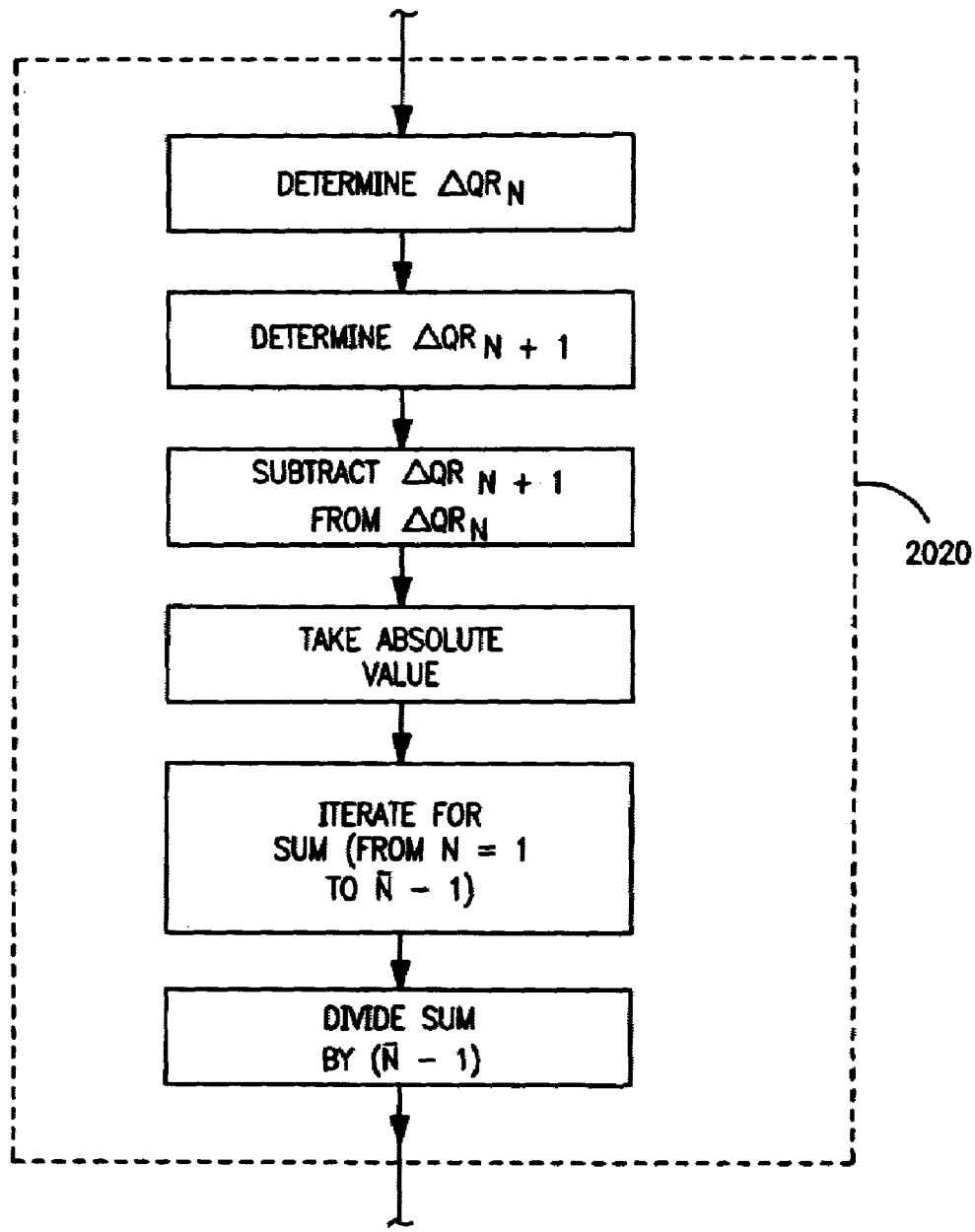
FIG. 20b is a logical flow diagram illustrating one exemplary method of determining the QR interval difference ($QR_{score}$) factor.
Figure 20C:
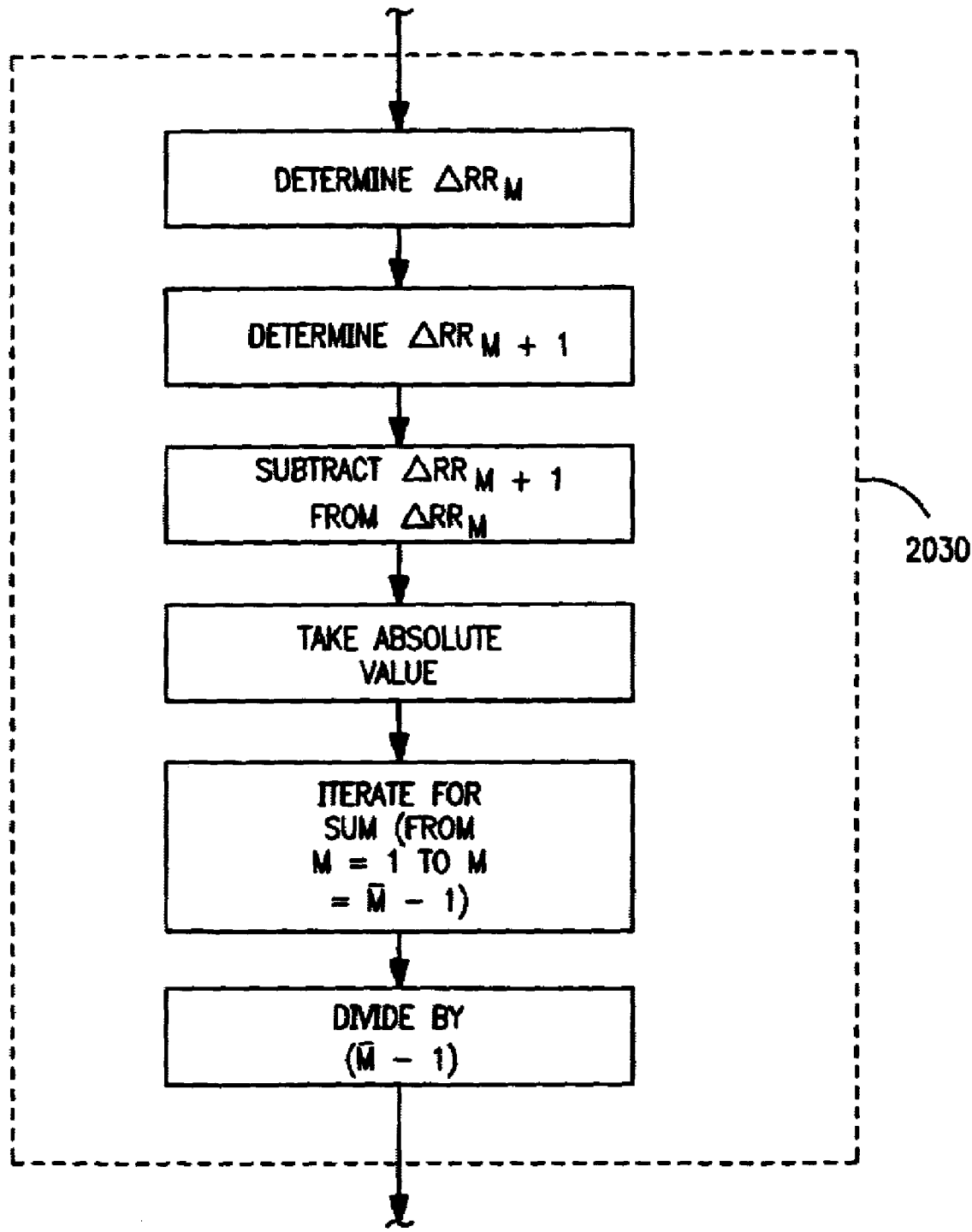
FIG. 20c is a logical flow diagram illustrating one exemplary method of determining the RR interval difference ($RR_{score}$) factor.

Next, the QR interval difference ($QR_{score}$) and the RR interval difference ($RR_{score}$) are determined per steps 2020 (FIG. 20b) and 2030 (FIG. 20c), respectively, as follows.

1. QR Interval Difference Score ($QR_{score}$)—The QR interval difference score is used to identify variability of feature detection within the QRS complex. This factor measures the time difference between the Q point and the R point, and compares this value to all other values detected within the given time window. FIG. 22 illustrates this process graphically (along with that of the R to R interval difference calculation, described below). Eqn. 5 defines this relationship mathematically:

$$QR_{score} = \frac{\sum_{n=1}^{N-1} \text{ABS}(\Delta QR_n - \Delta QR_{n+1})}{N-1}; \quad \text{(Eqn. 5)}$$

Where N=the number of R points detected within the selected time window, and $\Delta QR_n$ is the time from the Q point to the R point for the nth QRS complex detected.

2. RR Interval Difference Score ($RR_{score}$)—The RR interval difference score is used primarily to identify variability of detection between QRS complexes. This factor measures the time difference between one R point to the next R point. FIG. 22 illustrates this process graphically. Eqn. 6 defines this relationship mathematically:

$$RR_{score} = \frac{\sum_{m=1}^{M-1} \text{ABS}(\Delta RR_m - \Delta RR_{m+1})}{M-1}; \quad \text{(Eqn. 6)}$$

Where M=the number of QRS complex intervals detected within the selected time window, and $\Delta RR_m$ is the time from one R point to the next R point in the nth interval.

Each lead factor is also optionally normalized, to between 0 and 1 in the illustrated embodiment. For RM, all of the lead magnitudes are divided by the maximum value among the leads. For the $QR_{score}$ and $RR_{score}$ values, the number are first inverted, and then normalized based upon the maximum value among the leads. In the event there is zero variability between QR intervals or RR intervals, the value are set to a small constant before inversion (or, alternatively, any other approach which accounts for the infinite value when inverting zero may be employed). For example, the Assignee hereof has determined that optimal values to be used during testing are 0.01 and 0.3125 for $QR_{score}$ and $RR_{score}$, respectively, although other values may clearly be substituted.

The lead (vector) choice is based upon the maximum value of the sum total of the three factors for each lead. The normalization and selection algorithm is given by Eqn. 7:

$$\underset{1\to 4}{\text{MAX}}\left\{\sum_{L=1}^{4}\left[\frac{RM_L}{\underset{1\to 4}{\text{MAX}}(RM)}+\frac{(QR_{score})_L^{-1}}{\underset{1\to 4}{\text{MAX}}((QR_{score})^{-1})}+\frac{(RR_{score})_L^{-1}}{\underset{1\to 4}{\text{MAX}}((RR_{score})^{-1})}\right]\right\} \quad \text{(Eqn. 7)}$$

where L is the lead number (arbitrarily assigned), and the function $$\underset{1\to 4}{\text{MAX}}(\ldots)$$

is the maximum value among the four leads. By default, the leads are ranked from best to worst as: Lead 2, Lead 3, Lead 1, and Lead 4. The default lead order is selected based upon an ideal mean electrical axis of the heart. Lead 2 should, theoretically, have the largest ECG amplitude because the electrical projection onto this lead is the greatest with the electrodes 'CF' used for the ECG. The other rankings are determined based upon this theory, using the expected relative voltage from the lead. If two or more leads have the same score, the lead is selected based upon this ranking system.

It will be appreciated that while a three-factor approach (i.e., R-wave amplitude, QR interval, and RR interval) is utilized, other types and number of factors may be substituted. For example, a two-factor summation of R-wave amplitude and QR-interval difference could be utilized. Furthermore, the quality determination need not rely on a summation; a mathematical factoring equation (i.e., where the individual quality factors or indexes are multiplied together to result in a single quality index) could be utilized with equal success. Many other such variations and permutations are possible consistent with the present invention, the embodiments illustrated herein being merely exemplary in nature.

Defibrillation Apparatus and Method

Referring now to FIGS. 23–30b, improved defibrillation apparatus and methods according to the present invention are described in detail.

In one aspect of the invention, an improved defibrillation apparatus and methods are disclosed which use impedance cardiography techniques for accurately determining if and when a countershock should be applied to the subject. This approach for determination of shockable and nonshockable rhythms, including VT and SVT, determines if significant and pulsatile cardiac output (blood flow through the heart) is present with each heartbeat. As previously discussed, this is a substantial improvement over the prior art, which at best generates significant errors in the shock/no-shock decision process, thereby potentially resulting in the application of unwanted shocks to a subject. In one exemplary embodiment of the apparatus, electrodes having predetermined spacing are utilized to ensure ICG waveform features are captured with sufficiently high resolution. Pacing spike detection is implemented to prevent misclassification of pacing spikes as R points. A wavelet algorithm for efficient R point detection during arrhythmias is also used in conjunction with the foregoing. A wavelet transform is a time-scale representation of an input signal that is obtained by filtering the signal with a wavelet or scaling function at a particular scale. Various wavelets and scaling functions are utilized as part of the invention to emphasize certain features of interest associated with the input impedance and/or ECG waveforms obtained from electrodes positioned on the subject's thorax. The resulting emphasized feature in each wavelet transform is then detected to obtain a fiducial point (e.g., B, C, X for the impedance waveform, and R for the ECG waveform). By virtue of its transformation to the time-scale domain, this wavelet method is more resistant to noise artifact than empirical waveform processing in the time domain. Furthermore, no absolute thresholds are used for R, B, C, or X point detection in the exemplary embodiment, which increases the ability of this algorithm to generalize among waveforms from the cardiac patient population. The use of a decision model not constrained to discrete values or absolute thresholds (e.g. a fuzzy logic model) ensures that the decision module is capable of such generalization. With efficient beat detection, the variability of B point and X point samples can also advantageously be determined with higher certainty.

In the exemplary embodiment (FIG. 23), the foregoing functionality is provided in the form of an apparatus 2300 comprising and ICG module 2302 (such as for example that previously described herein with respect to FIG. 12) that communicates with an external defibrillator module 2304. Using electrodes 2306 proximate to the subject, waveforms generated by the cardiac cycle are monitored.

Figure 24A:
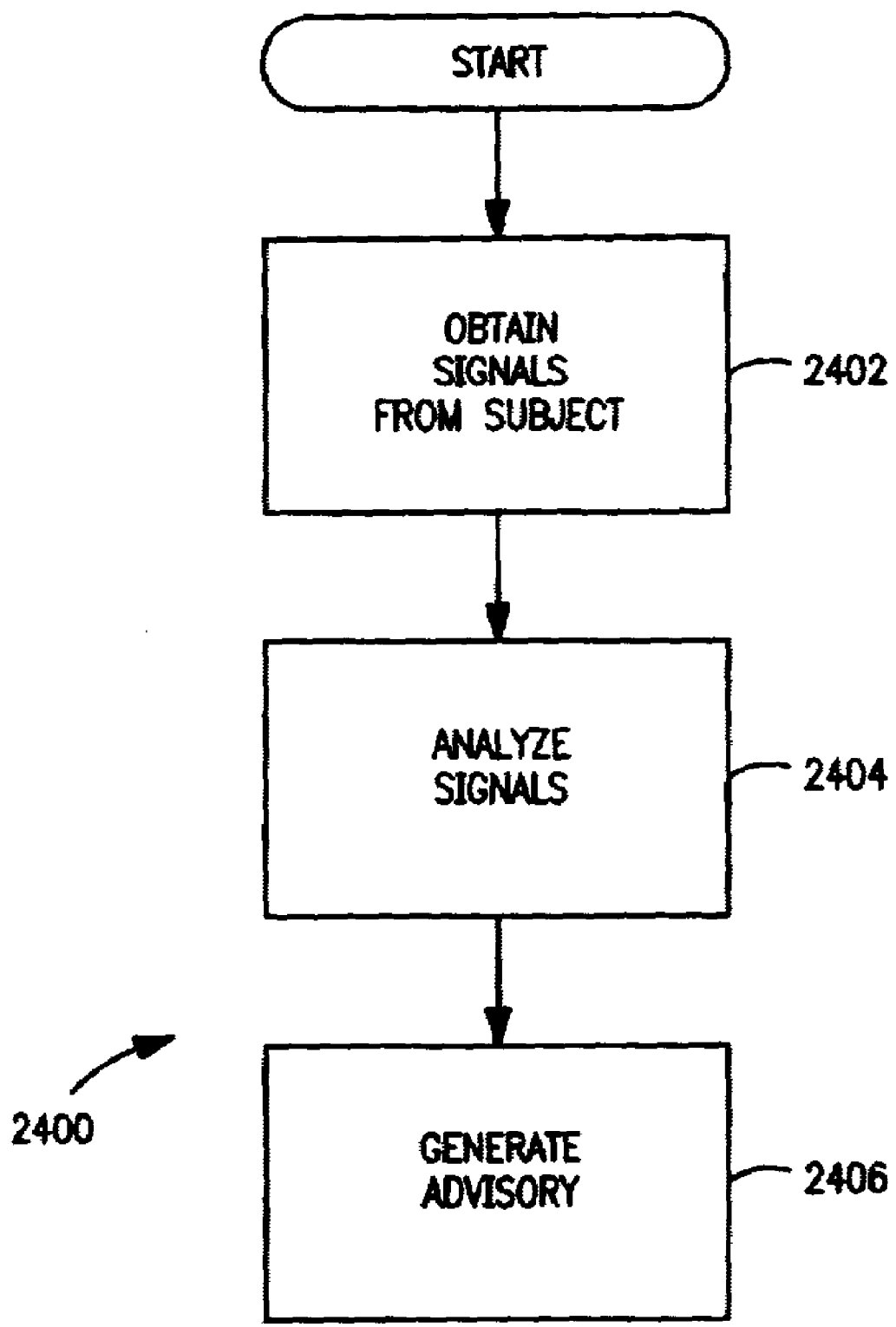
FIG. 24a is logical flow diagram illustrating the general method of signal analysis according to the invention.
Figure 25:
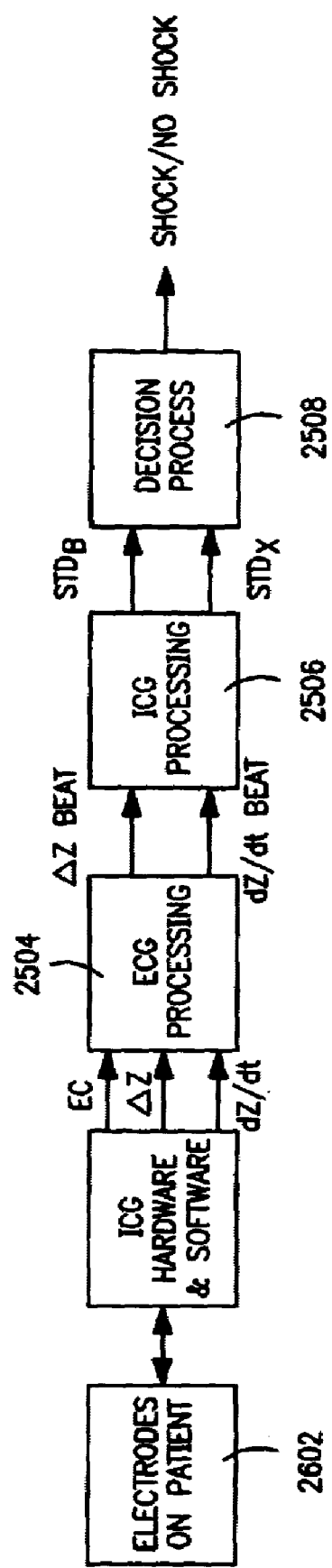
FIG. 25 is functional block diagram illustrating an exemplary signal processing architecture used within the apparatus of FIG. 24.

As with other ICG applications, ECG and ICG waveforms are in the illustrated embodiment acquired from the hardware 2502, with subsequent software processing performed to analyze and extract the desired information, as illustrated in the exemplary method 2400 of FIG. 24a and the block diagram of FIG. 25. In general, the method 2400 of the present invention comprises first obtaining signals from the subject containing information relating to the cardiac function of the subject (step 2402). Next, these signals are analyzed in terms of multiple parameters per step 2404. Information generated by the analysis of step 2404 is then used as input to a decision process, the latter evaluating the inputs to perform an advisory function and/or generate a control signal (step 2406) as described in greater detail subsequently herein.

Figure 24B:
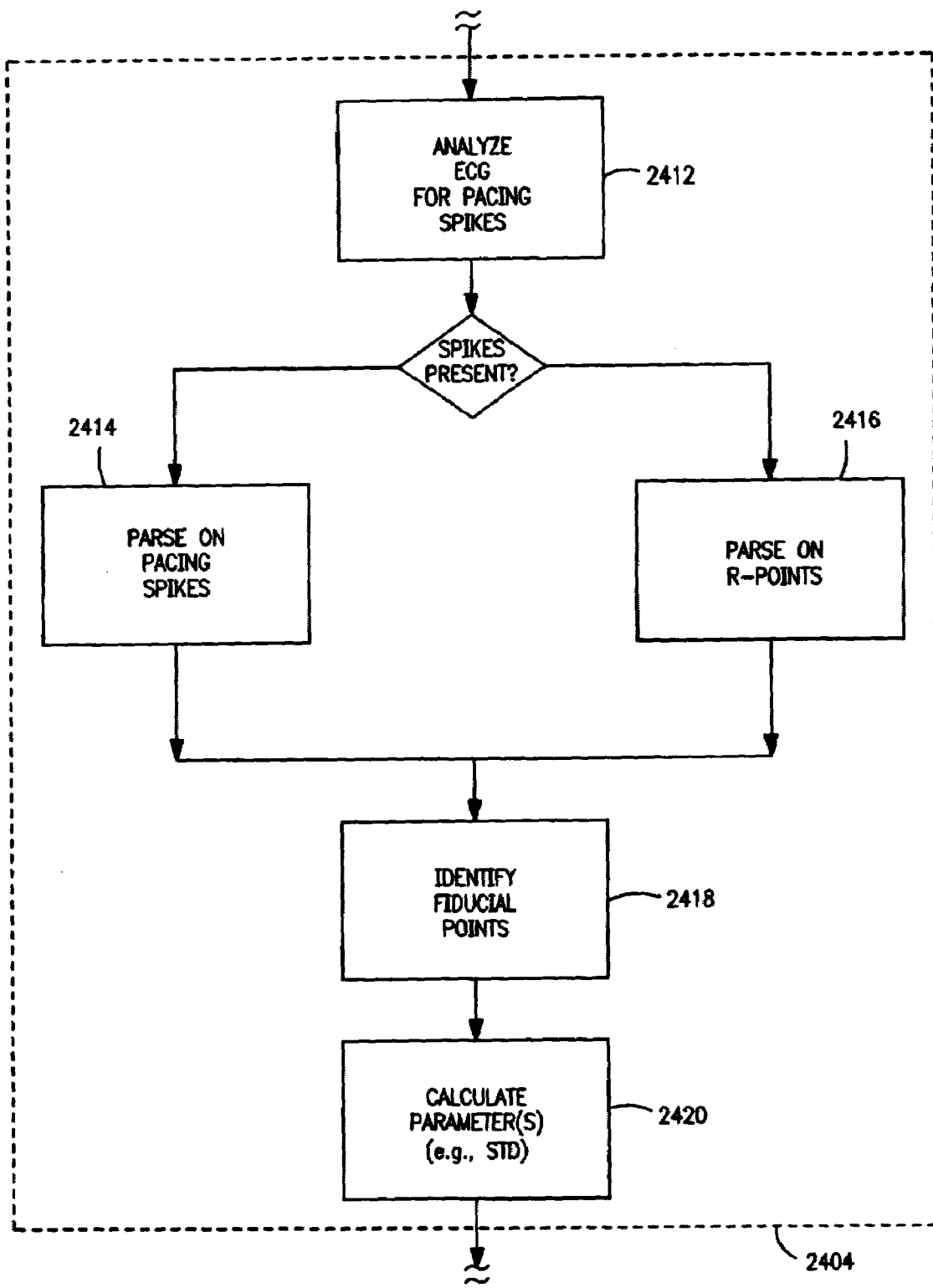
Figure 24C:
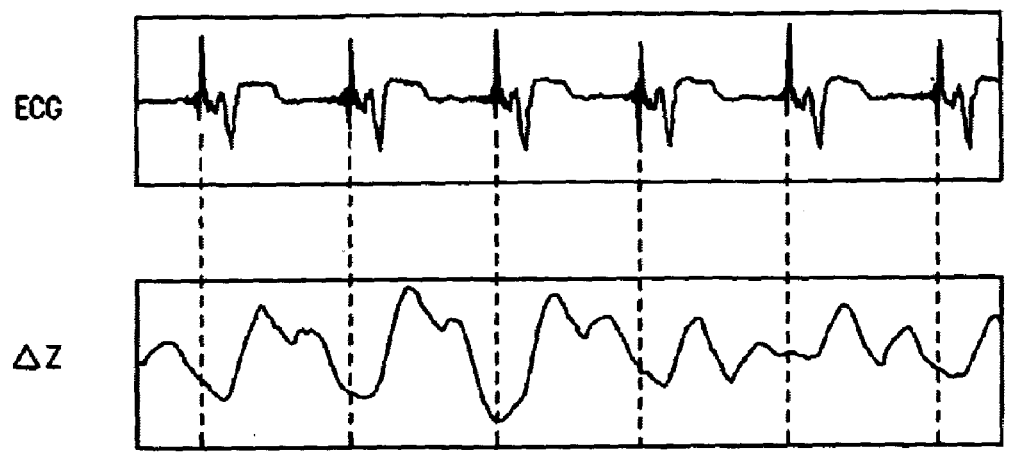
FIGS. 24c and 24d illustrate exemplary beat parsing based on pacing spikes and R points, respectively.
Figure 24D:
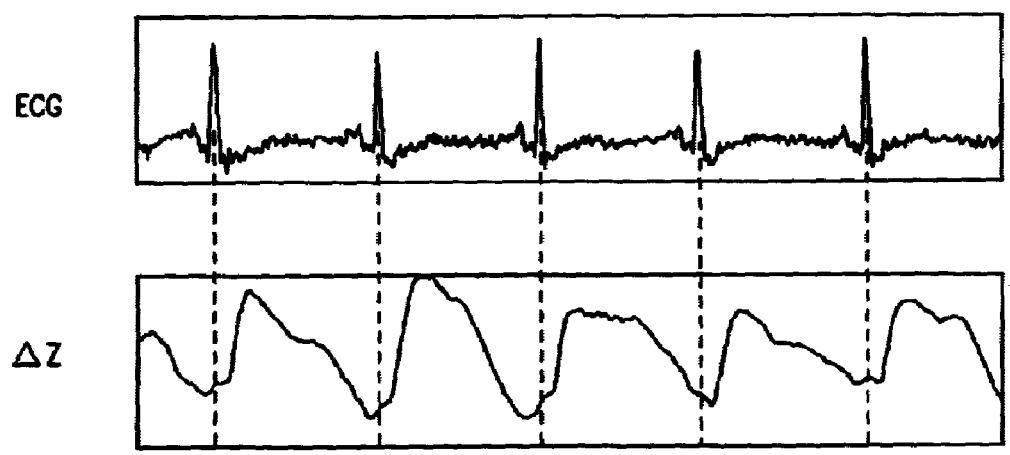
Figure 24E:
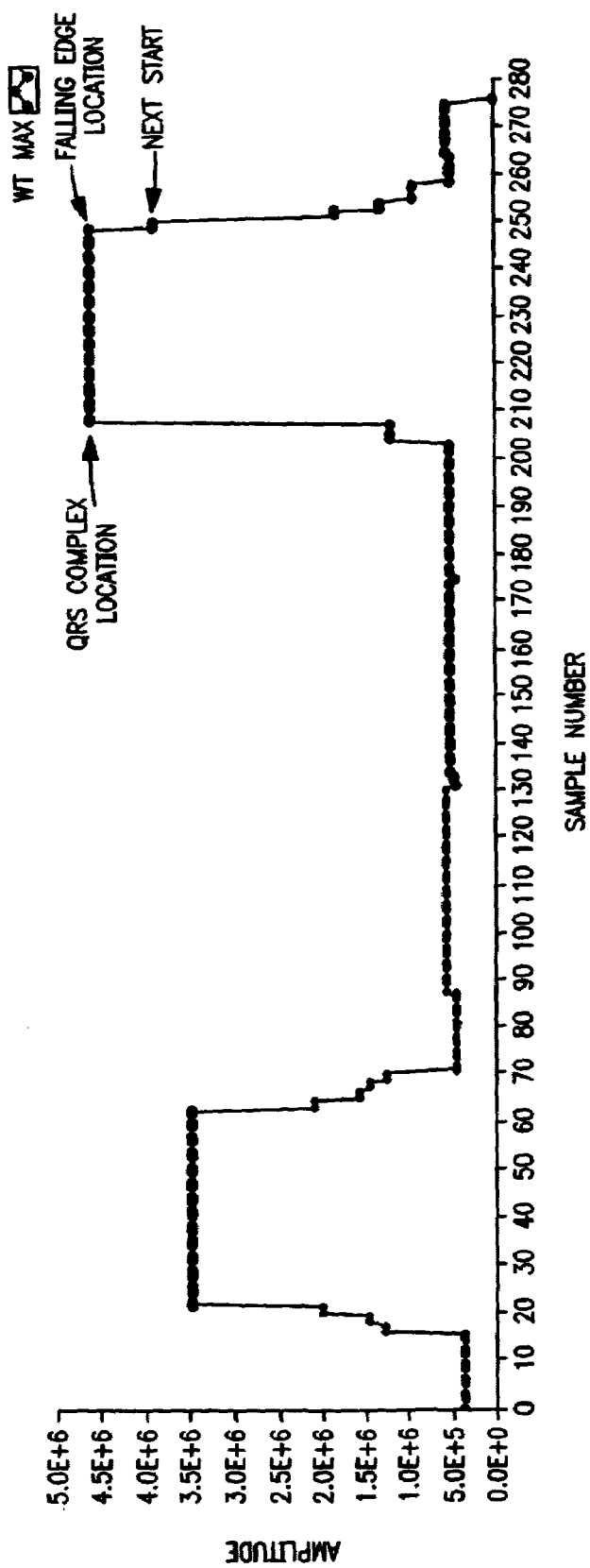
FIG. 24e graphically illustrates an exemplary QRS complex location search methodology according to the invention.

FIG. 24b illustrates one exemplary embodiment of the analysis (step 2404) of the foregoing method 2400. Specifically, in this embodiment, the ECG is first analyzed for pacing spikes or R points (step 2412). If pacing spikes are detected, then the ΔZ and dZ/dt waveforms are parsed into individual beats according to a first criterion (step 2414). In one variant, parsing into individual beats of ΔZ and dZ/dt occurs based on the pacing spikes. If pacing spikes are not detected, then the ΔZ waveforms are parsed according to a second criterion, such as for example detected R points (step 2416). See for example FIGS. 24c and 24d, which illustrate beat parsing using pacing spikes and R points, respectively. Within each beat, a plurality of fiducial points (e.g., two), such as the B (aortic valve opening) and X (aortic valve closing) points, are determined (step 2418). Over several beats, the standard deviations of the fiducial point sample locations are calculated (step 2420). These standard deviations are input to a decision process 2508 (described in greater detail below) as shown in FIG. 25; when the standard deviations meet certain criteria (such as, for example, the values of the standard deviations being sufficiently large in magnitude), the heart may be unable to pump blood in a coordinated fashion, as the aortic valve openings and closures are highly variable. In the exemplary embodiment, these high standard deviations cause the decision process 2508 to output a recommendation per instruction 2510 to shock the subject.

A constant current source such as that previously described herein is used in conjunction with the exemplary ICG apparatus 2300. In traditional (non-defibrillation) applications, this current splits as it is administered to both sides of the body. In the present embodiment of the defibrillation apparatus, current is administered across the thorax to the outer dual electrodes, and the resulting voltage is measured across the inner dual electrodes. The signals are demodulated and digitized in hardware, and are then processed in software through filters and a derivative calculation to obtain ECG, ΔZ, and dZ/dt waveforms.

Figure 26B:
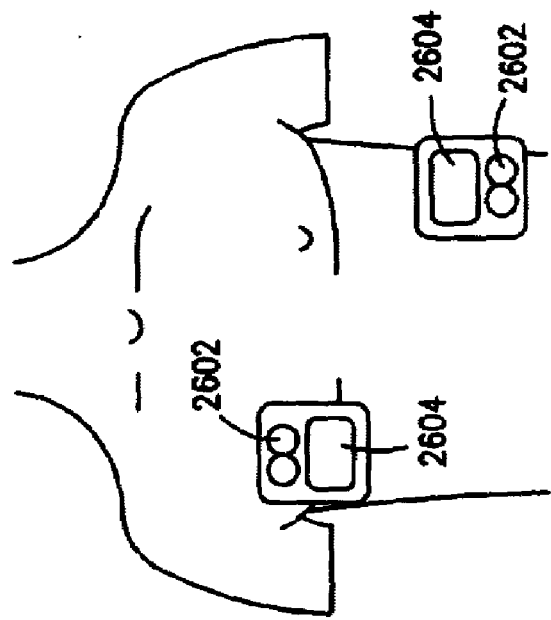
FIG. 26b is a graphical illustration of a second exemplary electrode configuration according to the invention, the defibrillation and ICG electrodes being integrated into substantially unitary structures.
Figure 26A:
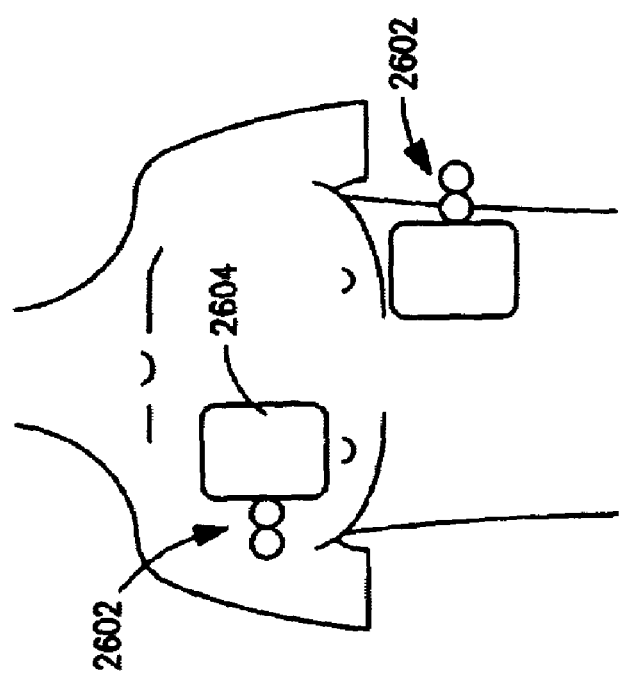
FIG. 26a is a graphical illustration of a first exemplary electrode configuration according to the invention, the defibrillation and ICG electrodes being physically separate.
Figure 27:
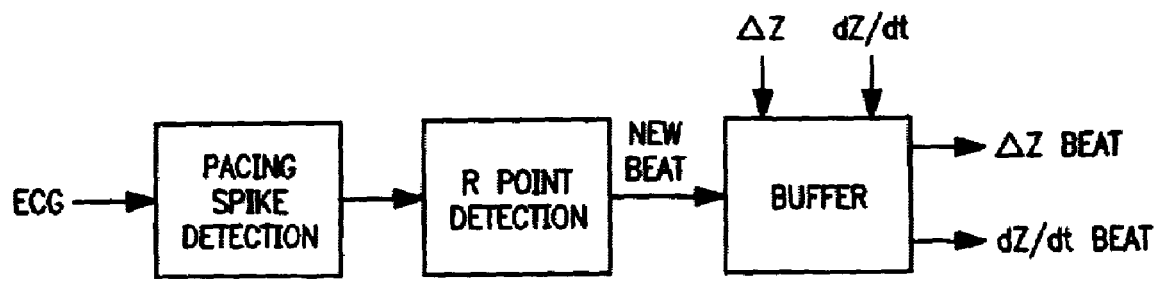
FIG. 27 is a functional block diagram illustrating an exemplary ECG processing module architecture used with the apparatus of FIG. 24.

To facilitate use with AEDs, one embodiment of the apparatus 2300 uses a specialized electrode configuration. For example, as previously described herein, two sets of "dual" electrodes may be used, with an ICG measurement made on the left and right sides of the subject's thorax and later averaged (see FIG. 3a). In the exemplary embodiment of the defibrillation apparatus of the present invention, one set of dual electrodes is used to make one ICG measurement, with each dual electrode being physically localized with a defibrillation electrode. One embodiment of localized ICG/defibrillation electrodes comprises disposing the two electrodes (ICG 2602 and defibrillation 2604) adjacent each other, as shown in FIG. 26a. This embodiment has the advantage of allowing standard size defibrillation electrodes to be used, while maintaining predetermined spacing between dual ICG electrodes. In another embodiment, the gel areas within the defibrillation electrodes 2604 are modified so that the patient contact area contains gel areas for both defibrillation electrodes and ICG electrodes 2602 (FIG. 26b), thereby effectively "merging" the two sets of electrodes into a unitary structure. This latter embodiment has the advantages of maintaining a constant uniform spacing (thereby increasing repeatability), as well as enhanced ease of operation in that placing of both defibrillation and ICG electrodes occurs simultaneously.

Still other configurations of ICG and defibrillation electrode may be used consistent with the invention, such other configurations being readily fabricated by those of ordinary skill provided the present disclosure. For example, both defibrillation and ICG electrodes may be integrated into a unitary structure, such as a flexible non-conductive band which when positioned on the subject's thorax properly positions each electrode and ensures sufficient contact with the skin.

As yet another alternative, each unitary electrode structure could contain one defibrillation gel area and only one ICG gel area. In this configuration, the ICG gel area would be used for current stimulation and the defibrillation gel area would be used for ICG monitoring and (with a hardware relay used to switch circuitry) defibrillation shock. The ICG gel and defibrillation gel areas would possess predetermined spacing.

In the exemplary embodiment, the spacing between individual terminals of the dual ICG electrode 2602 is predetermined or controlled. The Assignee hereof has found that a spacing on the order of 5 cm works well in many cases, although it will be recognized that other spacings (whether fixed or variable) may be substituted. In practice, the terminal spacing determines the depth of sampling in impedance calculations; hence, it is often critical that this spacing remain constant during individual subject measurements and across all patients. It is noted that the typical defibrillation electrode generally cannot alone be used as a sensing electrode for the ICG measurement since its large size dictates a terminal spacing (such as to a single terminal ICG electrode placed near the defibrillation electrode) much larger than that frequently optimal for ICG measurement (e.g., 5 cm), thereby resulting in a low signal-to-noise ratio (SNR) and hence poor ICG performance. It is feasible, however, to implement the present invention with a very small form factor defibrillation electrode and a second ICG electrode placed nearby (i.e., within the prescribed distance discussed above), consistent with not exceeding a maximum allowed electrical current density during shocking (which may, for example, result in burning or other tissue damage to the subject being shocked) or other similar limitations associated with defibrillation electrode/paddle size. Alternatively, large (conventional) form factor defibrillation electrodes may be used without optimal spacing if low SNR/performance is acceptable or compensated for in another fashion.

It will be recognized, however, that in prior art approaches in which only the defibrillation electrodes were used to obtain ICG waveforms (i.e., ICG stimulation and sensing, as well as defibrillation countershock from the same electrodes), significant waveform features were lost, even during normal sinus rhythm. The lack of any spacing between the stimulation and sensing electrodes resulted in shallow sampling of the impedance waveform, with loss of pulsatile information. See Johnson, et al., "The transthoracic impedance cardiogram is a potential haemodynamic sensor for an automated external defibrillator", *Eur Heart J*, 19:1879–1888, 1998.

In the exemplary embodiment of the present invention, the ECG wave form obtained from the subject (or intermediary device) is processed in the ECG "module" 2504 (FIG. 25) to detect artifacts. As used herein, the term "module" may comprise a physical device or component within the ICG module 2302 of the apparatus 2300 of FIG. 23, or alternatively a "virtual" module, such as in the case of where the signal processing performed by the module is distributed across a number of different components or software processes, and/or distributed temporally. Hence, the term module should in no way be considered limiting with respect to any particular configuration, arrangement, or sequence.

One such exemplary artifact detected by the ECG module 2504 comprises pacing spikes, with detection according to the methodologies set forth in co-owned and co-pending U.S. patent application Ser. No. 10/329,129 filed Dec. 24, 2002 and entitled "Method and Apparatus for Waveform Assessment", which is incorporated by reference herein in its entirety. If one or more (e.g., two) pacing spikes are present between QRS complexes, the most recent spike is used to parse the next beats of ΔZ and dZ/dt. The parsed ΔZ and dZ/dt beats are transmitted for further processing (See FIG. 27). If a spike is not present, then R point detection is conducted, with the detected R point used to parse the next beats. Exemplary methods of R point detection useful with the present invention are described in co-owned and co-pending U.S. patent application Ser. No. 09/764,589 filed Jan. 17, 2001 and entitled "Method and Apparatus for Hemodynamic Assessment including Fiducial Point Detection" which is incorporated by reference herein in its entirety, with the exception that these methods are ideally adapted to detect arrhythmic R points with enhanced accuracy for the present invention. Specifically, in the exemplary configuration of FIG. 27, the R point detection methodology is adapted in four (4) aspects. First, rather than a single threshold for QRS complex detection, two thresholds are used. A first threshold (such as for example 10% of the max value of the preceding 300 samples) is provided, and a second threshold (such as for example 27.5% of the previous QRS complex amplitude in the wavelet test value signal) is also provided. In one variant, the larger of the two values is used for beat detection, although it will be recognized that more sophisticated analytical methods relating to the two (or more) thresholds may be implemented, such methods being readily implemented by those of ordinary skill provided the present disclosure.

Second, the maximum value window for detection of a QRS complex is set at 40 samples. This number may be varied, however, based on the desired application and other factors.

Third, rather than only looking for the R point in the time domain, the instant embodiment first isolates the R point in the wavelet test value signal in a sample "window" (e.g., 50 samples) around the QRS complex location. Once this isolation is performed, the maximum absolute value of the ECG in another sample window (e.g., 7 samples) around this point is marked as the R point.

Lastly, the next sample to begin looking for a QRS complex location is set to the falling edge of the QRS complex window. This is the first sample that is less than the maximum value of the wavelet test value window that contains the QRS complex. Specifically, in the illustrated embodiment, the WT_max signal (the signal having the maximum value of the previous 40 samples) is used to establish an upper bound. This in effect generates a "box" in the signal around a QRS complex, where the left-hand corner of the box comprises the QRS complex location. When the first sample having a smaller magnitude than that corresponding to the top (upper bound) of the box is encountered, the search for another QRS complex is performed. This first smaller magnitude sample is referred to as the "falling edge", because the signal starts declining towards 0 until the baseline between beats is reached. This concept is graphically illustrated in FIG. 24e. The following parameters are also specified in the exemplary embodiment:

1) Falling_edge(m)—QRS window falling edge:

$m \in [0, \ldots, M]$, M+1=number of QRS complexes

The offset of the QRS window, Falling_edge(m), is designated as the first sample after Rising_edge(m) that satisfies Eqn. 8:

$$w_T(k) > w_T(k+1) \qquad \text{(Eqn. 8)}$$

2) $x_{start}(k)$—Next start sample:

x(k) is the sample number to begin looking for next QRS complex. The next start sample shall be the first sample after the Falling_edge(m), or $x_{start}(k)$=Falling_edge(m)+1.

Figure 28:
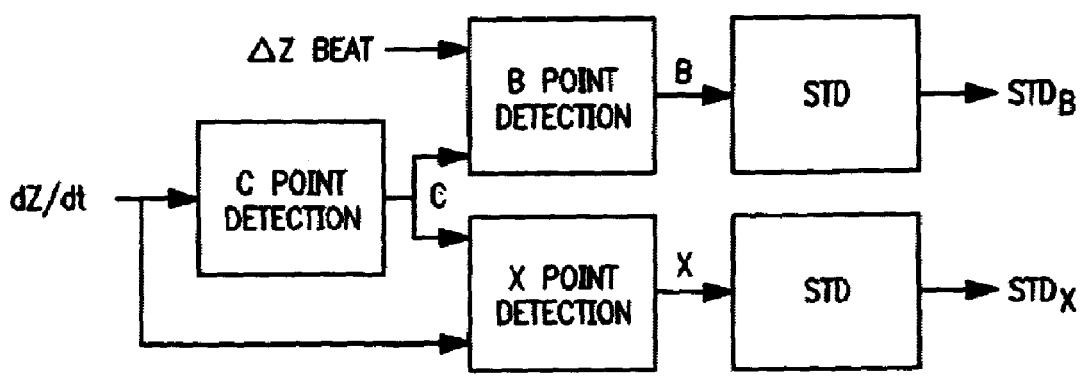
FIG. 28 is a functional block diagram illustrating an exemplary ICG processing module architecture used with the apparatus of FIG. 24.

As shown in FIG. 25, ICG processing is performed in the exemplary embodiment subsequent to the ECG processing previously described via an ICG "module" 2506. ICG processing in this embodiment is shown in FIG. 28, wherein the ICG B and X points are processed as described in U.S. patent application Ser. No. 09/764,589 previously incorporated herein. Specifically, the C point is found first, which limits the detection range for subsequent B and X point detection. The standard deviations of several (e.g., 10) B and X point sample locations, $STD_B$ and $STD_X$, respectively, are then calculated on an ongoing basis; see FIG. 28. It will be recognized, however, that statistical or non-statistical parameters other than STD may be used consistent with invention, including for example variance ($\sigma^2$), skewness, or any other parameter indicative of the variation of B and/or X point locations.

The foregoing standard deviations (STDs) generated from the ICG processing are input to the decision module 2508 (see FIG. 25) which, as the name implies, aids in the decision of whether to shock the subject or not. Such decision may be used as the basis for automatic shock initiation, purely as an advisory, or any combination thereof. For example, the present invention contemplates an optional advisory function wherein the results of the decision-making process are presented to the operator, with a "go/no-go" supervisory function requiring positive operator assent before countershock is initiated (so-called "semi-automatic" mode). As yet another alternative, upon the decision module 2508 generating an affirmative countershock decision, the apparatus may be configured to simply forewarn the operator of impending countershock delivery, such as by visual and/or audible warning, countdown timer, etc.

Such shock/no-shock decisions may also be further analyzed if desired, such as through averaging or statistical analysis. As a simple example of the latter, consider where a plurality of decisions output from the decision module 2508 for a single patient, such as for example, those generated sequentially through iterative sampling are applied to a logic module (not shown), such that a required coincidence is implemented (e.g., 2 of 3 "decisions" produced by the decision module for that subject must indicate shock for shock to be administered). Alternatively, the decision module output may act as an input to further downstream processing, which may take into account other factors relating to that particular patient, a larger population of patients (such as historical data stored within the apparatus), or even the defibrillator apparatus itself. Myriad different uses for the output of the decision module 2508 are envisioned by the present invention, such uses being readily implemented by those of ordinary skill in the field given the present disclosure.

In one exemplary embodiment of the decision module 2508, a fuzzy logic model is utilized in the decision making process. One such model useful with the present invention comprises the linguistic fuzzy model with Mamdani max-min inference, of the type well known in the art. Each STD crisp input is transformed through fuzzification to a fuzzy input. The corresponding fuzzy outputs are determined from a rule base inference table. The fuzzy outputs are then transformed to the crisp output (e.g., "shock scale" in the illustrated embodiment) having a prescribed range or scheme, through defuzzification. For example, in one scheme, the crisp outputs are present in the range of 0 to 4. Clearly, other ranges and schemes may be substituted.

Furthermore, it will be recognized that other decision making processes may be substituted for the fuzzy logic model described above. For example, a Bayesian logic or Dempster-Schaefer theory of evidence approach may be employed in providing a particular desired decision-making classifier. Literally any system which can effectively utilize the output of the ICG module to provide accurate and coherent shock/no-shock decisions may be used. The foregoing fuzzy model, however, has the advantages of being readily adapted to the parametric value outputs (i.e., STDs) of the ICG module, and comparatively simple implementation.

In the exemplary crisp output scheme (0 to 4), a shock scale value of less than "3" results in a no-shock decision.

Figure 29:
FIG. 29 is a functional block diagram illustrating an exemplary decision module architecture (fuzzy logic) used with the apparatus of FIG. 24.
Figure 30A:
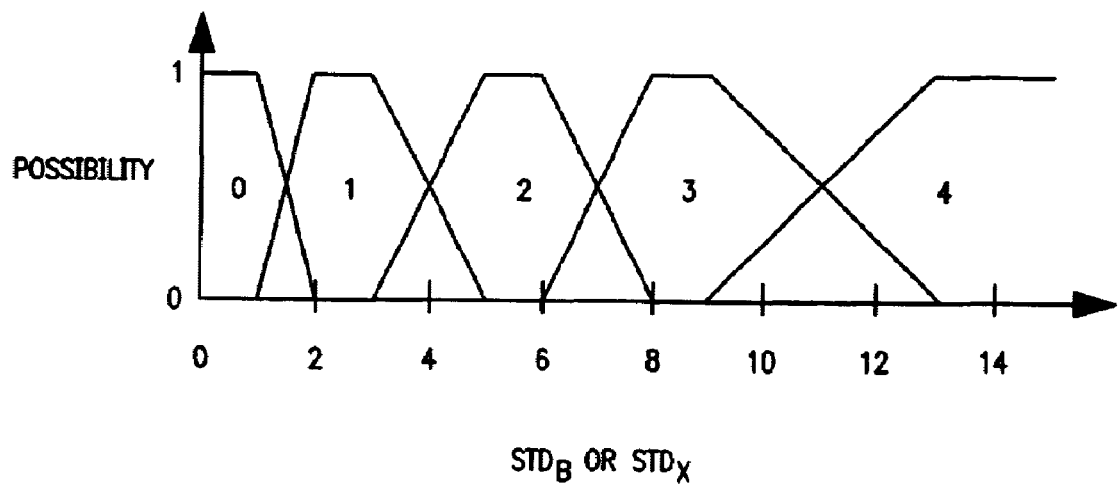
FIGS. 30a and 30b are a graphical representation of exemplary fuzzy input and output membership functions, respectively, used with the decision module architecture of FIG. 29.
Figure 30B:
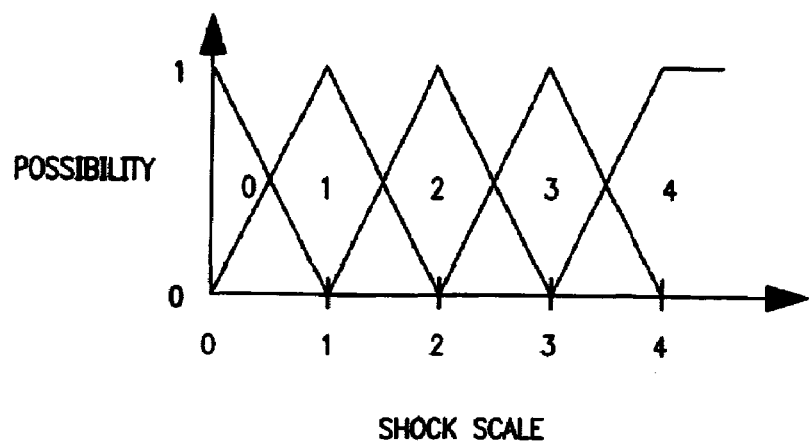

A shock scale of greater than or equal to "3" results in a shock decision being output from the decision module 2508 (See FIG. 29). The input and output membership functions used in the exemplary fuzzification/defuzzification model described above are shown in FIGS. 30a and 30b, respectively. It will be appreciated, however, that other membership functions may be used in place of those shown in FIGS. 30a and 30b.

The rule base inference table, which defines the relationship between fuzzy inputs and outputs is determined from, for example, standard empirical tuning of ICG waveforms of the type well known in the art, although other methods of determining the relationship between fuzzy inputs and outputs such as artificial neural network tuning may be employed consistent with the invention.

In the exemplary embodiment, the foregoing functionality is configured within the ICG module or "yoke" of the type previously described in detail herein. A variety of configurations may be utilized, such as removable circuit cards, SoC systems, or even devices where portions of the functionality are distributed over multiple physically discrete components.

As discussed previously herein, prior art automatic external defibrillator and automatic defibrillator arrhythmia detection algorithms are generally based on waveform time domain morphologies, with decision-making strategies based on coarse criteria such as absolute threshold. These empirical methodologies suffer from decreased sensitivity for detecting rhythms such as rapid ventricular tacchycardia. Since (external) defibrillator arrhythmia analysis is essentially conducted to determine if insufficient cardiac output is present (thereby warranting countershock therapy), the prior art has suggested use of the impedance cardiogram as a hemodynamic indicator. However, such prior art approaches suffer from very poor quality results, to the point of being ineffective or unreliable at differentiating between instances where countershock therapy is required and is not required. This poor performance stems from a variety of causes including, e.g., failure to consider the electric field distribution relating to electrode configuration; use of ensemble averaging of dZ/dt, with respect to the R point; and use of C point amplitude as the basis for classifying shockable rhythms. Further, prior art techniques do not parse beats through detection of R points, or other features, but manually select beats and dZ/dt features.

In contrast, the foregoing methods and apparatus of the instant invention overcome these problems. Predetermined electrode spacing may be used to ensure ICG waveform features are captured with high resolution. Pacing spike detection may be implemented to prevent misclassification of pacing spikes as R points. A wavelet algorithm for efficient R point detection during arrhythmias is also optionally employed; by transformation to the time-scale domain, this wavelet technique is more resistant to noise artifact than empirical waveform processing in the time domain. Furthermore, an optional R point detection scheme involving no absolute thresholds increases the ability of the foregoing algorithm to effectively generalize among waveforms from the cardiac patient population. With efficient beat detection, the variability of B point and X point samples can advantageously be determined with high certainty. Use of a "non-crisp" model (such as fuzzy), rather than another absolute threshold, ensures that the decision module of the apparatus can provide the aforementioned generalization among the patient population.

These foregoing features (individually and collectively) help increase both the accuracy and robustness of the apparatus 2300. This accuracy and robustness is especially beneficial in the typical environment where the AED is used; i.e., in less-than-ideal locations and ambient conditions, with the AED being administered by an unskilled operator.

It will be recognized that the foregoing features including use of predetermined electrode configuration, use of pacing spike detection, use of a wavelet algorithm, use of a non-crisp decision model, etc., may be employed alone or in varying combinations within any method or apparatus under the present invention. Hence, depending on the desired level of accuracy and functionality for a given application or instrument, one or more of these features may be utilized. Such features may even be made optional or user-selectable if desired. For example, the use of pacing spike detection, wavelet processing, and non-crisp decision making may afford sufficient accuracy in the absence of electrodes with predetermined spacing. Similarly, wavelet processing may not be required in all circumstances, such as where very little noise artifact is present. The invention should therefore in no way be considered to be limited to specific combinations or the aggregation of all such features, but rather may be more broadly practiced with one or more features in isolation consistent with the foregoing description and the claims appended hereto.

Also, it will be appreciated that while the ECG and ICG signal processing set forth herein is described primarily in terms of software algorithms, performance of at least portions of these analysis may be performed in hardware, such as for example in pre-configured logic gates (e.g., FPGAs or ASICs) or DSP front-end or back-end analog processing. The present invention should therefore not be considered to be limited to software-based processing.

It will be further recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

APPENDIX I

| ICG MODULE PARAMETERS | | |
|---|---|---|
| Abbreviation | Description of Parameter | Unit |
| ACI | Acceleration Index = $\dfrac{d^2 Z(t)}{dt^2}_{max} \Big/ Z_o$ | $s^{-2}$ |
| BP | Blood Pressure | MmHg |
| BSA | Body Surface Area | $m^2$ |

APPENDIX I-continued

ICG MODULE PARAMETERS

| Abbreviation | Description of Parameter | Unit |
|---|---|---|
| CI | Cardiac Index (CO divided by BSA) | $L\ min^{-1}\ m^{-2}$ |
| CO | Cardiac Output | $L\ min^{-1}$ |
| CVP | Central Venous Pressure | MmHg |
| dZ/dt | First time-derivative of impedance Z | $\Omega\ s^{-1}$ |
| $d^2Z/dt^2$ | Second time-derivative of impedance Z | $\Omega\ s^{-2}$ |
| ECG | Electro Cardio Graph | Milli Volts/time |
| EDI | End-Diastolic Index (EDV divided by BSA) | $ml\ m^2$ |
| EDV | End-Diastolic Volume | Ml |
| EF | Ejection Fraction | % |
| ER | Ejection Ratio | % |
| HR | Heart Rate | Bpm |
| IC | Index of Contractility $= \dfrac{dZ(t)}{dt_{max}} \Big/ Z_o$ | $s^{-1}$ |
| LCW | Left Cardiac Work | Kg m |
| LCWI | Left Cardiac Work Index | $Kg\ m\ m^{-2}$ |
| LSW | Left Stroke Work | G m |
| LSWI | Left Stroke Work Index | $G\ m\ m^{-2}$ |
| LVET | Left-Ventricular Ejection Time (also known as VET) | Ms |
| MAP | Mean Arterial Pressure | MmHg |
| PAP | Pulmonary Arterial Pressure | MmHg |
| PAOP | Pulmonary Artery Occluded Pressure | MmHg |
| PEP | Pre-Ejection Period | Ms |
| PF | Peak Flow | $ml\ s^{-1}$ |
| SI | Strike Index (SV divided by BSA) | $ml\ m^{-2}$ |
| $SpO_2$ | Saturation of Arterial Oxygen | % |
| STR | Systolic Time Ratio or Systolic Time Interval | — |
| SV | Stroke Volume | Ml |
| SVR | Systemic Vascular Resistance (using CO) | $MmHg\ min\ L^{-1}$ |
| SVRI | Systemic Vascular Resistance (using CI) | $MmHg\ min\ L^{-1}\ m^{-2}$ |
| SSRI | Systemic Vascular Resistance (using SI) | $MmHg\ ml^{-1}\ m{-2}$ |
| TFC | Thoracic Fluid Contents = $1/Z_0$ | $k\Omega^{-1}$ |
| TFI | Thoracic Fluid Index, equals $Z_0$ | $\Omega$ |
| VEPT | Volume of Electrically Participating Tissue | Ml |
| Z | Impedance = $Z_0 + \Delta Z$ | $\Omega$ |
| $Z_0$ | Base Impedance (averaged), equals TFI | $\Omega$ |
| $\Delta Z$ | Delta Z, dynamic component of impedance Z | $\Omega$ |

APPENDIX II

ICG MODULE PATIENT DATA COMMUNICATION PROTOCOL

| Data | DPR address | Description |
|---|---|---|
| CO ($L * min^{-1}$) | 7F50 | CO * 1000 |
| CI ($L * min^{-1} * m^{-2}$) | 7F52 | CI * 1000 |
| SI ($ml * m^{-2}$) | 7F54 | SI * 10 |
| SV (ml) | 7F56 | SV * 10 |
| SVR ($mmHg * min * L^{-1}$) | 7F58 | |
| SVRI ($mmHg * min * L^{-1} * m^2$) | 7F5A | |
| HR (bpm) | 7F5C | |
| MAP (mmHg) | 7F5E | |
| TFC ($\Omega^{-1}$) | 7F60 | TFC * 1000 |
| IC ($sec^{-1}$) | 7F62 | IC * 1000 |
| ACI ($sec^{-2}$) | 7F64 | ACI * 1000 |
| LCW (kg * m) | 7F66 | LCW * 100 |
| LCWI ($kg * m * m^{-2}$) | 7F68 | LCWI * 100 |
| PEP (ms) | 7F6A | |
| LVET (ms) | 7F6C | |
| STR | 7F6E | STR * 100 |
| RR (bpm) | 7F70 | |
| SSRI ($mmHg * ml^{-1} * m^2$) | 7F72 | SSRI * 10 |
| LSWI ($g * m * m^{-2}$) | 7F74 | LSWI * 10 |
| EF (%) | 7F76 | |
| Program_ver_hundredth | 7F78 | 0.0X |
| Program_ver_tenth | 7F7A | 0.X0 |
| Program_ver_ones | 7F7C | X.00 |
| VEPT | 7F92 | Milliliters |
| Ideal Weight | 7F94 | Kilograms * 100 |
| BSA | 7F96 | BSA ($m^2$) * 100 |

What is claimed is:

1. Defibrillation apparatus, comprising:
   a defibrillation energy source;
   a plurality of first electrodes adapted for the delivery of defibrillating energy generated by said source to a subject;
   a plurality of second electrodes adapted for obtaining electrocardiographic and impedance signals from said subject, at least two of said plurality of second electrodes being disposed in an optimized spacing relative to one another;
   a stimulation current source operatively coupled to at least one of said plurality of second electrodes;
   first processing apparatus adapted to process said electrocardiographic signals to generate first output, said processing of said electrocardiographic signals comprising at least time-scale domain processing;
   second processing apparatus adapted to process said impedance signals and said first output to generate second output, said processing of said impedance signals and first output comprising at least B and X point detection; and
   fuzzy logic decision apparatus adapted to receive said second output and determine whether said delivery of defibrillating energy is appropriate based at least in part thereon.

2. The apparatus of claim 1, further comprising pacing spike detection apparatus adapted to detect one or more pacing spikes within said electrocardiographic signals.

3. The apparatus of claim 1, wherein at least a portion of said pluralities of first and second electrodes are disposed within a common electrode structure.

4. The apparatus of claim 3, wherein said common electrode structure comprises a single one of said first electrodes and two of said second electrodes, said two second electrodes being disposed in said optimized spacing.

5. Defibrillation apparatus, comprising:
   a defibrillation energy source;
   a plurality of first electrodes adapted for the delivery of defibrillating energy generated by said source to a subject;
   a plurality of second electrodes adapted for obtaining impedance signals from said subject, at least two of said plurality of second electrodes being disposed in an optimized spacing relative to one another;
   a stimulation current source operatively coupled to at least one of said plurality of second electrodes; and
   fuzzy decision logic adapted to determine whether to deliver said energy to said subject based at least in part on said impedance signals.

6. The apparatus of claim 5, wherein said act of determining comprises:
   determining the location of each of a plurality of artifacts contained within said signals;
   determining at least one parameter associated with said locations; and
   determining whether to deliver said energy based at least in part on said at least one parameter.

7. The apparatus of claim 6, wherein said artifacts comprise B or X points, and said at least one parameter comprises the standard deviation of said locations associated with said B or X points.

8. A method of evaluating whether to apply defibrillating shock to a subject, comprising:
   obtaining waveforms from said subject;
   detecting beats within said waveforms;
   based at least in part on said act of detecting beats, detecting a plurality of fiducial points within said waveforms;
   processing said fiducial points to generate at least one parameter relating to the cardiac function of said subject; and
   evaluating, using fuzzy logic, whether to apply said shock based at least in part on said at least one parameter.

9. The method of claim 8, wherein said act of obtaining waveforms comprises obtaining impedance waveforms using electrodes having an optimized terminal spacing.

10. The method of claim 8, wherein said act of detecting beats comprises forming at least one time-scale domain representation of at least a portion of said waveforms, and using said at least one representation to identify at least one artifact therein.

11. The method of claim 8, wherein said act of detecting a plurality of fiducial points comprises detecting C, B, and X points within said waveforms.

12. The method of claim 8, wherein said act of processing said fiducial points comprises:
   determining the locations of a plurality of individual ones of said points within different beats within said waveforms; and
   generating said at least one parameter based at least in part on said locations, said at least one parameter being related to the variation of said locations over said different beats.

13. A method of evaluating whether to apply defibrillating shock to a subject, comprising:
   obtaining waveforms from said subject;
   detecting beats within said waveforms;
   based at least in part on said act of detecting beats, detecting a plurality of fiducial points within said waveforms;
   processing said fiducial points to generate at least one parameter relating to the cardiac function of said subject; and
   evaluating whether to apply said shock based at least in part on said at least one parameter;
   wherein said act of processing said fiducial points comprises:
      determining the locations of a plurality of individual ones of said points within different beats within said waveforms; and
      generating said at least one parameter based at least in part on said locations, said at least one parameter being related to the variation of said locations over said different beats.

14. The method of claim 13, wherein said act of obtaining waveforms comprises obtaining impedance waveforms using electrodes having an optimized terminal spacing.

15. The method of claim 13, wherein said act of detecting beats comprises forming at least one time-scale domain representation of at least a portion of said waveforms, and using said at least one representation to identify at least one artifact therein.

16. The method of claim 13, wherein said act of detecting a plurality of fiducial points comprises detecting C, B, and X points within said waveforms.

17. A method of substantially avoiding the application of unnecessary defibrillation shocks to a living subject, comprising:
   obtaining impedance and electrocardiographic waveforms from said subject;
   accurately determining cardiac output using at least said waveforms; and
   correlating said cardiac output determination to physiologic conditions not requiring defibrillation;
   wherein said act of accurately determining cardiac output comprises identifying a plurality of fiducial points within said waveforms and evaluating the variation associated with at least a portion of said fiducial points across several beats.

18. The method of claim 17, wherein said act of obtaining impedance waveforms comprises obtaining said waveforms using electrodes having a predetermined spacing.

19. The method of claim 17, wherein said act of correlating comprises correlating said output determination to non-shockable rhythms of said subject.

20. A method of determining the need for defibrillating shock for a subject, comprising:
   obtaining waveforms from said subject;
   detecting at least one artifact within said waveforms;
   based at least in part on said act of detecting at least one artifact, detecting at least one fiducial point within said waveforms;
   processing said at least one fiducial point to generate at least one parameter relating to the cardiac function of said subject; and
   determining, using fuzzy logic, the need for said shock based at least in part on said at least one parameter.

21. The method of claim 20, wherein said act of obtaining waveforms comprises obtaining impedance waveforms using electrodes having an optimized terminal spacing.

22. The method of claim 20, wherein said act of detecting at least one artifact comprises forming at least one time-scale domain representation of at least a portion of said waveforms, and using said at least one representation to identify at least one artifact therein.

23. The method of claim 20, wherein said act of detecting at least one fiducial point comprises detecting at least two of C, B, and X points within said waveforms.

24. A method of determining the need for defibrillating shock for a subject, comprising:
   obtaining waveforms from said subject;
   detecting at least one artifact within said waveforms;
   based at least in part on said act of detecting at least one artifact, detecting at least one fiducial point within said waveforms;
   processing said at least one fiducial point to generate at least one parameter relating to the cardiac function of said subject; and
   determining the need for said shock based at least in part on said at least one parameter;

wherein said act of processing said at least one fiducial point comprises:
  determining the locations of a plurality of individual ones of said points within different beats within said waveforms; and
  generating said at least one parameter based at least in part on said locations, said at least one parameter being related to the variation of said locations over said different beats.

25. The method of claim 24, wherein said act of determining comprises using fuzzy logic to evaluate said at least one parameter.

26. The method of claim 24, wherein said act of obtaining waveforms comprises obtaining impedance waveforms using electrodes having an optimized terminal spacing.

27. A method of operating defibrillation apparatus that can apply defibrillation shocks to a living subject, comprising:
  obtaining impedance and electrocardiographic waveforms from said subject;
  determining cardiac output using at least said waveforms; and
  correlating said cardiac output determination to physiologic conditions not requiring defibrillation;
  wherein said act of determining cardiac output comprises identifying a plurality of fiducial points within said waveforms and evaluating the variation associated with at least a portion of said fiducial points across several beats.

28. The method of claim 27, wherein said act of obtaining impedance waveforms comprises obtaining said waveforms using electrodes having a predetermined spacing.

29. The method of claim 27, wherein said act of correlating comprises correlating said output determination to non-shockable rhythms of said subject.

30. A method of operating a defibrillating apparatus capable of delivering a defibrillating shock to a subject, comprising:
  obtaining waveforms from said subject;
  detecting beats within said waveforms;
  based at least in part on said act of detecting beats, detecting a plurality of fiducial points within said waveforms;
  processing said fiducial points to generate at least one parameter relating to the cardiac function of said subject; and
  determining whether to apply said shock based at least in part on said at least one parameter;
  wherein said act of processing said fiducial points comprises:
    determining the positions of a plurality of individual ones of said points within different beats within said waveforms; and
    generating said at least one parameter based at least in part on said positions,
  said at least one parameter being related at least in part to the variation of said positions over said different beats.

31. The method of claim 30, wherein said act of obtaining waveforms comprises obtaining impedance waveforms using electrodes having an optimized terminal spacing.

32. The method of claim 30, wherein said act of detecting beats comprises forming at least one time-scale domain representation of at least a portion of said waveforms, and using said at least one representation to identify at least one artifact therein.

33. The method of claim 30, wherein said act of detecting a plurality of fiducial points comprises detecting C, B, and X points within said waveforms.

34. Defibrillation apparatus, comprising:
  a defibrillation energy source;
  a plurality of first electrodes adapted for the delivery of defibrillating energy generated by said source to a subject;
  a plurality of second electrodes adapted for obtaining impedance signals from said subject;
  a stimulation current source operatively coupled to at least one of said plurality of second electrodes; and
  decision logic adapted to determine whether to deliver said energy to said subject based at least in part on:
    identifying a plurality of fiducial points within said impedance signals; and
    evaluating the variation associated with at least a portion of said fiducial points across multiple beats associated with said impedance signals.

35. The apparatus of claim 34, wherein at least two of said plurality of second electrodes are disposed in an optimized spacing relative to one another.

36. The apparatus of claim 34, wherein said fiducial points comprise B or X points, and said variation comprises the standard deviation of said locations associated with said B or X points with said multiple beats.

37. Defibrillation apparatus, comprising:
  means for providing defibrillation energy;
  a plurality of first electrodes adapted for the delivery of defibrillating energy generated by said source to a subject;
  a plurality of second electrodes adapted for obtaining impedance signals from said subject;
  means for providing stimulation current, said means operatively coupled to at least one of said plurality of second electrodes; and
  means adapted to determine whether to deliver said energy to said subject based at least in part on:
    identifying a plurality of fiducial points within said impedance signals; and
    evaluating the variation associated with at least a portion of said fiducial points across multiple beats associated with said impedance signals.

38. The apparatus of claim 37, wherein at least two of said plurality of second electrodes are disposed in an optimized spacing relative to one another.

39. The apparatus of claim 37, wherein said fiducial points comprise B or X points, and said variation comprises the standard deviation of said locations associated with said B or X points with said multiple beats.

40. Apparatus adapted to evaluate the need for applying defibrillation energy to a living subject, comprising:
  defibrillation apparatus configured to selectively apply said defibrillation energy to said subject;
  impedance cardiography apparatus adapted to generate impedance cardiography signals from said subject; and
  decision apparatus operatively communicating with at least said cardiography apparatus, said decision apparatus being adapted to perform said evaluation at least in part using fuzzy decision logic as applied to said impedance cardiography signals obtained from said subject during successive intervals.

41. The apparatus of claim 40, wherein said impedance cardiography apparatus further comprises a plurality of electrodes, wherein at least two of said plurality of electrodes are disposed in an optimized spacing relative to one another.

* * * * *